United States Patent
Chinnaiyan et al.

(10) Patent No.: US 11,746,151 B2
(45) Date of Patent: Sep. 5, 2023

(54) COMPOSITIONS AND METHODS FOR TREATING CANCER

(71) Applicant: The Regents of the University of Michigan, Ann Arbor, MI (US)

(72) Inventors: Arul Chinnaiyan, Northville, MI (US); Dan Robinson, Ann Arbor, MI (US); Yi-Mi Wu, Ann Arbor, MI (US); Marcin Cieslik, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 17/046,998

(22) PCT Filed: Apr. 12, 2019

(86) PCT No.: PCT/US2019/027160
§ 371 (c)(1),
(2) Date: Oct. 12, 2020

(87) PCT Pub. No.: WO2019/200214
PCT Pub. Date: Oct. 17, 2019

(65) Prior Publication Data
US 2021/0155695 A1 May 27, 2021

Related U.S. Application Data

(60) Provisional application No. 62/657,055, filed on Apr. 13, 2018.

(51) Int. Cl.
*C07K 16/28* (2006.01)
*A61P 35/00* (2006.01)
*C12Q 1/6886* (2018.01)

(52) U.S. Cl.
CPC .......... *C07K 16/2818* (2013.01); *A61P 35/00* (2018.01); *C07K 16/28* (2013.01); *C12Q 1/6886* (2013.01); *C07K 2317/21* (2013.01); *C07K 2317/24* (2013.01); *C07K 2319/30* (2013.01); *C12Q 2600/106* (2013.01); *C12Q 2600/156* (2013.01)

(58) Field of Classification Search
CPC ................ C07K 16/2818; C07K 16/28; C07K 2317/21; C07K 2317/24; C07K 2319/30; A61P 35/00; C12Q 1/6886; C12Q 2600/106; C12Q 2600/156
See application file for complete search history.

(56) References Cited

U.S. PATENT DOCUMENTS

2013/0225433 A1   8/2013   Chinnaiyan et al.
2017/0157212 A1*  6/2017   Jones ..................... A61K 45/06

FOREIGN PATENT DOCUMENTS

| WO | WO 2016/014565 | 1/2016 |
| WO | WO 2016/207661 | 12/2016 |
| WO | WO 2017/156263 | 9/2017 |
| WO | WO 2017/163076 | 9/2017 |
| WO | WO 2017/223344 | 12/2017 |

OTHER PUBLICATIONS

Armenia et al, The long tail of oncogenic drivers in prostate cancer, Nat. Genet., Apr. 2, 2018, 50, pp. 645-651 (Year: 2018).*
Wei et al, Indirubin inhibits the proliferation of prostate cancer PC-3 cells, Zhonghua Nan Ke Xue, Sep. 2015, 21(9), pp. 788-791 (Year: 2015).*
Mazor et al., Inhibition of glycogen synthase kinase-3 represses androgen receptor activity and prostate cancer cell growth, Oncogene, 2004, 23, pp. 7882-7892 (Year: 2004).*
International Search Report and Written Opinion for PCT/US2019/027160, dated Jul. 15, 2019. 18 pages.
Extended European Search Report for PCT/US2019027160, dated Dec. 9, 2021. 12 pages.
Abida et al., Prospective Genomic Profiling of Prostate Cancer Across Disease States Reveals Germline and Somatic Alterations That May Affect Clinical Decision Making. JCO Precis Oncol. Jul. 2017;2017:PO.17.00029. 26 pages.
Alexandrov et al., Signatures of mutational processes in human cancer. Nature. Aug. 22, 2013;500(7463):415-21.
Antonarakis. Cyclin-dependent kinase 12, immunity and prostate cancer. N Engl J Med 2018; 379:1087-1089.
Armenia et al., The long tail of oncogenic drivers in prostate cancer. Nat Genet. May 2018;50(5):645-651.
Ashworth et al., Genetic interactions in cancer progression and treatment. Cell. Apr. 1, 2011;145(1):30-8.
Beltran et al., Divergent clonal evolution of castration-resistant neuroendocrine prostate cancer. Nat Med. Mar. 2016;22(3):298-305.
Bernard et al., Myc confers androgen-independent prostate cancer cell growth. J Clin Invest. Dec. 2003;112(11):1724-31.
Blazek et al., The Cyclin K/Cdk12 complex maintains genomic stability via regulation of expression of DNA damage response genes. Genes Dev. Oct. 15, 2011;25(20):2158-72.
Bolotin et al., MiXCR: software for comprehensive adaptive immunity profiling. Nat Methods. May 2015;12(5):380-1.
Bretones et al., Myc and cell cycle control. Biochim Biophys Acta. May 2015;1849(5):506-16.
Chan et al., Secondary lymphoid-tissue chemokine (SLC) is chemotactic for mature dendritic cells. Blood. Jun. 1, 1999;93(11):3610-6.
Ciccarese et al., Prostate cancer heterogeneity: Discovering novel molecular targets for therapy. Cancer Treat Rev. Mar. 2017;54:68-73.
Curiel et al., Specific recruitment of regulatory T cells in ovarian carcinoma fosters immune privilege and predicts reduced survival. Nat Med. Sep. 2004;10(9):942-9.

(Continued)

*Primary Examiner* — Mark Halvorson
*Assistant Examiner* — Dennis J Sullivan
(74) *Attorney, Agent, or Firm* — Casimir Jones, S.C.; Tanya A. Arenson

(57) ABSTRACT

Provided herein are compositions and methods for treating cancer. In particular, provided herein are compositions, methods, and uses of targeted therapy to treat cancer (e.g., prostate cancer) in subjects with CDK12 mutations.

9 Claims, 25 Drawing Sheets
Specification includes a Sequence Listing.

(56) References Cited

OTHER PUBLICATIONS

Ekumi et al., Ovarian carcinoma CDK12 mutations misregulate expression of DNA repair genes via deficient formation and function of the Cdk12/CycK complex. Nucleic Acids Res. Mar. 11, 2015;43(5):2575-89.
Fraser et al., Genomic hallmarks of localized, non-indolent prostate cancer. Nature. Jan. 19, 2017;541(7637):359-364.
Gosling et al., Cutting edge: identification of a novel chemokine receptor that binds dendritic cell- and T cell-active chemokines including ELC, SLC, and TECK. J Immunol. Mar. 15, 2000;164(6):2851-6.
Herschkowitz et al., The functional loss of the retinoblastoma tumour suppressor is a common event in basal-like and luminal B breast carcinomas. Breast Cancer Res. 2008;10(5):R75. 13 pages.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53.
Juan et al., Cdk12 is essential for embryonic development and the maintenance of genomic stability. Cell Death Differ. Jun. 2016;23(6):1038-48.
Kumar et al., Substantial interindividual and limited intraindividual genomic diversity among tumors from men with metastatic prostate cancer. Nat Med. Apr. 2016;22(4):369-78.
Le et al., PD-1 Blockade in Tumors with Mismatch-Repair Deficiency. N Engl J Med. Jun. 25, 2015;372(26):2509-20.
Liberzon et al., The Molecular Signatures Database (MSigDB) hallmark gene set collection. Cell Syst. Dec. 23, 2015;1(6):417-425.
Manogue et al., Biomarkers for programmed Death-1 inhibition in prostate cancer. The Oncologist. 2019. vol. 24, No. 4. pp. 444-448.
Mcgranahan et al., Clonal neoantigens elicit T cell immunoreactivity and sensitivity to immune checkpoint blockade. Science. Mar. 25, 2016;351(6280):1463-9.
Mermel et al., GISTIC2.0 facilitates sensitive and confident localization of the targets of focal somatic copy-number alteration in human cancers. Genome Biol. 2011;12(4):R41. 14 pages.
Nagarsheth et al., Chemokines in the cancer microenvironment and their relevance in cancer immunotherapy. Nat Rev Immunol. Sep. 2017;17(9):559-572.
Nishino et al., Anti-PD-1-Related Pneumonitis during Cancer Immunotherapy. N Engl J Med. Jul. 16, 2015;373(3):288-90.

O'Neil et al., Synthetic lethality and cancer. Nat Rev Genet. Oct. 2017;18(10):613-623.
Otto et al., Cell cycle proteins as promising targets in cancer therapy. Nat Rev Cancer. Jan. 27, 2017;17(2):93-115.
Palanisamy et al., Rearrangements of the RAF kinase pathway in prostate cancer, gastric cancer and melanoma. Nat Med. Jul. 2010;16(7):793-8.
Parikh et al., Effects of TP53 mutational status on gene expression patterns across 10 human cancer types. J Pathol. Apr. 2014;232(5):522-33.
Petrylak et al., Docetaxel and estramustine compared with mitoxantrone and prednisone for advanced refractory prostate cancer. N Engl J Med. Oct. 7, 2004;351(15):1513-20.
Polak et al., A mutational signature reveals alterations underlying deficient homologous recombination repair in breast cancer. Nat Genet. Oct. 2017;49(10):1476-1486.
Rescigno et al., Immunotherapy for lethal prostate cancer. Nature Reviews Urology. Nature Reviews Urology. 2018. vol 16, No. 2. pp. 69-70.
Robinson et al., Integrative clinical genomics of advanced prostate cancer. Cell. May 21, 2015;161(5):1215-1228.
Robinson et al., Integrative clinical genomics of metastatic cancer. Nature. Aug. 17, 2017;548(7667):297-303.
Saal et al., Poor prognosis in carcinoma is associated with a gene expression signature of aberrant PTEN tumor suppressor pathway activity. Proc Natl Acad Sci U S A. May 1, 2007;104(18):7564-9.
Temko et al., The effects of mutational process and selection on driver mutations across cancer types. BioRxiv. 2017. 20 pages.
Vicari et al., TECK: a novel CC chemokine specifically expressed by thymic dendritic cells and potentially involved in T cell development. Immunity. Aug. 1997;7(2):291-301.
Wu et al., Identification of targetable FGFR gene fusions in diverse cancers. Cancer Discov. Jun. 2013;3(6):636-47.
Wu et al., Inactivation of CDK12 Delineates a Distinct Immunogenic Class of Advanced Prostate Cancer. Cell. Jun. 14, 2018;173(7):1770-1782.e14.
Yu et al., Alterations of BRAF and HIPK2 loci predominate in sporadic pilocytic astrocytoma. Neurology. Nov. 10, 2009;73(19):1526-31.
Yuan et al., Androgen receptor remains critical for cell-cycle progression in androgen-independent CWR22 prostate cancer cells. Am J Pathol. Aug. 2006;169(2):682-96.
Zou. Regulatory T cells, tumour immunity and immunotherapy. Nat Rev Immunol. Apr. 2006;6(4):295-307.

* cited by examiner

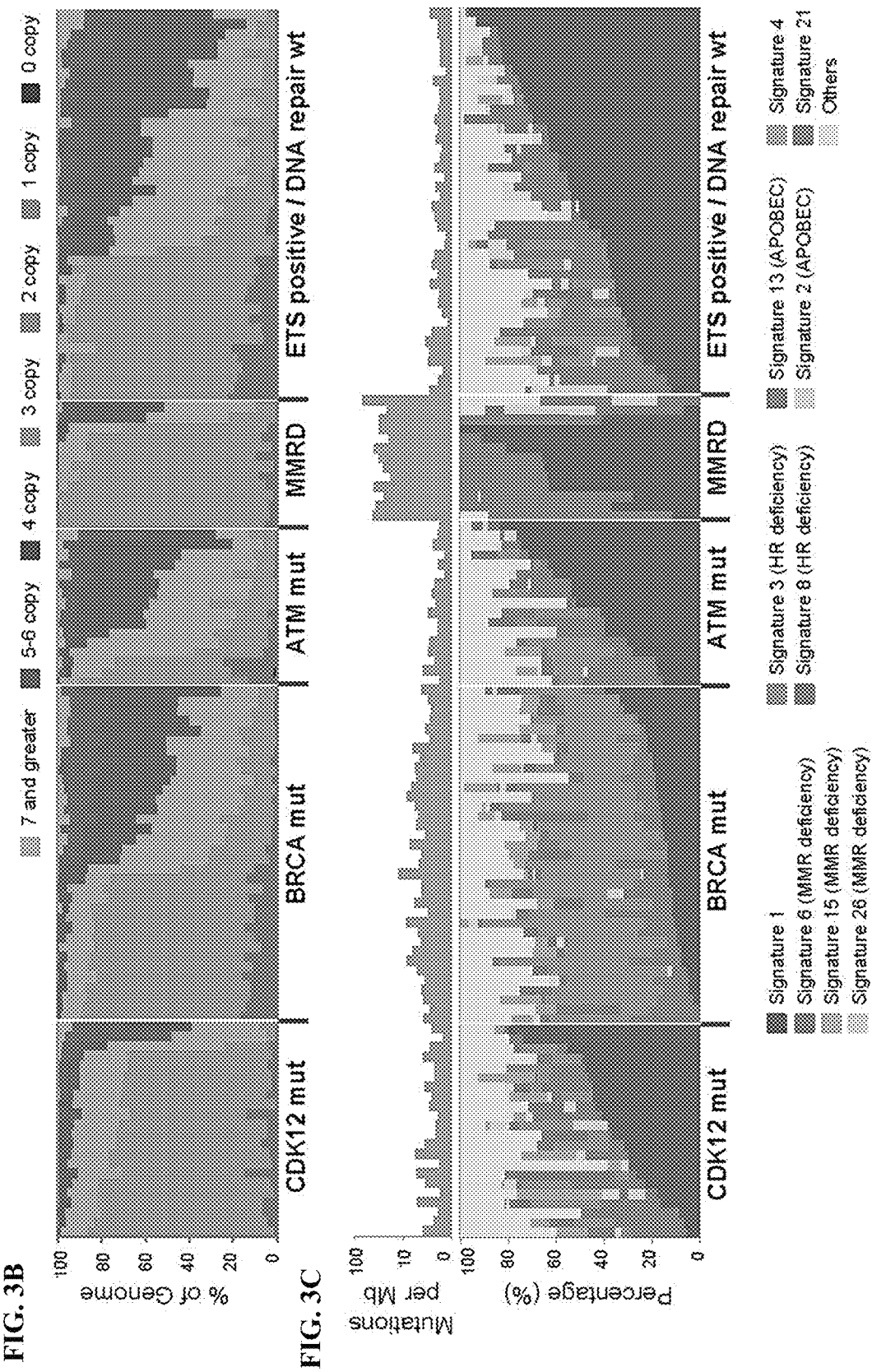

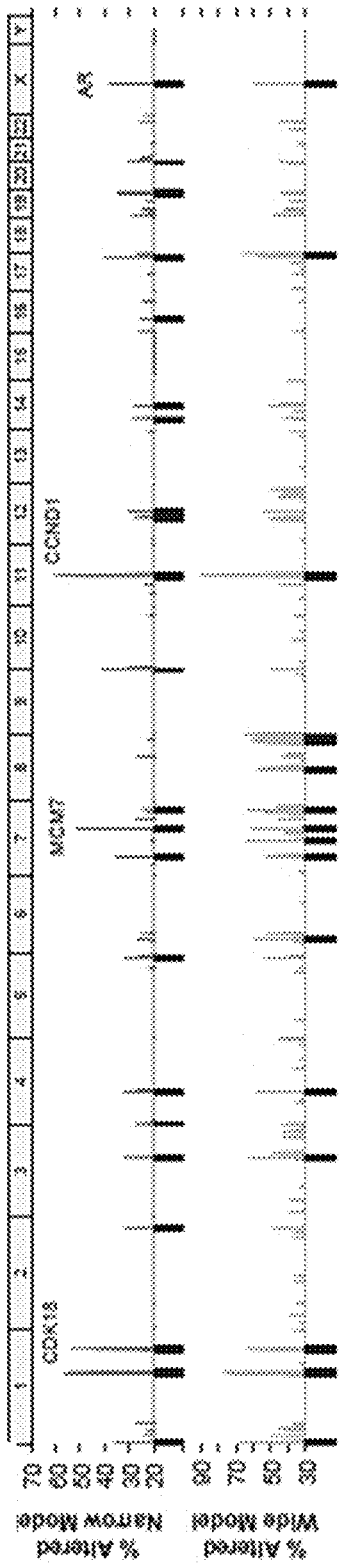
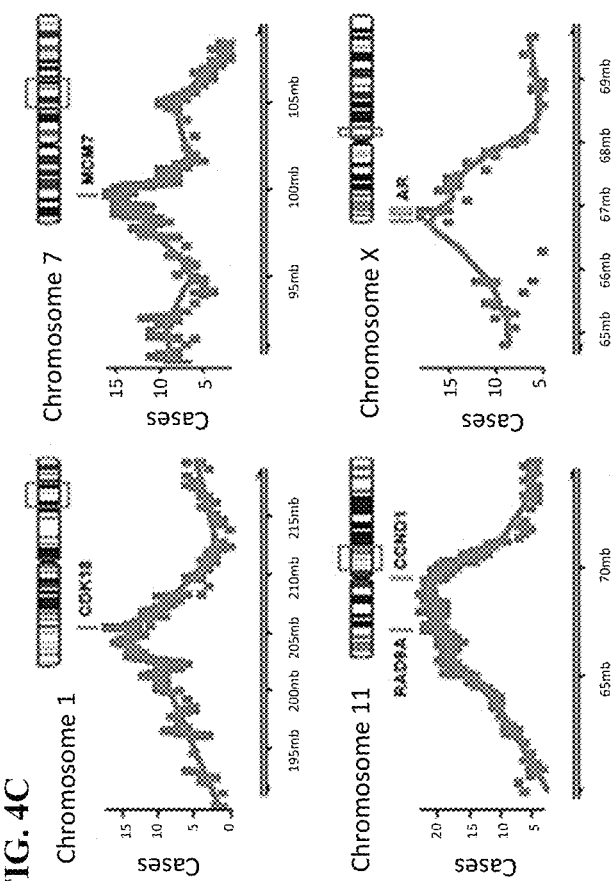
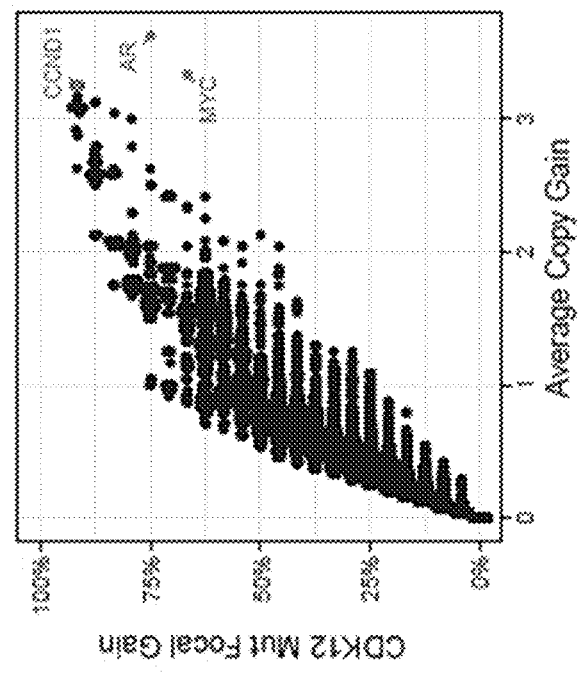
FIG. 4A
FIG. 4C
FIG. 4B

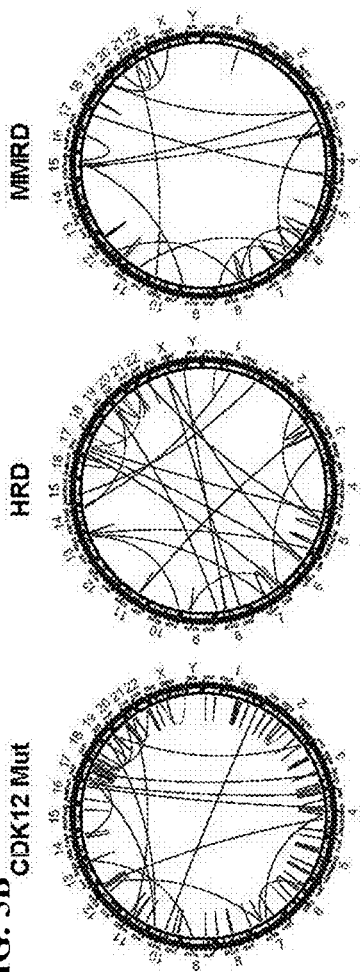
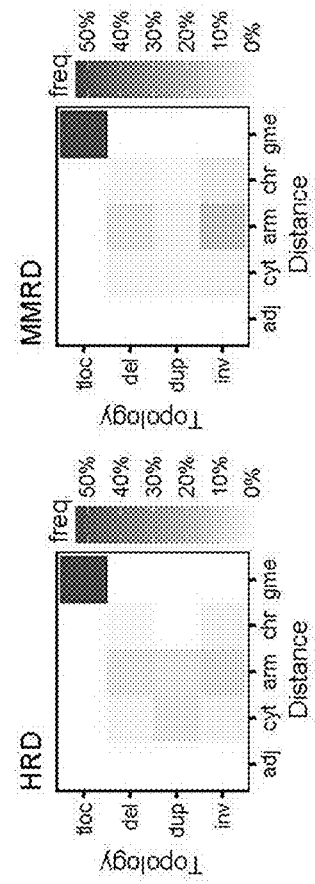
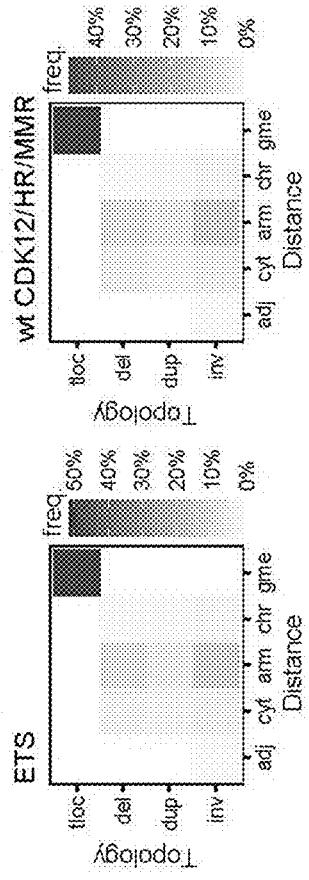
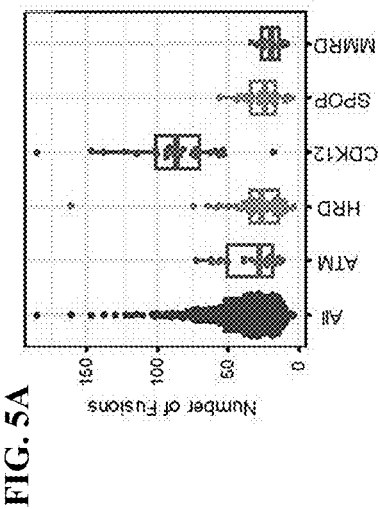
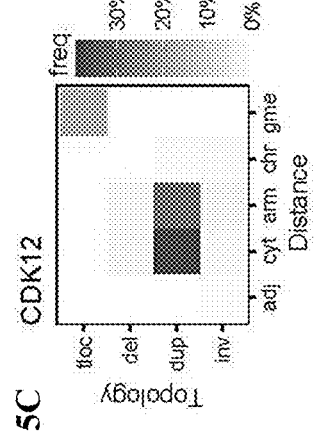
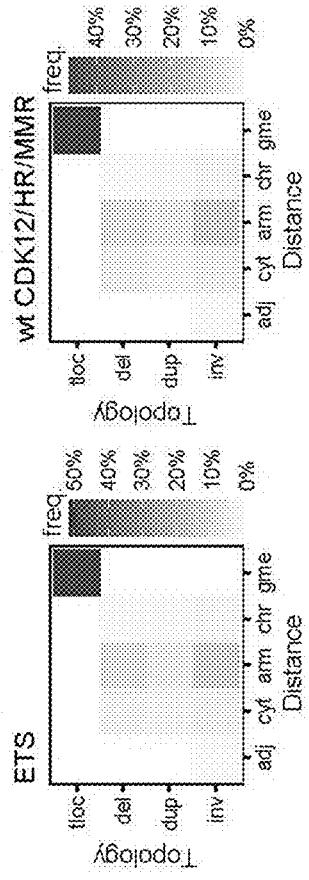
FIG. 5A
FIG. 5B
FIG. 5C

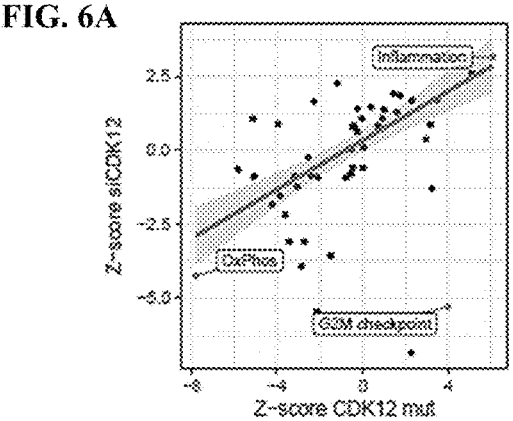
FIG. 6A
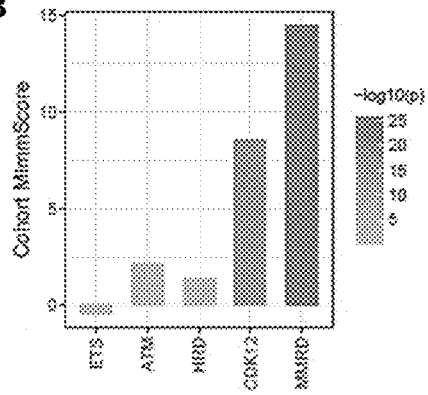
FIG. 6B
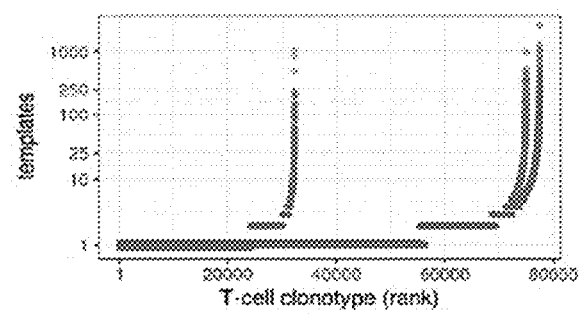
FIG. 6C
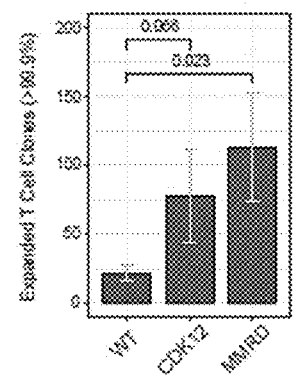
FIG. 6D
FIG. 6E
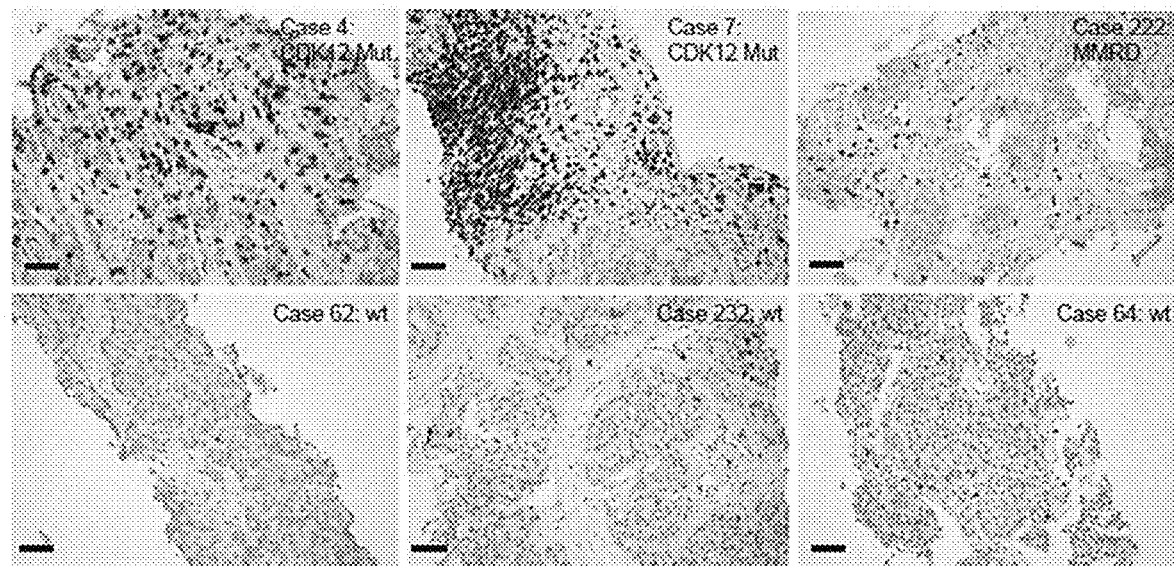

FIG. 11H MSigDB

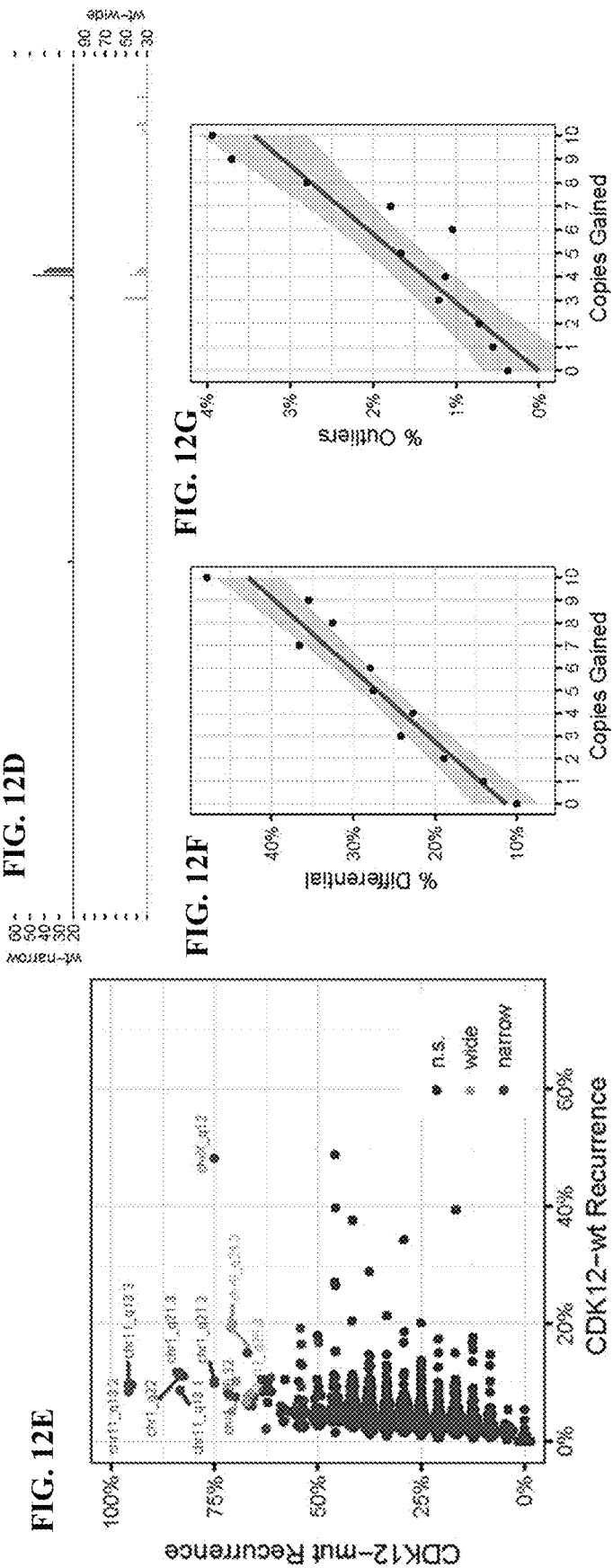

FIG. 13A
FIG. 13B
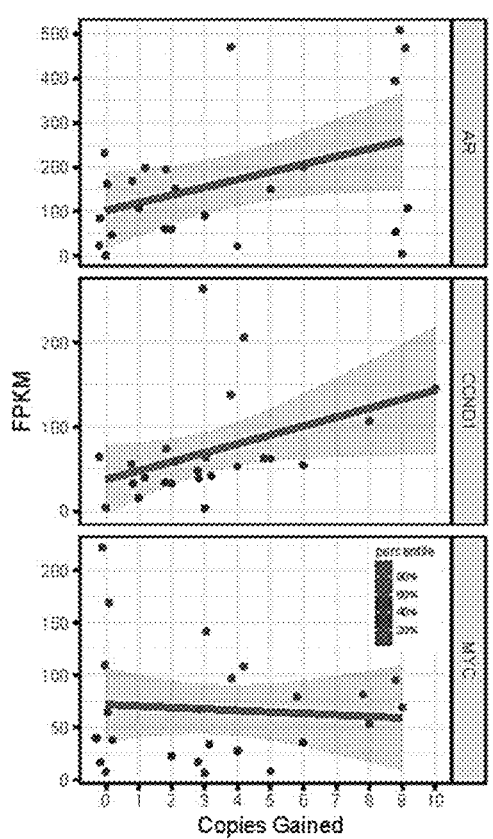
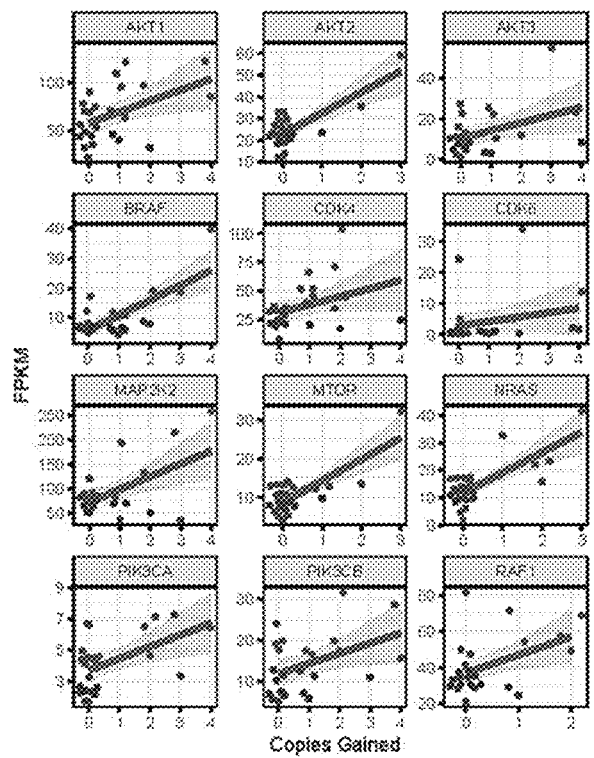
FIG. 13C
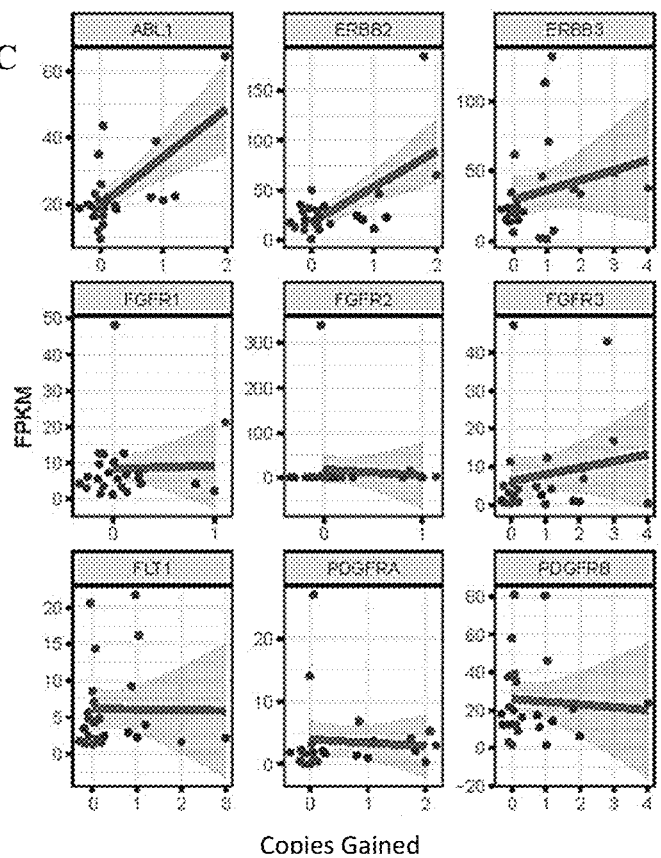
Copies Gained

COMPOSITIONS AND METHODS FOR TREATING CANCER

The present Application claims priority to U.S. Provisional Patent Application Ser. No. 62/657,055 filed Apr. 13, 2018, the disclosure of which is herein incorporated by reference in its entirety

STATEMENT REGARDING FEDERALLY SPONSORED RESEARCH OR DEVELOPMENT

The present Application is a national phase application under 35 U.S.C. § 371 of PCT International Application No. PCT/US2019/027160, filed Apr. 12, 2019, which claims priority to U.S. Provisional Patent Application Ser. No. 62/657,055 filed Apr. 13, 2018, the disclosure of which is herein incorporated by reference in its entirety.

FIELD

Provided herein are compositions and methods for treating cancer. In particular, provided herein are compositions, methods, and uses of targeted therapy to treat cancer (e.g., prostate cancer) in subjects with CDK12 mutations.

BACKGROUND

Prostate cancer is cancer that occurs in the prostate, a small walnut-shaped gland in men that produces the seminal fluid that nourishes and transports sperm. Prostate cancer is one of the most common types of cancer in men. Usually prostate cancer grows slowly and is initially confined to the prostate gland, where it may not cause serious harm. However, while some types of prostate cancer grow slowly and may need minimal or even no treatment, other types are aggressive and can spread quickly.

Prostate cancer that's detected early, when it's still confined to the prostate gland, has a better chance of successful treatment.

For patients with metastatic PCa that fail hormone therapy, the last line of defense are the taxane-derived chemotherapeutic agents docetaxel (Taxotere) or cabazitaxel (Jevtana). Response to taxane therapy is not durable. Progression-free survival on docetaxel treatment approaches 0% by 3 years (see, e.g., Petrylak D P, et al., New Engl J Med. 2004; 351(15): 1513-20).

There is a need for additional diagnostic and treatment options, particularly treatments customized to a patient's tumor.

SUMMARY

Provided herein are compositions and methods for treating cancer. In particular, provided herein are compositions, methods, and uses of targeted therapy to treat cancer (e.g., prostate cancer) in subjects with CDK12 mutations.

The compositions and methods described herein provide customized, targeted therapies for prostate cancer patients that are typically resistant to conventional therapies.

Thus, the present disclosure provides a needed improvement in patient care.

In some embodiments, provided herein is a method of treating cancer, comprising: a) detecting the presence of one or more inactivating mutations of CDK12 in a sample from a subject diagnosed with prostate cancer; and b) administering checkpoint inhibitor immunotherapy to subjects with one or more inactivating mutations of CDK12 (e.g., and not administering checkpoint immunotherapy to subjects lacking the inactivating mutations of CDK12). In some embodiments, the prostate cancer is castration-resistant prostate cancer. In some embodiments, the prostate cancer is metastatic prostate cancer. In some embodiments, the checkpoint inhibitor immunotherapy comprises an anti-PD-1 agent. The present disclosure is not limited to a particular anti-PD-1 agent. Examples include, but are not limited to, pembrolizumab, nivolumab, REGN2810. MED10680, CT-001, pidilizumab, AMP-224, AMP-514, or PDR001. In some embodiments, the activating mutations of CDK12 are truncating mutations. In some embodiments, the inactivating mutations of CDK12 are biallelic. In some embodiments, the inactivating mutations of CDK12 inactivate the kinase domain of CDK12.

Further embodiments provide the use of checkpoint inhibitor immunotherapy to treat prostate cancer in a subject comprising one or more inactivating mutations of CDK12 in a prostate cancer sample.

Additional embodiments provide a checkpoint immunotherapy agent for use in treating prostate cancer in a subject comprising one or more inactivating mutations of CDK12 in a prostate cancer sample.

In some embodiments, the identification may be conducted in whole or in part by a treating health care worker (or the subject). In some embodiments, samples obtained from a patient are sent to a laboratory for testing (e.g., a third party laboratory) and results are received by a treating health care worker. Sample collection, sample testing, and patient treatment may each be conducted by separate entities or multiple of such steps may be conducted by a single entity. For example, in some embodiments, a medical facility collects a patient sample, tests the sample, and administers a therapy to the patient. In some embodiments, the medical facility collects the sample and treats the patient, but testing is conducted by a third party laboratory that receives the sample and provides results to the medical facility. In some embodiments, a testing facility collects the sample and tests the sample and sends results to a medical facility that administers a therapy. In some embodiments, the patient collects the sample and sends it for testing (e.g., to a third party laboratory or the medical facility) and the medical facility administers a therapy. In some embodiments, a medical facility collects the sample, the testing laboratory tests the sample, and a patient self-administers a therapy.

Still other embodiments provide a method of determining a treatment course of action in a subject diagnosed with prostate cancer (e.g., providing information for treatment recommendation), comprising: a) detecting the presence of one or more inactivating mutations of CDK12 in a sample from a subject diagnosed with prostate cancer; and b) recommending administration of checkpoint inhibitor immunotherapy to subjects with one or more inactivating mutations of CDK12. In some embodiments, the method further comprises the step of generating a report that provides results sufficient to select administration of checkpoint inhibitor immunotherapy for subjects with CDK12 mutations.

In other embodiments, provided herein is a method of treating cancer, comprising: a) detecting the presence of one or more inactivating mutations of CDK12 in a sample from a subject diagnosed with prostate cancer; and b) administering an inhibitor of a cell cycle protein to subjects with one or more inactivating mutations of CDK12. In some embodiments, the cell cycle protein is CCND1, CCND2, CCND3, CCNE1, or CDK4. The present disclosure is not limited to particular inhibitors of cell cycle proteins. Examples include, but are not limited to, indirubin LY2835219, arcyriaflavin A, NSC 625987, CDK4 inhibitor, fascaplysin, alvocidib, PHA-793887, P276-00, AT7519, SU9516, BMS-265246, SNS-032, PD 0332991 hydrochloride, or R547.

Certain embodiments provide the use of a cell cycle protein inhibitor to treat prostate cancer in a subject comprising one or more inactivating mutations of CDK12 in a prostate cancer sample.

Further embodiments provide a method of determining a treatment course of action in a subject diagnosed with prostate cancer, comprising: a) detecting the presence of one or more inactivating mutations of CDK12 in a sample from a subject diagnosed with prostate cancer; and b) recommending administration of an inhibitor of a cell cycle protein to subjects with one or more inactivating mutations of CDK12. In some embodiments, the method further comprises the step of generating a report that provides results sufficient to select administration of a cell cycle protein inhibitor for subjects with CDK12 mutations.

Additional embodiments are described herein.

DESCRIPTION OF THE FIGURES

(FIG. 1A) Schematic of protein changes in CDK12. (FIG. 1B) Increased frequency of CDK12 loss in metastatic castration-resistant prostate cancer (CRPC) compared to localized disease (Primary). (FIG. 1C) Characteristic pattern of genomic instability found in all cases with CDK12 loss. (FIG 1D) Number of focal copy gains (<8 Mb) by CDK12 mutational status, as determined by whole-exome analysis. (FIG 1E) Size of copy gains (tandem duplications), as ascertained by whole-genome sequencing of index cases with CDK12 mutations (CDK12) and homologous recombination deficiency (HRD).

(FIG. 2A) Mutual exclusivity of CDK12 loss, ETS fusions, mismatch repair deficiency (MMRD), (FIG. 2B) Number of significantly differentially expressed genes (DEGs) for the prostate tumors with different primary genetic drivers. (FIG. 2C) Enrichment plot for signatures of up-(top) and downregulated (bottom) genes in CDK12 mutant tumors. (FIG. 2D) Heatmap of the top DEGs in CDK12-mutant prostate cancer.

FIGS. 3A-C shows that CDK12 loss results in a distinct pattern of genomic instability. (FIG. A) Representative copy-number plots for prostate tumors with deficiencies in key DNA damage response or repair pathways. (FIG. B) Spectrum of copy-number aberrations in tumors with distinct genetic drivers. (FIG. C) Spectrum of inferred mutational signatures in tumors with distinct genetic drivers.

FIGS. 4A-C shows recurrence of focal tandem duplications (FTDs) associated with CDK12 loss. (FIG. 4A) Genome-wide frequency (percentage of CDK12-mutant patients) of FTDs based on a narrow (<2 Mb) and wide (<8 Mb) definition of focality. (FIG. 4B) FTD recurrence and average copy-number gain of FTDs at the individual gene level. Genes with the highest average copy-number are highlighted in red. (FIG. 4C) Delineation of minimal common regions (MCR) for loci with the most recurrent gains specific to CDK12-loss tumors.

FIGS. 5A-F shows signatures of structural variation and neoantigen presentation in CDK12-mutant tumors. (FIG. 5A) Total number of detected gene fusions for prostate tumors with different genetic drivers. (FIG. 5B) Representative examples of circos plots showing the pattern structural variation in tumors with major types of genomic instability. (FIG. 5C) Classification of SVs based on the topology and distance between the breakpoints. adj—breakpoints in adjacent loci, cyt—in same cytoband, arm—on same chromosome arm, gme—genomic translocation, inv—inversion, dup—duplication, del—deletion, tloc—translocation. (FIG. 5D-E) Antigen burden in tumors with distinct types of genetic instability. Overall burden based on single nucleotide variants, insertions/deletions, and fusions is shown in FIG. 5D. Fusion-specific burden is shown in FIG. 5E. (FIG. 5F) Distribution of neoantigens based on genetic variant type and predicted MHC class-I (MHC-I) binding affinity.

FIGS. 6A-E shows immunogenomic properties of CDK12-mutant tumors. (FIG. 6A) Differential expression of MSigDB cancer hallmark gene-sets in CDK12-mutant patients and in LNCaP cells depleted with CDK12 by siRNA. (FIG. 6B) Levels of global immune infiltration across prostate tumors with distinct genetic drivers compared to genetically stable (PGD wild-type) tumors. (FIG. 6C) Overview of T cell clonotypes across CDK12-mutant (n=10), MMRD (n=10), and VT (n=10) tumors. (FIG. 6D) Comparison of clonal expansion between immunogenic (MMRD, CDK12) and wild-type mCRPC tumors (t-test). (FIG. 6E) Immunohistochemistry (IHC) performed on formalin-fixed paraffin-embedded tumor sections using anti-CD3 antibody.

(FIG. 7A) PSA levels of four CDK12-mutant prostate cancer patients treated with anti-PD-1 monotherapy. (FIG. 7B) Representative CD3 IHC images of metastatic lymph node biopsies of patient MO_1975 prior to anti-PD-1 treatment. (FIG. 7C) CT imaging of patient MO_1975 pre- and post-immunotherapy treatment. Arrows indicate metastatic lymph node.

FIGS. 8A-B shows alignment of the kinase domains of CDK12 and CDK subfamily kinases.

(FIG. 10A) Ploidy of tumors associated with distinct primary genetic drivers of prostate cancer. (FIG. 10B) Fusion-gram inferred from structural variants detected by whole-genome sequencing. (FIG. 10C) Density of genes within and outside focal tandem duplications (FTDs). (FIG. 10D) Size of FTDs of example cases of tumors with aberrations in CDK12 and homologous recombination deficiency (HRD). (FIG. 10E) Size of FTDs of tumors with mutant CDK12 or HRD compared with the size of topological domains or replication domains (transitional, early, or late). (FIG. 10F) Distribution of the number of inserted or deleted based at tandem duplication breakpoints.

FIG. 11A-K shows transcriptional characteristics of CDK/2-mutant tumors. (FIG. 11A) Number of differentially expressed genes (DEGs) in prostate tumors with common primary genetic drivers relative to tumors with no aberrations in any of those genes. (FIG. 11B) Volcano plot of DEGs in CDK/2-mutant tumors. (FIG. 11C) Depletion of CDK12 protein expression in LNCaP-CDK12 KD cells. CDK12 was knocked down by siRNA in LNCaP cells. (FIG. 11D) Volcano plot of DEGs in LNCaP-CDK12 KD cells, demonstrating the magnitude and significance of the CDK12 knockdown. (FIG. 11E) Effect of CDK12 knockdown on cell proliferation in LNCaP cells. (FIG. 11F) AR signaling in prostate tumors with common primary genetic drivers. (FIG. 11G) Overlap between top 200 most DEGs for each of the genetic molecular subtypes of prostate cancer. (FIG. 11H) Most significant pathways and signatures from the MSigDB associated with CDK12 loss. (FIG. 11I) Differential expression of genes common to the "Metaplastic Breast dn" and "Mammary Stem Cell dn" signatures from (FIG. 11H). (FIG. 11J) Expression of BRCA1 and BRCA2 across genetic subtypes of prostate cancer is shown. (FIG. 11K) Role of CDK12 in the transcription of long transcripts.

FIGS. 12A-G shows recurrence of CDK/2-associated FTDs (CDK12-FTDs) and effect on expression/upregulation of genes within CDK12-FTDs. (FIGS. 12A-B) Empirical model to call genomic regions with recurrent focal tandem duplications. (FIG. 12B) wide model (peaks <8 Mb). (FIG. 12C) Copy-number aberrations across loci with the most recurrent CDK12-FTDs and all CDK2-mutant mCRPC cases. (FIG. 12D) Genome-wide frequency (percentage of CDK12 wild-type patients) of FTDs based on a narrow (<2 Mb) and wide (<8 Mb) definition of focality. (FIG. 12E) Frequency of CDK12-FTDs at the most recurrent loci in CDK12-mutant and wild-type tumors. (FIG. 12F) Effect of CDK/2-FTDs on the frequency of differential expression. (FIG. 12G) Dose-independent effect of CDK12-FTDs on the frequency of gene expression outliers.

FIGS. 13A-G shows effect of CDK12-FTDS on the expression of select genes. (FIG. 13A) Genes with the highest average copy-number gains in CDK12-mutant tumors. (FIG. 13B) Genes associated with oncogenic signaling pathways (e.g. MAPK, AKT, MTOR). (FIG. 13C) Oncogenic tyrosine kinases. (FIGS. D-G) Schematic diagram of driver gene fusions identified in CDK12-deficient cases. KIAAI549-BRAF fusion is shown in FIG. 13D, HIPK2-BRAF fusion is shown in FIG. 13E, BX117927-ETV1 fusion is shown in FIG. 13F, and AX747630-FGFR2 fusion is shown in FIG. 13G.

(FIG. 14A) Differential expression of chemokines and receptors in CDK12-mutant tumors. (FIG. 14B) Activity score for the most significant immune-related pathways across genetically unstable types of prostate cancer. (FIG. 14C) Measurement of expanded T cell clones using different template cutoffs. (FIG. 14D) RNA-seq and DNA-based (Adaptive) estimation of T cell infiltration in tumors. (FIG. 14E) Number of distinct T cell clones (based on unique CDR3 sequences) from RNA-seq data. (FIG. 14F) Number of T cell receptor CDR3 sequences (counts per million of aligned reads) from RNA-seq data.

DEFINITIONS

Figure 1A:
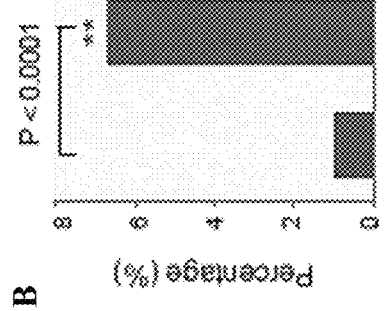
FIGS. 1A-1E shows that biallelic loss of CDK12 is enriched in mCRPC and results in focal tandem duplications.

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of cancer. A subject suspected of having cancer may also have one or more risk factors. A subject suspected of having cancer has generally not been tested for cancer. However, a "subject suspected of having cancer" encompasses an individual who has received a preliminary diagnosis but for whom a confirmatory test has not been done or for whom the level or severity of cancer is not known.

As used herein, the term "subject diagnosed with cancer" refers to a subject who has been tested and found to have cancer. As used herein, the term "initial diagnosis" refers to a test result of initial disease that reveals the presence or absence of disease.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., checkpoint or cell cycle protein inhibitor described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include, but are not limited to, single-stranded and double-stranded compounds, such as, antisense oligonucleotides, siRNAs and shRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases. "Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Oligonucleotide" means a polymer of linked nucleosides each of which can be modified or unmodified, independent one from another.

DETAILED DESCRIPTION OF THE DISCLOSURE

Provided herein are compositions and methods for treating cancer. In particular, provided herein are compositions, methods, and uses of targeted therapy to treat cancer (e.g., prostate cancer) in subjects with CDK12 mutations.

I. Detection of CDK12 Mutations

CDK12 mutations are detected using any suitable method. Exemplary methods are described herein. The present disclosure is not limited to particular detection methods. Examples include, but are not limited to, amplification, hybridization, and sequencing (e.g., next generation or deep sequencing). In some embodiments, detection methods are quantitative.

The present disclosure is not limited to particular CDK12 mutations. In some embodiments, the mutations are in a kinase domain. In some embodiments, the mutations are biallelic or monoallelic. Examples of inactivating CDK12 mutations are described in Example 1 and include, but are not limited to, copy number (e.g., copy number gain or loss), point mutations, truncations, fusions, frameshift mutations, rearrangements, and loss of heterozygosity.

In some embodiments, nucleic acid sequencing methods are utilized for detection. In some embodiments, sequencing methods are a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKeman et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306, 597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732: U.S. Pat. Nos. 6,432,360, 6,485, 944, 6,511,803; herein incorporated by reference in their entireties), the 454 picotiter pyrosequencing technology (Margulies et al., 2005 Nature 437, 376-380: US 20050130173; herein incorporated by reference in their entireties), the Solexa single base addition technology (Bennett et al., 2005, Pharmacogenomics, 6, 373-382; U.S. Pat. No. 6,787,308: U.S. Pat. No. 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714, 330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009: MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In some embodiments, hybridization methods are utilized. Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with radio-, fluorescent- or antigen-labeled bases is localized and quantitated in the tissue using autoradiography, fluorescence microscopy or immunohistochemistry. ISH can also use two or more probes, labeled with radioactivity or the other non-radioactive labels, to simultaneously detect two or more transcripts.

In some embodiments. CDK12 mutations are detected using fluorescence in situ hybridization (FISH). The preferred FISH assays for methods of embodiments of the present disclosure utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

Different kinds of biological assays are called microarrays including, but not limited to: microarrays (e.g., cDNA microarrays and oligonucleotide microarrays); protein microarrays; tissue microarrays; transfection or cell microarrays: chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks: photolithography using dynamic micromirror devices; ink-jet printing; or, electrochemistry on microelectrode arrays.

Southern and Northern blotting may be used to detect specific DNA or RNA sequences, respectively. In these techniques DNA or RNA is extracted from a sample, fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In some embodiments, CDK12 sequences are amplified prior to or simultaneous with detection. Illustrative non-limiting examples of nucleic acid amplification techniques include, but are not limited to, polymerase chain reaction (PCR), transcription-mediated amplification (TMA), ligase chain reaction (LCR), strand displacement amplification (SDA), and nucleic acid sequence based amplification (NASBA).

In some embodiments, quantitative evaluation of the amplification process in real-time is performed. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs, including fluorescence resonance energy transfer (FRET) labels, are disclosed in, for example U.S. Pat. Nos. 6,534,274 and 5,776,782, each of which is herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

Embodiments of the present disclosure further provide solutions, kits and systems comprising reagents for detection of CDK12 mutations (e.g., primer, probes, etc.). In some embodiments, the reagent is selected from, for example, a nucleic acid probe, a sequencing primer, and at least one amplification primers. In some embodiments, the reagents are 10 to 500 (e.g., 12 to 100) nucleotides in length. In some embodiments, kits and systems comprise computer systems for analyzing CDK12 mutation status and providing diagnoses, prognoses, or determining and providing treatment courses of action. In some embodiments, the solution, kit, or system further comprises at least one additional reagent selected from, for example, a buffer, a reverse transcriptase, a polymerase, nucleic acid controls, or a plurality of dNTPs.

In some embodiments, a computer-based analysis program is used to translate the raw data generated by the detection assay (e.g., CDK12 mutations) into data of predictive value for a clinician. The clinician can access the predictive data using any suitable means. Thus, in some preferred embodiments, the present disclosure provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., a blood or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced (e.g., CDK12 mutations status) specific for the diagnostic or prognostic information desired for the subject.

The profile data is then prepared in a format suitable for interpretation by a treating clinician. For example, rather than providing raw data, the prepared format may represent a diagnosis or risk assessment (e.g., CDK12 mutation status) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

II. Treatment Methods

As described above, in some embodiments, the CDK12 mutation status of a prostate cancer sample from an individual with prostate cancer (e.g., metastatic castration-resistant prostate cancer) is used to determine a treatment for prostate cancer. For example, in some embodiments, the present disclosure provides a method of treating cancer, comprising administering a checkpoint inhibitor (e.g., PD-1) or cell cycle inhibitor (e.g., CCND1, CCND2, CCND3, CCNE1, or CDK4) to subjects that have CDK12 mutations (e.g., inactivating CDK12 mutations). In some embodiments, the presence of CDK12 mutations in a prostate cancer sample is indicative of increased survival of the subject when the subject is treated with a checkpoint inhibitor. In some embodiments, subjects that do not have CDK12 mutations are not administered a checkpoint inhibitor and are instead administered a different treatment.

In some embodiments, the checkpoint inhibitor is selected from, for example, a nucleic acid (e.g., siRNA, shRNA, miRNA or an antisense nucleic acid), a small molecule, a peptide, or an antibody. In some embodiments, checkpoint therapy targets PD-1 or PD-L 1.

In some embodiments, the inhibitor targets PD-1. In some embodiments, the inhibitor is one or more of pembrolizumab (Merck Kenilworth, N.J.; U.S. Pat. No. 8,952,136; herein incorporated by reference in its entirety), nivolumab (Bristol-Myers Squibb, New York, N.Y.; U.S. Pat. No. 7,595,048; herein incorporated by reference in its entirety), cemiplimab (Regeneron, Tarrytown, N.Y.), MED10680 (AMP-514, GlaxoSmithKline, Brentford, United Kingdom). CT-001, pidilizumab (Cure Tech, Yavne, Israel), AMP-224 (GlaxoSmithKline, Brentford, United Kingdom) or PDR001 (Novartis, Basel, Switzerland).

In some embodiments, the inhibitor targets a cell cycle protein. Examples include, but are not limited to, cyclin D1 (CCND1), cyclin D2 (CCND2), cyclin D3 (CCND3), cyclin E1 (CCNE), and cyclin dependent kinase 4 (CDK4). Examples of inhibitors of cell cycle proteins include, but are not limited to, indirubin, LY2835219, arcyriaflavin A, NSC 625987, CDK4 inhibitor, fascaplysin, alvocidib, PHA-793887, P276-00, AT7519, SU9516, BMS-265246, SNS-032, PD 0332991 hydrochloride, and R547. Such inhibitors are commercially available (e.g., from Santa Cruz Biotechnology (Dallas, Tex.) or Selleckchem (Houston, Tex.)).

In some embodiments, the checkpoint inhibitor is a nucleic acid (e.g., a nucleic acid that targets PD-1 or cell cycle proteins). Exemplary nucleic acids suitable for inhibiting PD-1 or cell cycle proteins (e.g., by preventing expression of PD-1 or cell cycle proteins) include, but are not limited to, antisense nucleic acids and RNAi molecules. In some embodiments, nucleic acid therapies are complementary to and hybridize to at least a portion (e.g., at least 5, 8, 10, 11, 12, 13, 14, 15, 16, 17, 18, 19, or 20 nucleotides) of PD-1 or cell cycle proteins.

In some embodiments, compositions comprising oligomeric antisense compounds, particularly oligonucleotides are used to modulate the function of nucleic acid molecules encoding PD-1 or cell cycle proteins, ultimately modulating the amount of PD-1 or cell cycle proteins expressed. This is accomplished by providing antisense compounds that specifically hybridize with one or more nucleic acids encoding PD-1 or cell cycle proteins. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of PD-1 proteins or cell cycle proteins in the cell.

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include f-D-ribonucleosides, .beta.-D- deoxyribonucleosides, 2'-modified nucleosides (such 2'-modified nucleosides may include 2'-MOE and 2-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments. "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound has a gapmer motif in which the gap consists of 6, 7, 8, 9, 10, 11, 12, 13, 14, 15, or 16 linked nucleosides.

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$, wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type.

In certain embodiments, oligonucleotides having such an alternating motif also comprise a modified 5' terminal nucleoside, such as those of formula IIc or IIe.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Additional modifications are described, for example, in U.S. Pat. No. 9,796,976, herein incorporated by reference in its entirety.

In some embodiments, nucleic acids are RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, PD-1 or cell cycle proteins.

An "RNA duplex" refers to the structure formed by the complementary pairing between two regions of a RNA molecule. The RNA using in RNAi is "targeted" to a gene in that the nucleotide sequence of the duplex portion of the RNAi is complementary to a nucleotide sequence of the targeted gene. In certain embodiments, the RNAi is are targeted to the sequence encoding PD-1 or cell cycle proteins. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides, shRNAs are exported from the nucleus by Exportin-5, and once in the cytoplasm, arc processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter. The nucleic acid sequence can also include a polyadenylation signal. In some embodiments, the polyadenylation signal is a synthetic minimal polyad n certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of PD-1 or a cell cycle protein.

In some embodiments, hybridization occurs between an antisense compound disclosed herein and a PD-1 or cell cycle protein nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an PD-1 nucleic acid or nucleic acid encoding a cell cycle proteins).

Non-complementary nucleobases between an antisense compound and a PD-1 nucleic acid or nucleic acid encoding a cell cycle protein be tolerated provided that the antisense compound remains able to specifically hybridize to a target nucleic acid. Moreover, an antisense compound may hybridize over one or more segments of an PD-1 or cell cycle protein nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87/o, 88%, 89%, 90%, 91%, 92%, 93%, 94%, 95%, 96%, 97%, 98%, 99%, or 100% complementary to an PD-1 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present disclosure. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Alnc1 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an PD-1 or cell cycle protein nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Alnc1 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. In certain embodiments, the antisense compounds are complementary to at least an 18 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

In some embodiments, candidate PD-1 or cell cycle protein inhibitors are screened for activity (e.g., using the methods described herein or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer: intratracheal, intranasal, epidermal and transdermal), oral or parenteral. Parenteral administration includes intravenous, intraarterial, subcutaneous, intraperitoneal or intramuscular injection or infusion: or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

In some embodiments, additional cancer treatments are provided to a subject. Various classes of antineoplastic (e.g., anticancer) agents are contemplated for use in certain embodiments of the present disclosure. Anticancer agents suitable for use with embodiments of the present disclosure include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of embodiments of the present disclosure include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.: 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.): 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.): 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques: 15) tumor vaccines; 16) therapies directed against tumor metastases (e.g., batimastat, etc.): 17) angiogenesis inhibitors: 18) proteosome inhibitors (e.g., VELCADE) or ubiquitination or neddylation inhibitors; 19) inhibitors of acetylation and/or methylation (e.g., HDAC inhibitors)) and inhibitors of bromodomain containing proteins (e.g. BET-BRD inhibitors), 20) modulators of NF kappa B; 21) inhibitors of cell cycle regulation (e.g., CDK inhibitors), 22) modulators of p53 protein function; 22) bromodomain inhibitors, and 24) radiation.

Any oncolytic agent that is routinely used in a cancer therapy context finds use in the compositions and methods of embodiments of the present disclosure. For example, the U.S. Food and Drug Administration maintains a formulary of oncolytic agents approved for use in the United States. International counterpart agencies to the U.S.F.D.A. maintain similar formularies. The below Table provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Ceil Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |

| | | |
|---|---|---|
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequs Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Phamiacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant | Faslodex | IPR Pharmaceuticals, |

| | | |
|---|---|---|
| (7-alpha-[9-(4,4,5,5,5-penta fluoropentylsulphinyl) nonyl]estra-1,3,5-(10)-triene-3,17-beta-diol) | | Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$, Azgly$^{10}$]LHRH; pyro-Glu-His-Trp-Ser-Tyr-D-Ser(But)-Leu-Arg-Pro-Azgly-NH2 acetate $[C_{59}H_{84}N_{18}O_{14} \cdot (C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((—)-(S)-2,3,5,6-tetrahydro-6-phenylimidazo [2,1-b] thiazole monohydrochloride (1,4-dihydroxy-5,8-bis[[2-[(2-hydroxyethyl)amino]ethyl]amino]-9,10-anthracenedione dihydrochloride) | Ergamisol | Janssen Research Foundation, Titusville, NJ |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R,3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |

| | | |
|---|---|---|
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo [5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa, anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |

-continued

| | | |
|---|---|---|
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

EXPERIMENTAL

The following examples are provided in order to demonstrate and further illustrate certain preferred embodiments and aspects of the present disclosure and are not to be construed as limiting the scope thereof.

Example 1

Methods
Cell Lines

LNCaP (male, prostate carcinoma) and HeLaS3 (female, cervical adenocarcinoma) cell lines were obtained from the American Type Culture Collection. LNCaP cells were cultured in RPMI1640 medium, and HeLaS3 cells were cultured in Ham's F-12K medium, both supplemented with 10% fetal bovine serum (FBS; Invitrogen) and 1% penicillin/streptomycin (Invitrogen). Cell lines were maintained at 37° C. in a 5% $CO_2$ cell culture incubator. Cell lines were genotyped to confirm their identity at the University of Michigan Sequencing Core and tested routinely for Mycoplasma contamination.

Human Subjects and Patient Inclusion

Sequencing of clinical samples was approved by the Institutional Review Board of the University of Michigan (Michigan Oncology Sequencing Protocol, MI-ONCOSEQ, IRB #HUM00046018, HUM00067928, HUM00056496). Patients with clinical evidence of metastatic castration-resistant prostate cancer (mCRPC) that could be feasibly accessed by image-guided biopsy were eligible for inclusion. Consecutive cases from SU2C, mCRPC enrolled in Mi-Oncoseq, and the University of Michigan rapid autopsy series, with at least 25% tumor content as determined by post-sequencing analysis of zygosity shift and copy-number adjusted variant allele fraction using the Mi-Oncoseq clinical analysis pipeline, were included in this study (see Table 1 for source cohort).

Kinase Domain Alignment

Alignment of the kinase domains of 30 members of the human CDK and MAPK families of protein kinases were performed using BLASTp followed by visualizations using NCBI Multiple Sequence Alignment Viewer 1.6.0 with no master sequence set. Amino acid residues were shaded by conservation using NCBI Multiple Sequence Alignment Viewer 1.6.0 using frequency based differences, with highly conserved residues shaded red, moderately conserved residues shaded blue, and nonconserved residues shaded gray (www.ncbi.nlm.nih.gov/projects/msaviewer/#).

CDK12 Disruption by CRISPR-Cas9

CDK12 knockout by CRISPR-Cas9 system was performed in two cell lines: LNCaP and HeLaS3. The human CDK12 eDNA sequence (NM_016507) was loaded onto the Genome-Engineering website (tools.genome-engineering.org) for the prediction of gRNAs for intended targeting sequences. Five gRNAs targeting the N-terminus and kinase domain of CDK12 were synthesized and cloned into LentiCRISPRv2 vector (with Cas9). The efficiency and selectivity of the synthesized gRNAs were tested in a reporter plasmid, pCAG-EGxxFP (Addgene), within which a specific gRNA-targeted sequence was inserted in the middle of EGFP. A valid gRNA will facilitate EGFP reconstitution through CRISPR-Cas9-mediated double strand break followed by homologous recombination. For clonal expansion, single puromycin-resistant colonies were picked and expanded. Genomic DNA and protein lysate were prepared for the analysis of CDK12 sequence and CDK12 protein expression by Sanger sequencing and Western blot analysis, respectively, gRNA1,
AGGGAGAACGACGAACGTCG;

gRNA2,
GGAATGACGACTGCGTGAAC;

gRNA3,
AACACTTAATATCCCGATGC;

gRNA4,
CAAATCAAACTAGCAGATTT;

gRNA5,
GGCTCTATAACTCTGAAGAG.

siRNA-Mediated Knockdown of CDK12

For the CDK12 knockdown experiment, a pooled ON-TARGETplus siRNA targeting CDK12 (Dharmacon/GE Healthcare) was transfected into LNCaP cells using Oligofectamine (Life Sciences). To ensure an efficient knockdown of CDK12, cells were transfected again with the same siRNA 48 hours later (48-hr time point), and incubated for another 24 hours (72-hr time point). Scrambled siRNA was used as a negative control (ON-TARGETpus Non-targeting Pool, Dharmacon/GE Healthcare). For CDK12 protein detection, cells were lysed in RIPA buffer containing protease inhibitor cocktail (Pierce). Expression of CDK12 protein was measured by Western blotting using anti-CDK12 antibody (Cell Signaling). For the cell proliferation assay, LNCaP cells were trypsinized 72 hours post-transfection, and plated in triplicate in 24-well plates. The cells were incubated at 37° C. and 5% $CO_2$ atmosphere using the IncuCyte live-cell imaging system (Essen Biosciences). Cell proliferation was assessed by kinetic imaging confluence measurements at 3-hour time intervals.

Immunostaining of T Lymphocytes

Immunohistochemistry (IHC) was performed on formalin-fixed paraffin-embedded tumor tissue sections using CONFIRM anti-CD3 (2GV6) rabbit monoclonal antibody (Ventana Medical Systems). IHC was carried out using an automated protocol developed for the Benchmark XT automated slide staining system and detected using the UltraView Universal DAB detection kit (Ventana Medical Systems). Hematoxylin II (Ventana-Roche) was used as counterstain. Human tonsil sections were used as the positive control. CD3-positive T lymphocytes exhibited membranous and cytoplasmic staining.

Integrative Clinical Sequencing

Integrative clinical sequencing was performed using standard protocols in a Clinical Laboratory Improvement Amendments (CLIA) compliant sequencing lab (Robinson et al., 2015; Robinson et al., 2017). In brief, tumor genomic DNA and total RNA were purified from the same sample using the AllPrep DNA/RNA/miRNA kit (Qiagen). Matched normal genomic DNA from blood, buccal swab, or saliva was isolated using the DNeasy Blood & Tissue Kit (Qiagen). RNA sequencing was performed by exome-capture transcriptome platform (Cieslik et al., 2015). Exome libraries of matched pairs of tumor/normal DNAs were prepared as described before (Robinson et al., 2015: Robinson et al., 2017), using the Agilent SureSelect Human All Exon v4 platform (Agilent). All the samples were sequenced on the Illumina HiSeq 2000 or HiSeq 2500 (Illumina Inc) in paired-end mode. The primary base call files were converted into FASTQ sequence files using the bcl2fastq converter tool bcl2fastq-1.8.4 in the CASAVA 1.8 pipeline.

T-Cell Receptor β Repertoire Deep Sequencing

Amplification and sequencing of [TCRB/IGH/IGKL/TCRAD/TCRG] CDR3 was performed using the immunoSEQ Platform (Adaptive Biotechnologies). Same DNA aliquot obtained from frozen tumor tissues was used as for the exome sequencing. The immunoSEQ Platform combines multiplex PCR with high throughput sequencing and a sophisticated bioinformatics pipeline for [TCRB/IGH/IGKL/TCRAD/TCRG] CDR3 analysis that includes internal PCR amplification controls. PCR reactions were performed on 60 mCRPC tumor samples with 2 µg of DNA, and PCR fragments were sequenced on the Illumina MiSeq. Computational analysis of sequencing data, including the estimation of the total number of templates, identification, and clonotypes was performed using the vendor-supplied analysis portal.

Whole-Genome Sequencing Data Analysis

The bcbio-nextgen pipeline version 1.0.3 was used for the initial steps of tumor whole-genome data analysis. Paired-end reads were aligned to the GRCh38 reference using BWA (bcbio default settings), and structural variant calling was done using LUMPY (Layer et al., 2014) (bcbio default settings), with the following post-filtering criteria: "(SR>=1 & PE>=1 & SU>=7) & (abs(SVLEN)>5e4) & DP<1000 & FILTER="PASS"". The following settings were chosen to minimize the number of expected germline variants: (FDR<0.05 for germline status for both deletions and duplications). Replication domain sizes for normal tissues were obtained from GSE53984, and transactivation domain sizes for prostate cancer cell lines were obtained from GSE73782.

Exome Data Analysis

The FASTQ sequence files from whole exome libraries were processed through an in-house pipeline constructed for analysis of paired tumor/normal data. The sequencing reads were aligned to the GRCh37 reference genome using Novoalign (version 3.02.08) (Novocraft) and converted into BAM files using SAMtools (version 0.1.19). Sorting, indexing, and duplicate marking of BAM files used Novosort (version 1.03.02). Mutation analysis was performed using freebayes (version 1.0.1) and pindel (version 0.2.5b9). Variants were annotated to RefSeq (via the UCSC genome browser, retrieved on Aug. 22, 2016), as well as COSMIC v79, dbSNP v146, ExAC v0.3, and 1000 Genomes phase 3 databases using snpEff and snpSift (version 4.1g). SNVs and indels were called as somatic if they were present with at least 6 variant reads and 5% allelic fraction in the tumor sample, and present at no more than 2% allelic fraction in the normal sample with at least 20× coverage; additionally, the ratio of variant allelic fractions between tumor and normal samples was required to be at least six in order to avoid sequencing and alignment artifacts at low allelic fractions. Minimum thresholds were increased for indels observed to be recurrent across a pool of hundreds of platform- and protocol-matched normal samples. Specifically, for each such indel, a logistic regression model was used to model variant and total read counts across the normal pool using PCR duplication rate as a covariate, and the results of this model were used to estimate a predicted number of variant reads (and therefore allelic fraction) for this indel in the sample of interest, treating the total observed coverage at this genomic position as fixed. The variant read count and allelic fraction thresholds were increased by these respective predicted values. This filter eliminates most recurrent indel artifacts without affecting our ability to detect variants in homopolymer regions from tumors exhibiting microsatellite instability. Germline variants were called using ten variant reads and 20% allelic fraction as minimum thresholds, and were classified as rare if they had less than 1% observed population frequency in both the 1000 Genomes and ExAC databases.

Exome data was analyzed for copy number aberrations and loss of heterozygosity by jointly segmenting B-allele frequencies and log 2-transformed tumor/normal coverage ratios across targeted regions using the DNAcopy (version 1.48.0) implementation of the Circular Binary Segmentation algorithm. The Expectation-Maximization Algorithm was used to jointly estimate tumor purity and classify regions by copy number status. Additive adjustments were made to the log 2-transformed coverage ratios to allow for the possibility of non-diploid tumor genomes; the adjustment resulting in the best fit to the data using minimum mean-squared error was chosen automatically and manually overridden if necessary.

Assignment of Pathway Status

Figure 2A:
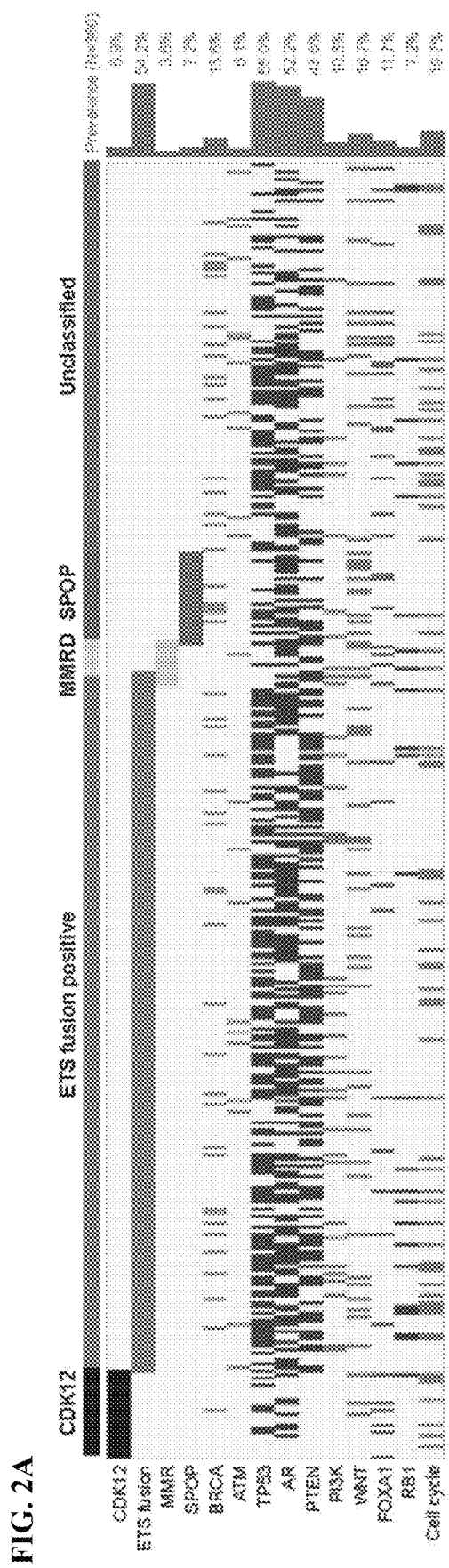
FIGS. 2A-D shows that CDK12-mutant prostate cancer is a novel molecular subtype of mCRPC.

For pathway status depicted in FIG. 2A, the following criteria were applied: (1) TPS3, RB1, PTEN, and ATM cases with biallelic inactivation by mutation, copy loss, copy neutral LOH, gene fusion or known pathogenic germline allele were scored as mutant for that pathway; (2) For BRCA pathway, biallelic inactivations of BRCA2, BRCA1, PALB2, or RAD51B/C were scored as mutant; (3) For PI3K pathway activation, activating mutations or amplifications of PIK3CA, PIK3CB, truncating or iSH2 mutations in PIK3RJ, or known activating mutations in AKT1 were included; (4)

For WNT pathway activation, biallelic inactivation of APC, ZNRF3, or RNF43, recurrent activating mutations of CTNNB1, or fusions and overexpression of RSPO family ligands were included; (5) For cell cycle aberrations, amplifications of CCND1, CCND2, CCND3, CCNE1, and CDK4, or biallelic inactivations of RB1, CDKN2A, CDKN1B, and CDKN2C were included. For all genes, amplification was defined as an absolute copy-number of seven or more.

RNA-Seq Data Analysis

RNA-seq data processing, including quality control, read trimming, alignment, and expression quantification by read counting, was carried out as described previously (Robinson et al., 2017), using the clinical RNA-seq pipeline "CRISP" (available at https://github.com/mctp/rnascape-bootstrap) and our toolkit for the comprehensive detection of chimeric RNAs "CODAC" (available at https://github.com/mctp/codac). Both pipelines were run with default settings for paired-end RNA-seq data of at least 75 bp. The only changes were made for unstranded transcriptome libraries sequenced at the Broad Institute, for which quantification using "featureCounts" (Liao et al., 2014) was used in unstranded mode "-s0". Briefly, three separate alignment passes (STAR 2.4.0g1) against the GRCh38 (hg38) reference with known splice-junctions provided by the (Gencode 27) are made for the purposes of expression quantification and fusion discovery. The first pass is a standard paired-end alignment followed by gene expression quantification. The second and third pass are for the purpose of gene fusion discovery and enable STAR's chimeric alignment mode (chimSegmentMin: 10, chimJunctionOverhangMin: 1, alignIntronMax: 150000, chimScoreMin: 1). Fusion detection was also carried out using CODAC with default parameters to balance sensitivity and specificity (annotation preset:balanced). CODAC uses MOTR v2 a custom reference transcriptome based on a subset of Gencode 27. Fusion-Grams were prepared using CODAC (v 3.2.2) based on its standard prediction of topology (inversion, duplication, deletion, translocation), and distance (adjacent—breakpoints in two directly adjacent loci, cytoband—breakpoints within the same cytoband based on UCSC genome browser, arm—breakpoints within the same chromosome arm).

Differential Expression Analysis

All differential expression analyses were done using limma R-package (Smyth, 2005), with the default settings for the "voom" (Law et al., 2014), "lmFit" "eBayes", and "topTable" functions. The contrasts were designed as follows. First, a set of "all wild-type" samples were identified. These samples were wild-type (WT) for mutations in all primary genetic drivers (PGDs) of prostate cancer, i.e. ETS fusions, homologous recombination deficiency (BRCA1/2, PALB2, etc.), AIM mutations, mismatch repair deficiency, SPOP mutations, and CDK12 mutations. These samples were formed a baseline to which all other groups were compared. Next, separate design matrices were constructed with coefficients for each of the primary genetic drivers, in addition to coefficients for TP53 status, different biopsy sites (bone marrow, lymph node, soft tissue), and type of RNA-seq library (capture RNA-seq vs polyA RNA-seq). For example, CDK12-mutant samples were contrasted with the wild-type samples, with separate coefficients for TP53 status, library type, etc. This allowed one to estimate the log fold-changes and adjusted p-values associated with each of the genetic drivers and some of the confounding variables (technical i.e. library type, and biological e.g. biopsy site, TP53 mutation status). Liver biopsies were excluded from this analysis because of the large variability in the expression of liver-specific genes in these biopsies. These estimated moderated log fold-changes and adjusted (FDR) p-values were used in all of the other downstream analyses.

Figure 2B:
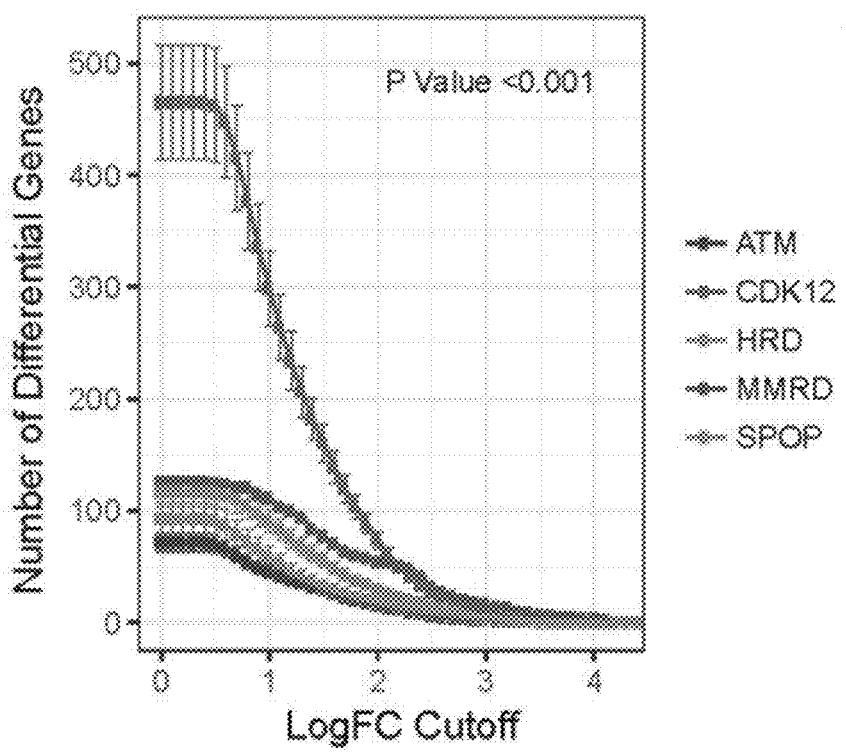

To estimate the number of differentially expressed genes (DEGs) associated with each PGD (FIG. 2B), corrections were made for the fact that different statistical power was available to detect those differences for different groups, since the number of samples are much higher among certain groups, e.g. for ETS-positive prostate cancer than for SPOP-mutant prostate cancer. Hence, a sampling approach where a random set of 13 samples (equal to the size of the smallest category, mismatch repair-deficient) was selected and differential expression analysis was performed as described before. This analysis was repeated 32 times to generate estimates of the average number of DEGs. The number of DEGs was plotted, given a fixed p-value, as a function of absolute log FC cutoff.

Pathway and Gene Set Enrichment Analyses

Figure 11C:
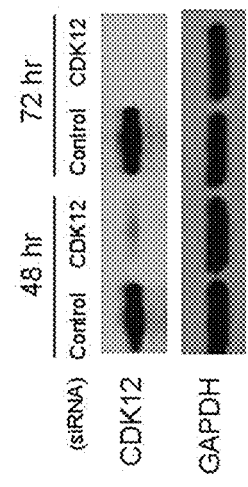

All enrichment analyses have been carried out using the Random-Set approach (Newton et al., 2007) using the shrunken log fold changes estimated above. Gene signatures were obtained from the MSigDB (Liberzon et al., 2015), and the collection of pathway gene sets curated by SABiosciences (SABiosciences—a QIAGEN company, Oct. 17 2017). Identifiers (entrez gene ids, gene symbols) were mapped onto Ensemble gene_id's using Bioconductor and biomaRt (Durinck et al., 2005). If necessary, outdated gene symbols were corrected using HGNChelper (Waldron and Riester, 2017). The AR signaling score (FIG. 11F) was computed using the signature by Beltran et al. (Beltran et al., 2016). Briefly, gene expression levels were converted into percentiles across the whole cohort. These percentiles were transformed using the quantile function for the normal distribution "qnorm" in R. For each sample these "inverse-normal" scores were summed to obtain the raw AR signaling score. Given that expression of AR targets strongly depends on tumor content, a linear model (R: lm) was constructed with tumor contents as a covariate and the raw score as a dependent variable. The final "AR signaling scores" were computed as the residual i.e. "raw score—predicted". The cohort MImmScore is the cohort-level generalization of the MImmScore, as described previously (Robinson et al., 2017). It is based on the same set of immune system-related genes, but rather than scoring the immunological activity of one sample versus all other samples (MImmScore), it scores the immunological activity in one cohort vs. the WT cohort (as described above). The moderated fold-changes (see section: Differential expression analysis) and the Yoshihara et al. gene set are used as input to the Random-Set method (Yoshihara et al., 2013). The resulting Z-scores and adjusted p-values are shown in FIG. 6B. Hallmark (FIG. 6A) and immune pathway analyses (FIG. 11B) were based on the Hallmark sets from MsigDB and the SABiosciences gene sets. For FIG. 11B, activity scores were computed as "Z-score*-log 10(p-value)" based on the Z-scores and p-values from the Random-Set method. The intersection of genes in the LIEN_BREAST_CARCINOMA_METAPLASTIC_VS_DUCTAL_DN and LIM_MAMMARY_STEM_CELL_DN signatures was designated as "Stem and Metaplastic dn" in FIG. 11I.

Mutation Signature Analysis

Mutation signature analysis was performed by interpreting the set of somatic mutations in the context of 30 known mutational signatures from the COSMIC database (http://cancer.sanger.ac.uk/cosmic/signatures). The empirical distribution of the set of trinucleotide changes around somatic single nucleotide variants was extracted for each sample using the Bioconductor SomaticSignatures package, version 2.10.0 (Gehring et al., 2015). The R package quadprog, version 1.5-5 (Turlach and Weingessel, 2013), was then used to estimate a set of 30 non-negative weights each representing the contribution of a known COSMIC signature to the observed set of trinucleotide changes. Results were visualized using the plotMutationSpectrum function from the SomaticSignatures package.

CDK12 Mutation Frequeny Analysis

Using estimates of 2.3 Mutations/Mb in CRPC and 0.95 Mutations/Mb in localized tumors (determined from cohorts sequenced and analyzed uniformly here), the rate of CDK12 mutations was expected to increase by about 2.5-fold in CRPC. Using an empirical distribution of mutation rates for 277 localized prostate tumors, scaled to a median of 2.3 Mutations/Mb to reflect this increase, sampling with replacement from this distribution was performed 498 times (the size of the localized cohort), and a number of mutations from the CDK12 locus (0.0045 Mb) were stimulated using a Poisson distribution and the number of samples was computed with one or two simulated CDK12 mutations. Across 1000 such iterations, a mean of 6 samples with single mutations in CDK12 and 0.06 samples with two or more mutations in CDK12 was found; the maximum number of samples with two or more mutations in CDK12 across the 1000 simulations was 1. Therefore, even if the mutation rate in the localized cohort was inflated to reflect the observed mutation rate in CRPC, one would expect at most 1/498 (0.2%) extra double hits, far less than the difference observed between localized and CRPC samples.

CDK12-FTD Recurrence Analysis

To identify regions recurrently amplified in CDK12-mutant cases, a random model was developed to estimate number of peaks at any genomic region controlling for differences in gene density (since the copy-number calls are based on whole-exome sequencing data). First, the sizes of all copy gains relative to the baseline copy-number were determined; these events included all regions with three+ copies and regions with two copies on X. Next, all CNVs were filtered for focal tandem duplications (FTDs) using a narrow (<2 Mb) and wide (<10 Mb) cutoff, resulting in two separate sets of FTDs in each sample. Two independent null models (background models) based on the two sets of FTDs (the narrow and the wider FTDs) in both the CDK12-mutant and CDK12-wild-type sets of cases were developed. The overall statistical procedure was to: 1) sample random peaks (generate the same number of peaks as in any of the four input sets (narrow CDK12-wt, narrow CDK12-mut, wide CDK12-wt, wide CDK12-mut)—if a peak overlapped a region that is not covered by the capture kit, it was randomized again: 2) compute coverage at all loci in the genome; 3) compute how many loci are covered by more than a given number of random peaks. This procedure was repeated 800 times for each of the four sets of peaks. This allowed one to determine what the average (across all 800 randomization) number of loci was which were covered by a least given number of peaks, i.e. the expected number of false-positive calls. Based on these models, cutoffs (the minimum number of peaks) that define a region as significant based on a pre-defined empirical false-discovery rate (the expected proportion of false-positive calls among all calls) were determined. Finally, regions exceeding the predefined threshold were merged into a contiguous peak based on a distance threshold of 1 Mb. Regions significant in the CDK12-mutant cases (i.e. narrow CDK12-mut, wide CDK12-mut) were also subsequently merged to define a final set of loci with recurrent (narrow or wide) gains in CDK12-mutant cases.

Copy-Number Expression Aggregation

When aggregating copy-number and expression at the gene level, 100 kb windows centered around the canonical promoter were defined for each gene. Those promoter regions were overlapped with the copy-number segments and each gene was assigned to exactly one segment. If a promoter region overlapped multiple segments, the one with the higher copy-number was chosen. To analyze expression differences in each sample, a strategy very similar to the one above (Differential expression analysis section) was followed. Each individual CDK12-mutant sample was contrasted with the all-wild-type group; therefore, for each gene in each sample, a shrunken log fold change was computed (relative to the all-wild-type group) and p-value (based on the variance estimate in the all-wild-type group). The following thresholds were used to compute the number of genes meeting differential expression criteria: Differentially Expressed Gene: Nominal p-value <0.1. Outlier Expressed Gene: p-value <1e-3 and log fold change >3.322 and RPKM >4 and percentile >0.95.

Structural Variant and Fusion-Gram Analysis

Fusion-grams were plotted using data directly from the CODAC chimeric RNA discovery pipeline (see above), which includes gene-gene fusions as well as a number of types of truncating gene fusions. All of these events were categorized into broad classes of likely duplications, deletions, inversions, and translocations, based on the topology of their breakpoints, and also based on the distance between the breakpoints from GRCh38 cytobands and loci adjacency. To compute a fusion-gram, the frequency of events within a given class combination (distance×topology) was determined relative to the total number of events across all samples of a genetic subtype (e.g. CDK12-mutant cases). Similarly, to create fusion circos plots, the CODAC variants were color coded based on the inferred topology of the breakpoints. To create circos plots that are representative both in terms of the number of structural variants and their topology within each genetic class, all of the structural variants across all cases within a group were combined, followed by sampling a random set of structural variants proportional to their average number.

HLA-Typing Analysis

PHLAT (Version 1.0) was used to determine the HLA haplotype of individuals for MHCI (HLA-A, HLA-B, HLA-C) at four-digit resolution using exome sequencing data from the patient's matched normal sample.

Integrative in Silico Neoantigen Translation

Mutation analysis from exome sequencing of patient's matched tumor and normal pair along with fusion analysis from patient's transcriptome sequencing was carried out. Somatic mutations from single/dinucleotide variants as well as small insertion/deletions from the cohort were used to identify the specific amino acid coding change. Missense mutations with >1 RPKM expression were selected and processed using Annovar (Version 07.16.17) and in-house perl script to get 17-mer amino acid neopeptides. Mutations with start-loss, stop-gain, and splice sites were excluded from the analysis. Indels and fusions with >IRPKM expression were selected. Inframe, indel, and fusion neopeptides of 17-mer length were created in the similar way as missense mutations. Frameshifts, indels, and fusions create novel open reading frames producing several neoantigenic peptides that are highly distinct from self. These frameshift peptides were generated until a stop codon was hit, or we reached the read evidence. Neopeptides created from indels and fusions with length less than 9-mer or with an immediate stop codon were excluded from further analysis.

IEDB Peptide Binding Prediction

All of the neopeptides from single mutations, dinucleotides, small insertion/deletions, and fusions were than used to assess MHCI binding using the IEDB_recommended parameter from Immune Epitope Database (IEDB) (Version IEDB_MHC-2.17) and predicted high affinity MHCI binding neopeptide against patient autologous haplotypes. All neopeptides with an IEDB percentile rank <2 were considered as high affinity binding epitopes.

T Cell Repertoire Analysis from RNA-Seq Data

Figure 11B:
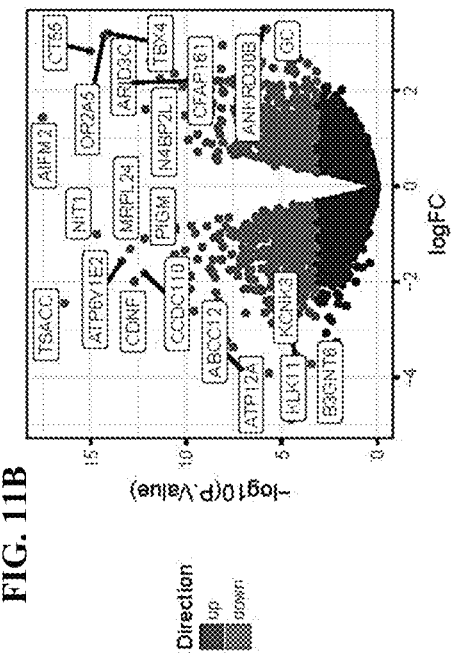
Figure 11A:
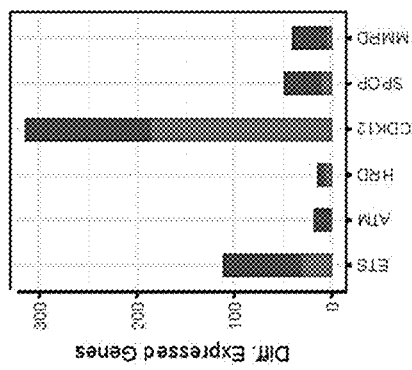
Figure 11F:
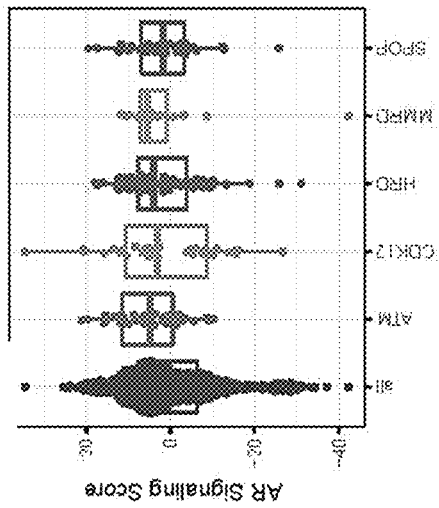
Figure 11E:
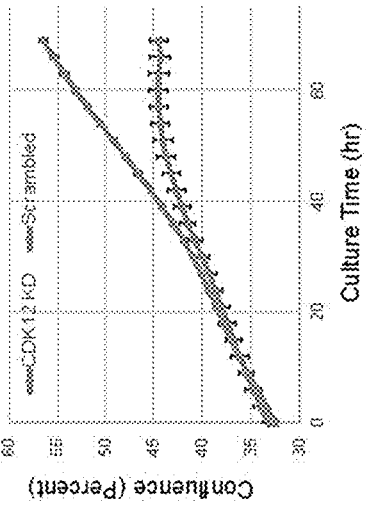
Figure 11D:
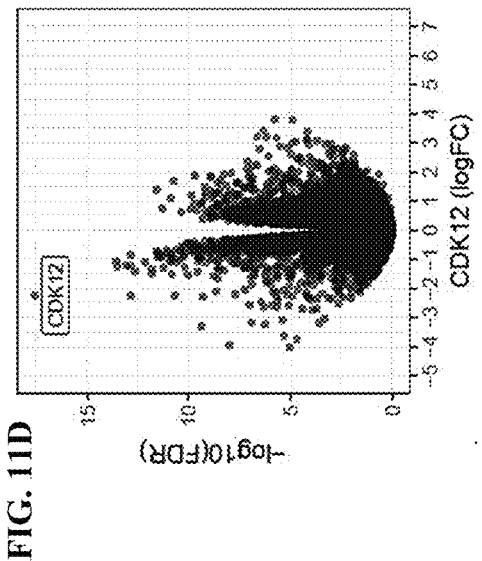

Repertoire analysis was carried out using MiXCR (Bolotin et al., 2015) using the recommended workflow and setting for RNA-seq data. i.e. "-g -s hsa -p ma-seq -OallowPartialAlignments=true", and two rounds of "assemblePartial" followed by "extendAlignments" and "assemble". MiXCR was run on all unmapped reads, paired-end reads mapped to the T cell receptor loci. The number of reads mapped to the T cell receptor loci and normalized to the number of aligned reads and the number of different CDR3 sequences were used as the TCR CDR3 cpms and TCR clones. To verify the accuracy of this approach, the RNA-based estimates were compared to TCRb DNA-based sequencing and found them in excellent agreement (FIG. 11D).

Statistical Analysis

Figure 1B:
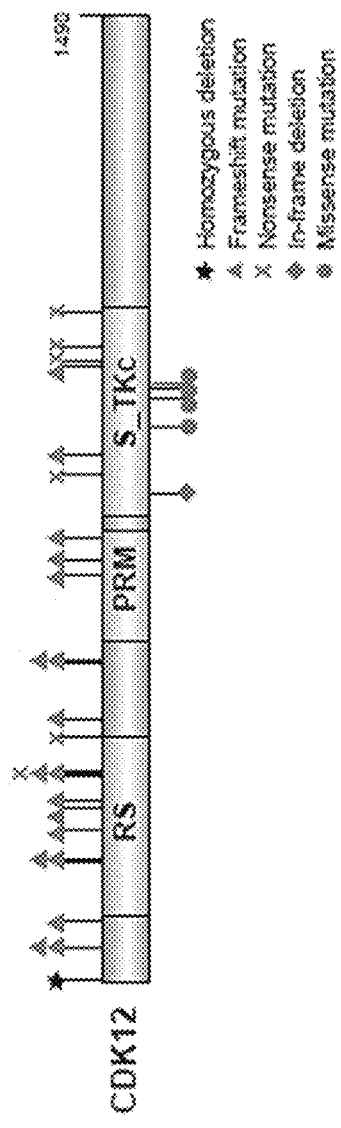

Fisher exact tests were performed for CDK12 mutation incidence in CRPC vs. primary prostate cancer in the Results section and FIG. 1B; n=360 for CRPC and n=498 for primary tumors. Fisher exact tests were performed for CDK/2 mutation status vs. PTEN mutation status and CDK12 incidence vs. ETS fusion status in the Results section; n=360. A t-test was used to evaluate expanded T cell clone values in differing subclasses of CRPC in FIG. 6D; n=10 for each subclass.

Results

CDK12 Mutations are Enriched in Cases of mCRPC

Figure 8A:
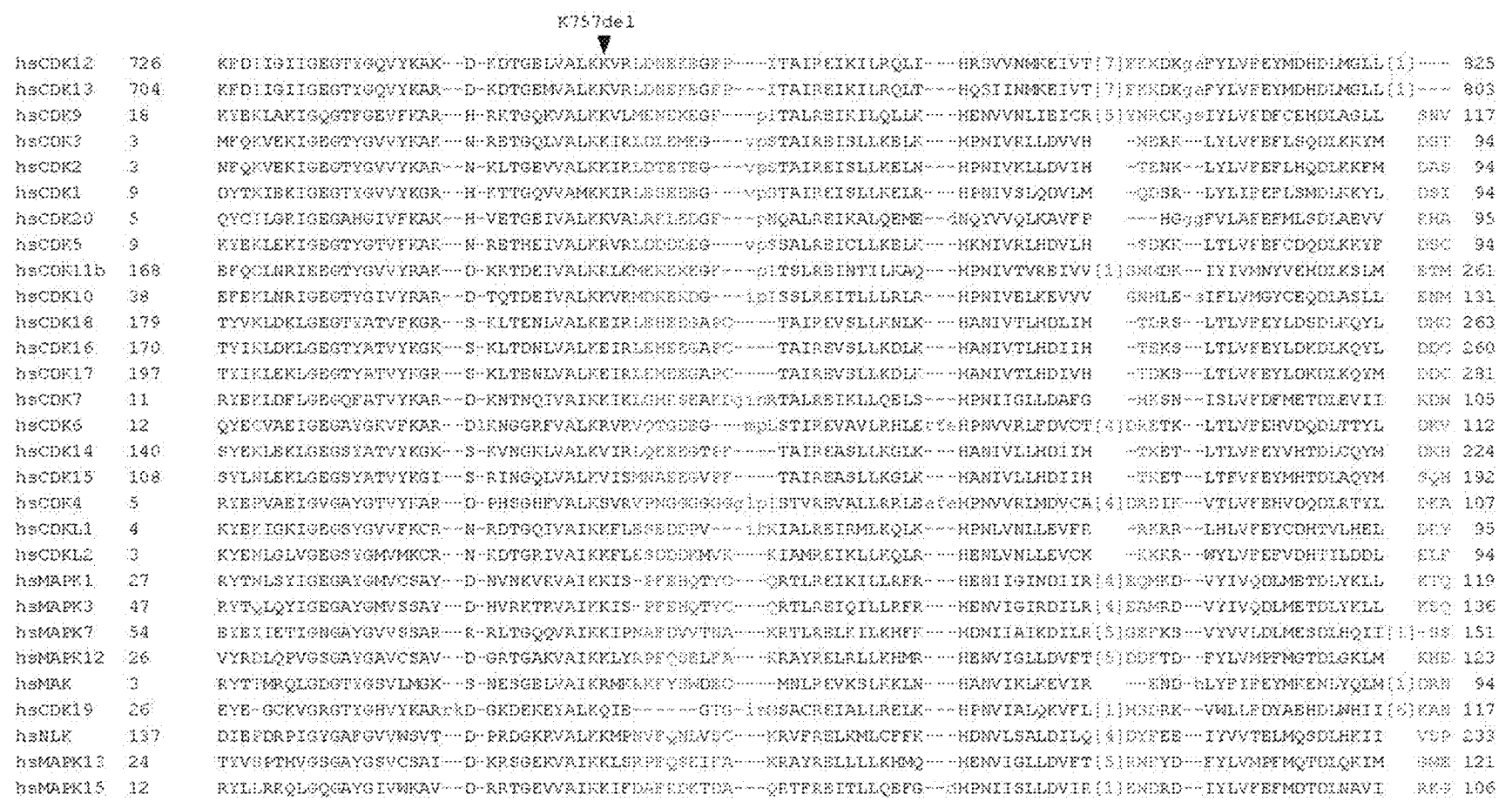
Figure 8B:
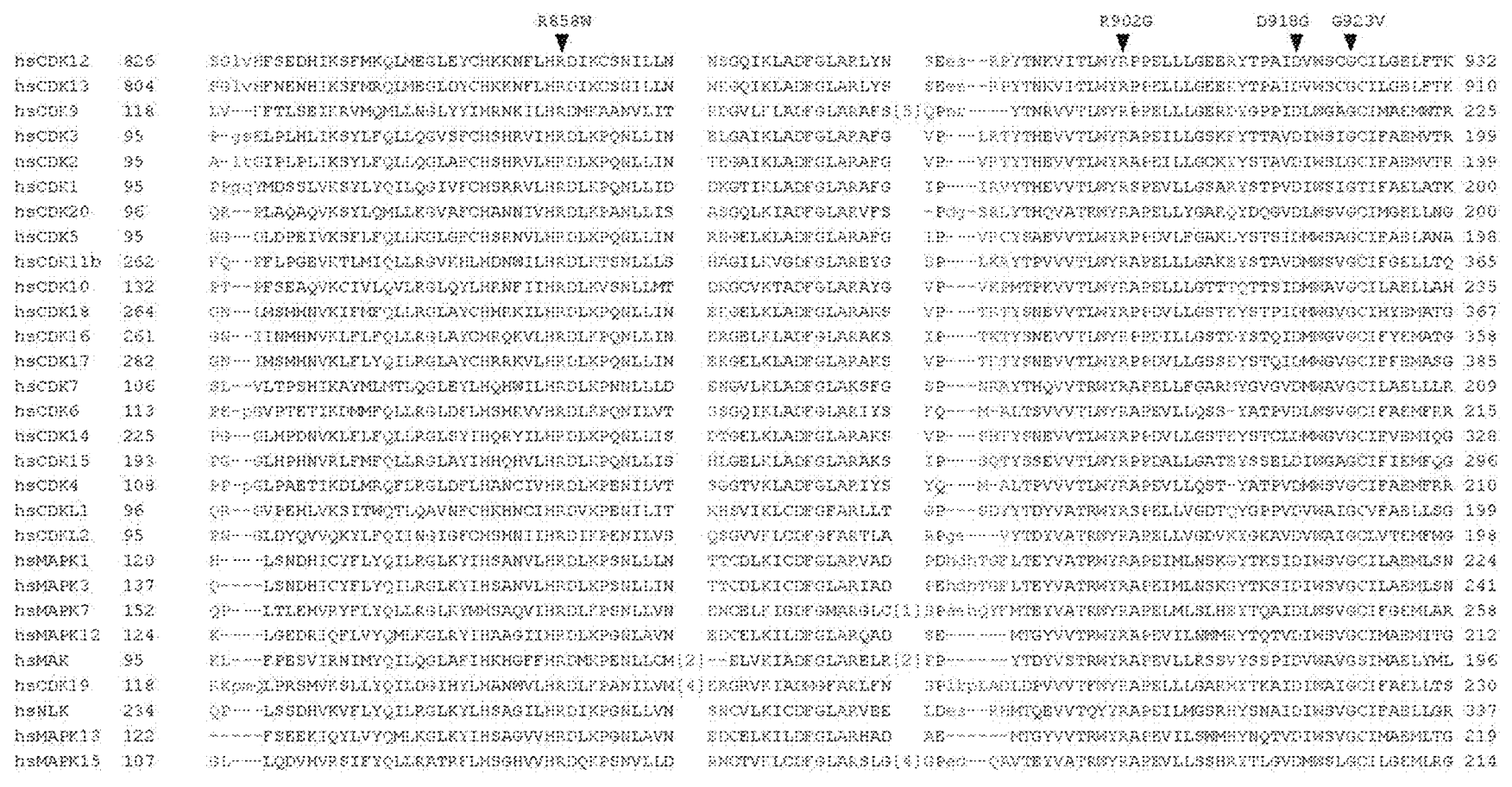

A subset (4.7%) of mCRPC patients were shown to harbor biallelic aberrations of CDK12. To confirm this observation, an extended multi-site metastatic prostate cancer cohort of 360 patients (CRPC360) was compiled, comprising SU2C (Robinson et al., 2015), MI-OncoSeq (Robinson et al., 2017), and UMich rapid autopsy cases (Grasso et al., 2012) (Table 1), a majority of which have matched whole-exome and transcriptome data. The combined data sets were reanalyzed using the MI-Oncoseq workflow (Robinson et al., 2017), producing harmonized call sets of somatic, germline, and structural variants. The MI-Oncoseq workflow was also used to analyze sequence data from 498 cases of primary prostate cancer in the TCGA (The Cancer Genome Atlas) dataset. Aberrations of CDK12 were detected in 25/360 of mCRPC patients (6.9%), 95% CI [4.6%, 10.2%] (FIG. 1A). This is significantly higher than in primary PCa, 6/498 patients (1.2%) (FIG. B and Table 2) (p<0.0001 Fisher exact test). Examination of data across additional primary and metastatic prostate cancer datasets revealed a similar difference in the frequency of biallelic CDK12 mutations between primary and metastatic cancer (Table 3) (Abida et al., 2017: Beltran et al., 2016; Fraser et al., 2017; Kumar et al., 2016). CRPC genomes are more highly mutated than those of localized tumors; however, the magnitude of the increased mutation rate is not sufficient to explain the increased frequency of biallelic loss of CDK12. The majority of CDK/2 mutations (83%) were truncating and resulted in the loss of the kinase domain. Missense mutations were clustered around catalytic and conserved residues in the kinase domain (FIG. 8). All patients showed biallelic inactivation of CDK12 by two somatic mutations (n=10), a mutation compounded by loss-of-heterozygosity (LOH) (n=14), or homozygous loss (n=1). CDK2 has been shown to have a very low tolerability for germline loss-of-function variants (Juan et al., 2016), and, consistently, no germline aberrations were detected in our cohort (Table 4).

Figure 1C:
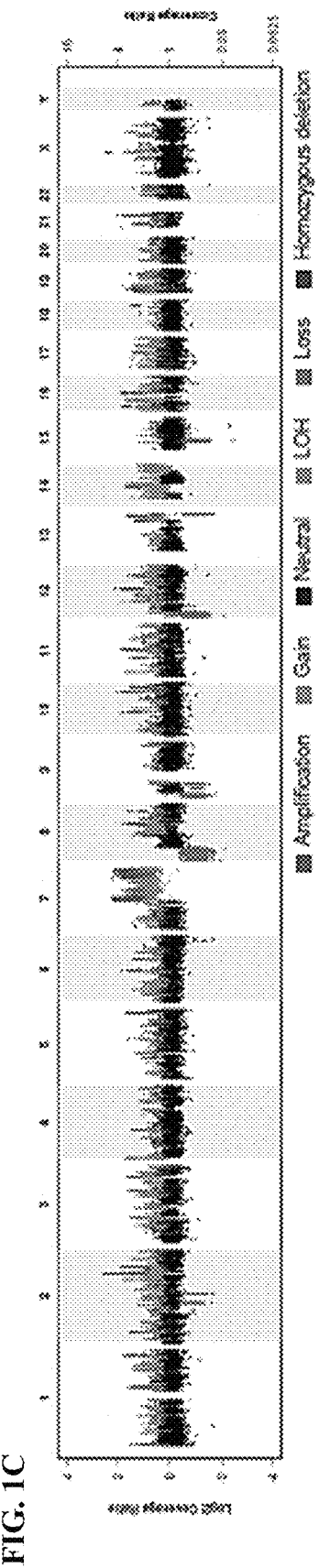
Figure 9:
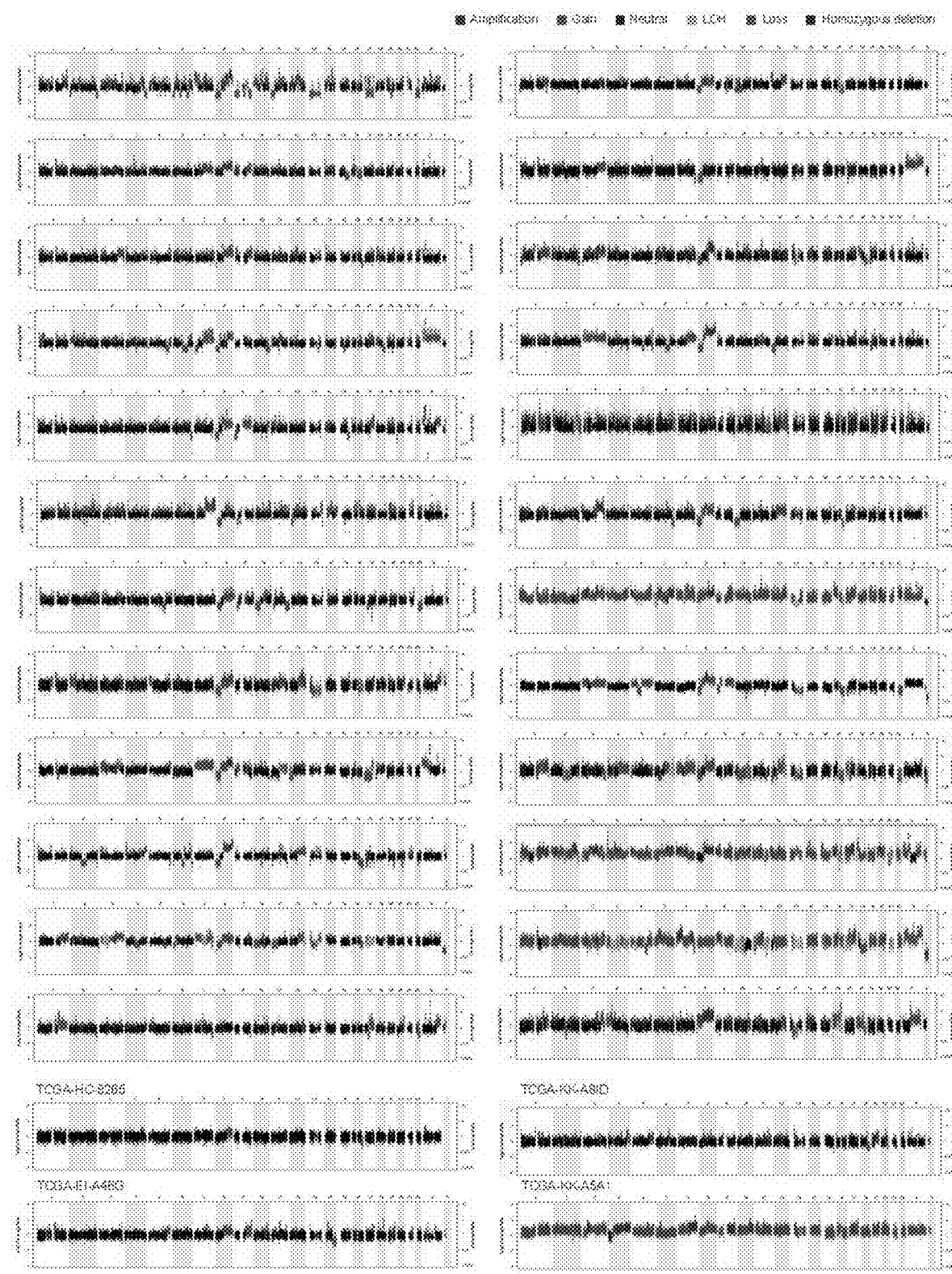
FIG. 9A-B shows copy-number plots of CDK12-mutant tumors. Representative mCRPC cases are shown in (FIG. 9A), and primary prostate cancer cases are shown in (FIG. B).

CDK12-Mutant Tumors are Baseline Diploid with an Excess of Focal Tandem Duplications A significant increase in genomic instability is a hallmark of metastatic tumors (Negrini et al., 2010). While primary prostate cancers are largely diploid and genetically stable, metastatic tumors often show extensive LOH, aneuploidies, and a significant increase in mutational burden (Robinson et al., 2017). The landscape of CDK12-mutated mCRPC cases was observed and a distinctive genomic landscape was identified (FIGS. 1C and 9), similar to that identified in a subset of ovarian cancers (Popova et al., 2016). The prototypical CDK/2-mutant tumor was baseline diploid and had few arm-level copy-number aberrations except isochromosome 8q, but notably, hundreds of focal copy-number gains were dispersed across the genome. While focal gains were present on all chromosomes within a sample, other focal events, such as high-level amplifications or deletions, were rare or absent. Loss of CDK12 activity through biallelic inactivation was strongly associated with this form of genomic instability (p<0.00001, Fisher exact test). All cases with CDK12 inactivation, and only cases with CDK12 mutation, exhibited this form of genome instability in both the metastatic and primary cohorts (FIG. 9 and Table 2). No other genes were positively associated with this genome instability. ETS fusions and PTEN mutations were depleted in cases with CDK12 mutations (p<0.00001 for both, Fisher exact test). None of the CDK12-mutated tumors exhibited a neuroendocrine phenotype.

Figure 1E:
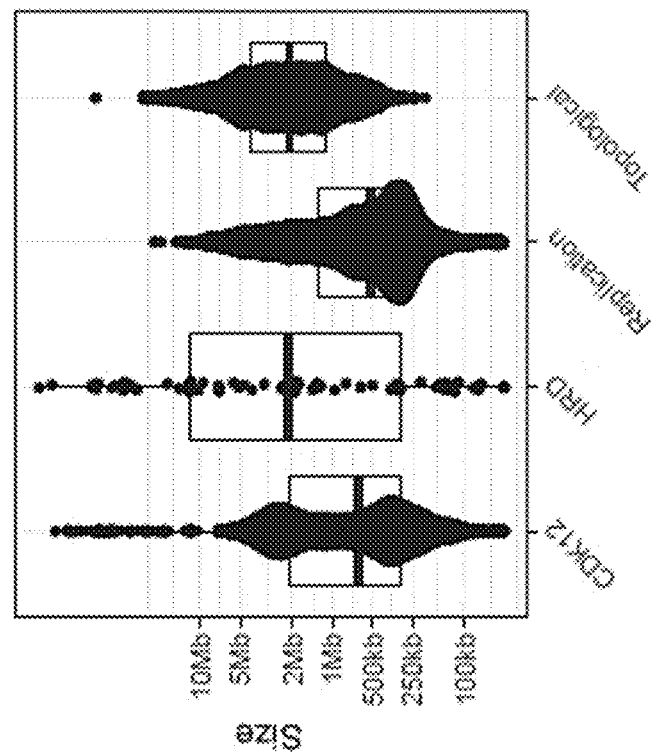
Figure 1D:
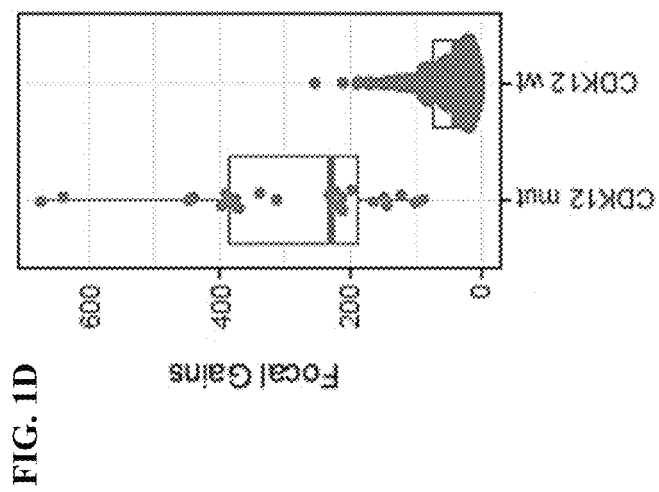
Figure 10A:
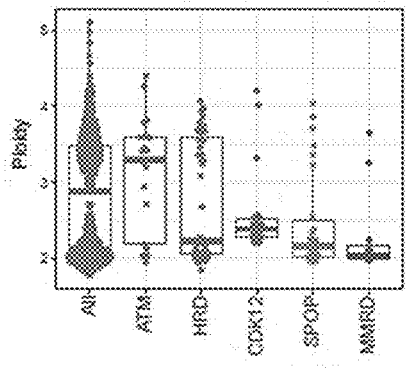
FIGS. 10A-F shows genetic instability of CDK12-mutant tumors.
Figure 10B:
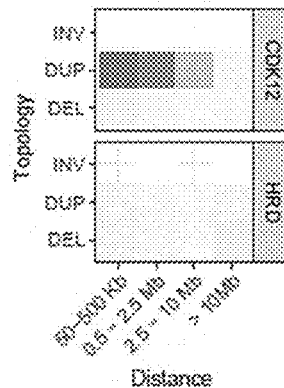
Figure 10C:
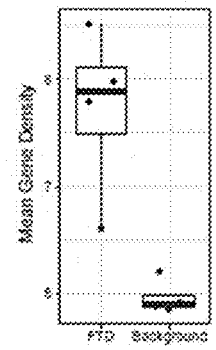
Figure 10D:
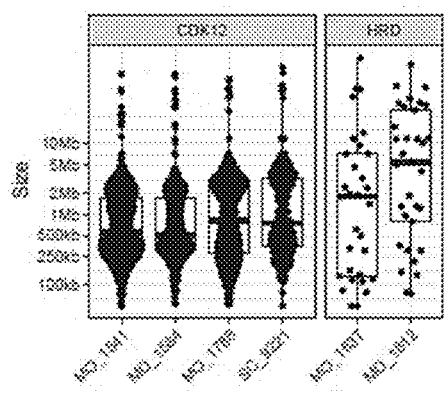
Figure 10E:
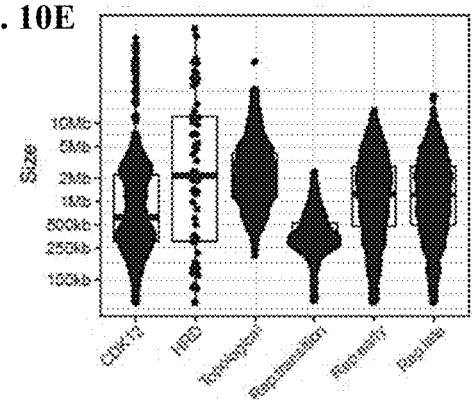
Figure 10F:
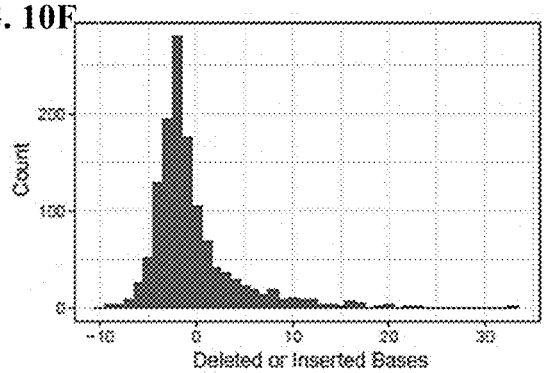

The genomic phenotype of CDK12-mutant tumors was compared to other cases in the CRPC360 cohort, particularly those associated with frequent primary genetic drivers (PGDs) of prostate cancer: ATM mutations, HRD, SPOP mutations, and MMRD. Like CDK12-mutant cases, SPOP- and MMRD-driven tumors were mostly diploid, while a large subset of ATM- and HRD-driven tumors showed large-scale aneuploidy (FIG. 10A). The high number of focal gains was consistently observed in CDK12-mutant cases compared to those in the cohort with wild-type CDK12 (FIG. 1D). Detection of genomic structural variants (SV) from whole-genome sequencing (WGS) data confirmed that the gains were focal tandem duplications (FTDs) (FIG. 10B) and enriched in gene-dense regions (FIG. S3C). Strikingly, comparison of CDK12-mutant and HRD index cases revealed a bimodal distribution of FTD sizes in CDK12-mutant, but not HRD, tumors (FIG. 10D). The modes of this distribution were consistent with the sizes of replication domains (RD), but not topological domains (TD) (FIG. 1E). Specifically, the ~2.4 Mb peak was close to the mode of the early/late RDs, while the ~0.4 Mb peak matched the size of transitional RDs (Hiratani et al., 2008) (FIG. 10E). Breakpoint sequence assembly revealed that FTDs were enclosed by error-prone junctions indicative of a non-homologous end joining (NHEJ)-mediated repair process (FIG. OF). We refer to these events as CDK12-associated FTDs (CDK12-FTDs) to distinguish them from BRCA-dependent events and focal amplifications.

CDK12-Mutants Represent a Specific Class of Prostate Cancer with a Distinct Transcriptional Phenotype Genetic associations between CDK12 loss and the most frequent PGDs of prostate cancer were analyzed to determine whether CDK12-mutant cases were a unique class of mCRPC. Strikingly, CDK12 aberrations were mutually exclusive with all of the PGDs analyzed (ETS fusions, SPOP mutations, HRD, ATM mutations, and MMRD) (FIG. 2A).

Figure 2C:
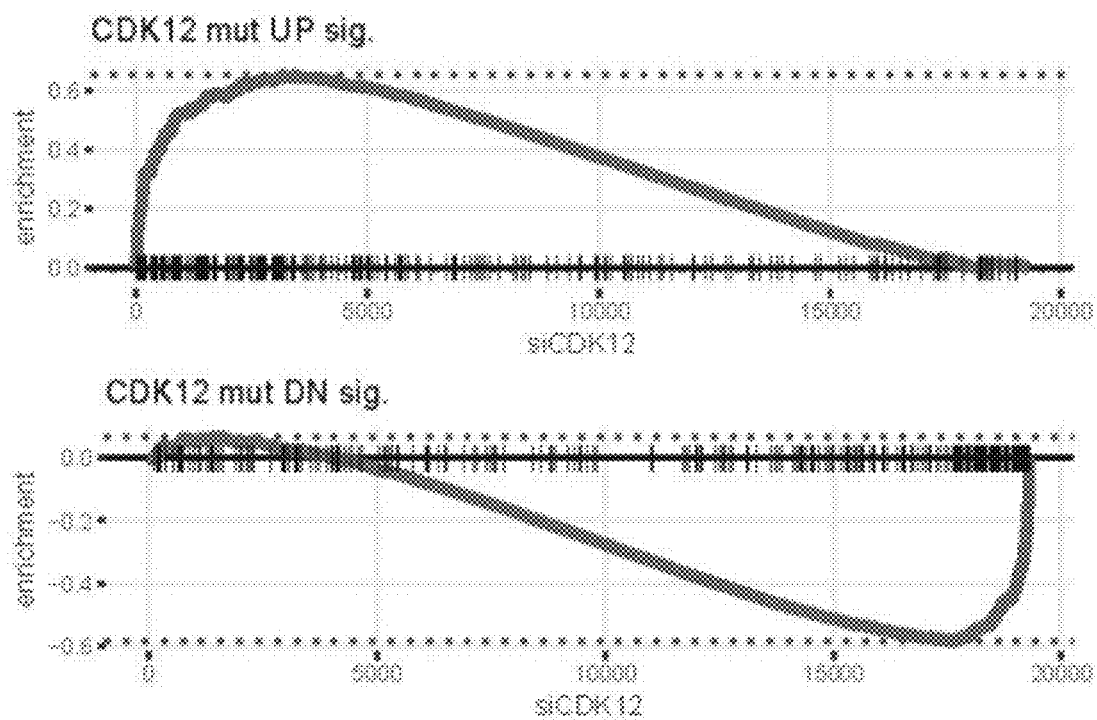

Several of the established prostate cancer PGDs have been associated with characteristic gene expression profiles (Herschkowitz et al., 2008; Parikh et al., 2014: Saal et al., 2007). It was contemplated that CDK12 loss may similarly constrain a specific transcriptional phenotype. To test this rigorously, the expression profiles of mCRPC cases with aberrations in the specific PGDs or CDK12 was compared to a reference set of cases (n=92) that were wild-type for all the PGDs, including CDK12 (PGD-WT). It was found that CDK12 aberrations were associated with the highest number of differentially expressed genes (DEGs) (FIG. 1A), independent of differences in the number of cases for each PGD, and across a wide range of effect-size (FIG. 2B), and p-value cutoffs. The most up—(e.g. AIFM22. ARID3C, TBX4) or downregulated (e.g. TSACC, CDNF, ABCC12) genes have not been previously studied in the context of prostate cancer (FIG. 11B). To establish a causal link between this transcriptional phenotype and loss of CDK12, siRNA-mediated knockdown experiment was performed in LNCaP cells. Depletion of CDK12 at the RNA and protein levels resulted in growth arrest (FIGS. 11C-E) and profound transcriptional changes. In addition, DEGs associated with CDK12 mutations in patients were almost perfectly recapitulated in vitro (FIG. 2C), which allowed us to define a transcriptional signature of CDK12-loss in mCRPC (Table 5).

Figure 2D:
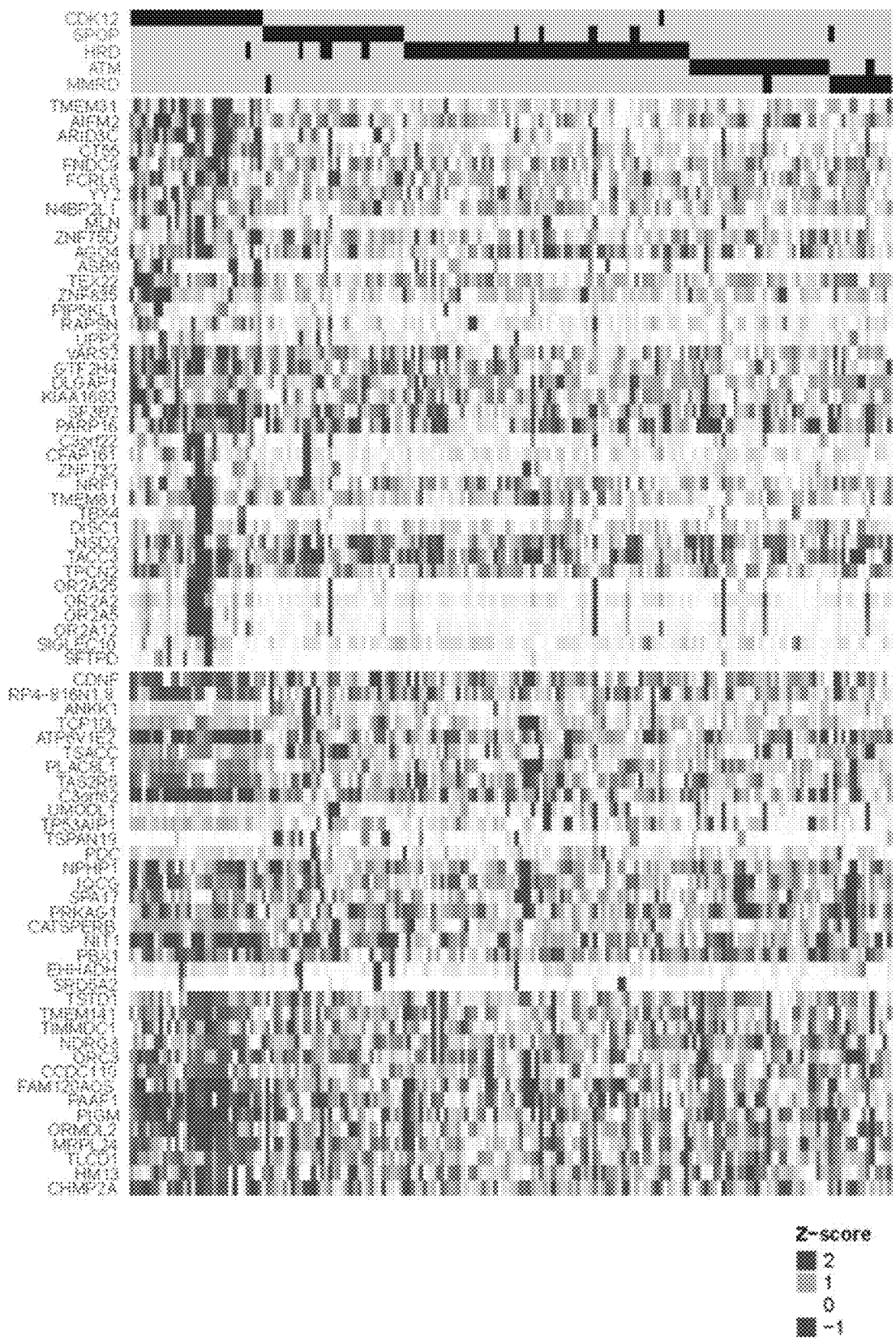
Figure 11G:
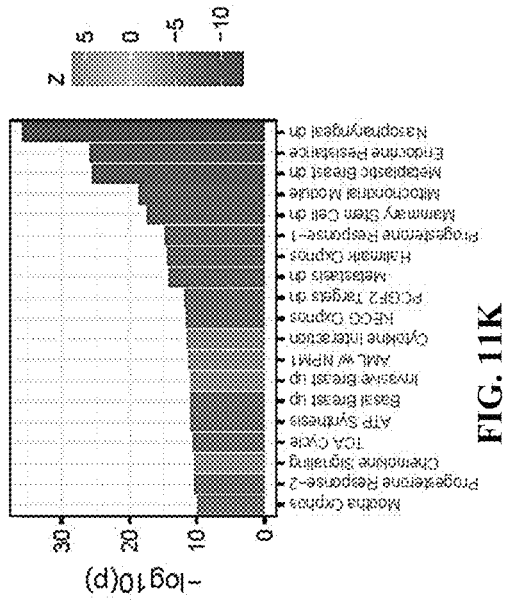
Figure 11G:
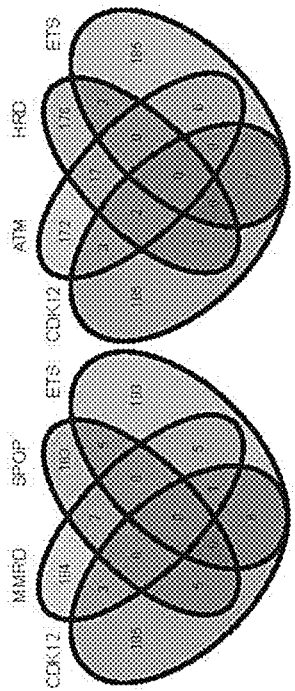
Figure 11K:
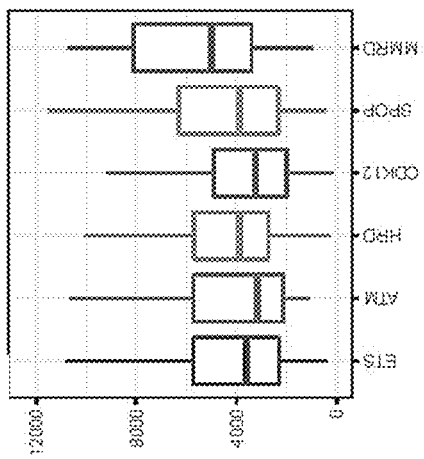
Figure 11J:
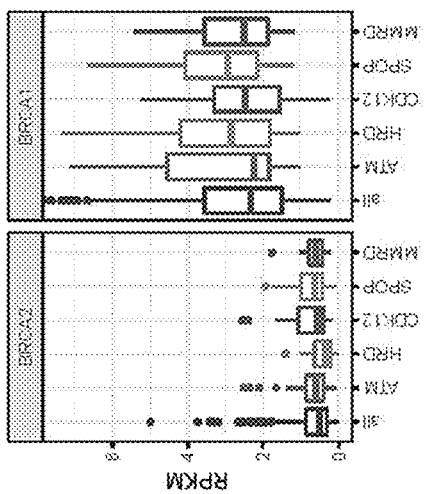
Figure 11I:
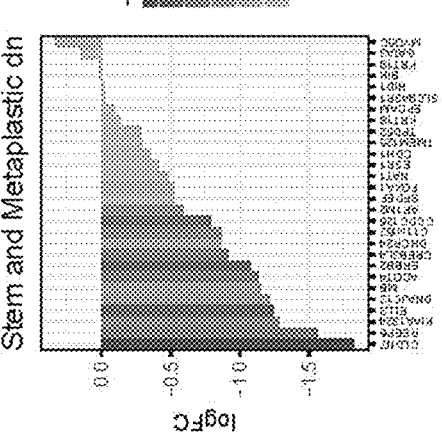

While most CDK12-mutants retained active androgen receptor (AR) signaling (FIG. 11F) (Beltran et al., 2016), their expression signature was distinct from the equivalent signatures for the other PGDs (FIGS. 2D and 11G). Gene set enrichment analysis (GSEA) (Subramanian et al., 2005) across the MSigDB (Liberzon et al., 2015) revealed significantly perturbed curated gene sets (FIG. 1H). The most prominently altered were those related to oxidative phosphorylation (down, "Hallmark Oxphos", "KEGG Oxphos", "TCA Cycle", etc.), inflammatory response (up. "Cytokine Interaction". "Chemokine Signaling"), hormone receptor signaling (down, "Endocrine Resistance", "Progesterone Response-1", "Progesterone Response-2"), and epithelial dedifferentiation (down, "Metaplastic Breast dn", "Basal Breast up"). To understand this further, a core set of 28 genes downregulated in both metaplastic and stem-like breast cancer (two of the most significant gene sets) was delineated. This set included major luminal epithelial markers (SPDEF, FOXA1, ESR1) and luminal adhesion molecules (CDH1, CLDN7). Strikingly, the majority of those genes were significantly downregulated in CDK12-mutant mCRPC (FIG. 11I). Although the shift from oxidative to glycolytic metabolism (Warburg effect) is a hallmark of many cancer types (Vander Heiden et al., 2009), it is not a characteristic of most prostate cancers (Cutruzzola et al., 2017). This downregulation of genes associated with mitochondrial energy metabolism, often associated with cancer stemness and dedifferentiation (Ito and Suda, 2014), further underscores the uniqueness of the CDK12 transcriptional phenotype relative to other classes of mCRPC.

Figure 3A:
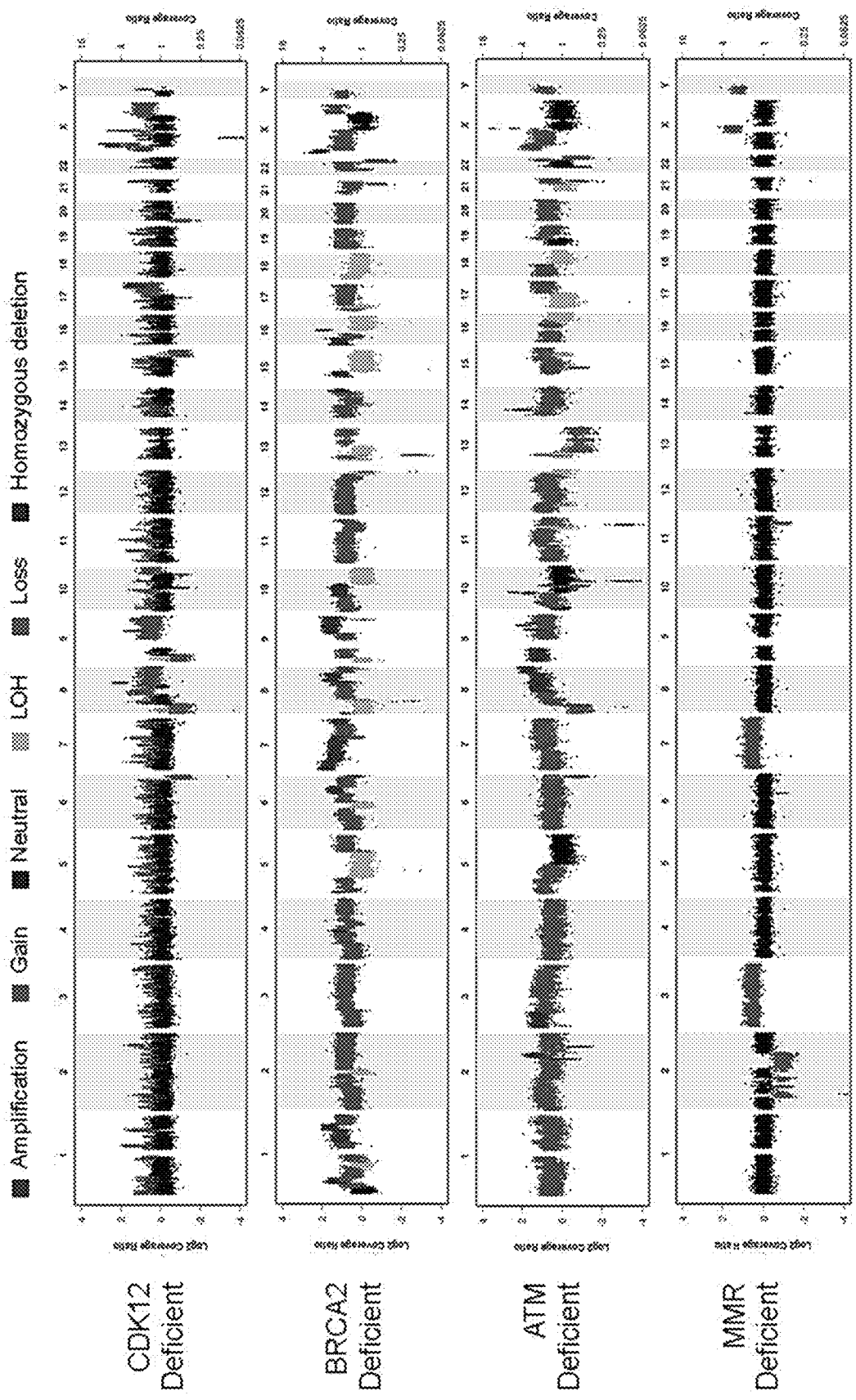

CDK12-Mutant Tumors Display Characteristic Copy-Number and Mutational Signatures Distinct from DNA Repair-Deficient Prostate Cancer Previous studies indicated that CDK12 is involved in controlling genomic stability through regulation of HR or other DNA damage response effectors (Blazek et al., 2011; Ekumi et al., 2015; Joshi et al., 2014; Juan et al., 2016). The CRPC360 transcriptional data also showed a unique signature for CDK12-mutant tumors (FIG. 2D). Comparison of copy-number plots from example tumors deficient in CDK12, BRCA2, ATM, or mismatch repair genes further confirmed distinct characteristics of the CDK12-mutant subtype (FIG. 3A). Large-scale copy-number gains were evident in the BRCA2- and ATM-deficient cases, as compared to CDK12-mutant or MMRD cases (FIG. 3A). To quantitate and contrast the CDK12-mutant pattern with the other PGDs on a larger scale, absolute copy-number levels from whole-exome sequencing (WES) data were tallied across the entire CRPC360 cohort (FIG. 3B). These analyses showed that BRCA and ATM mutated, as well as ET fusion-positive, tumors had the highest percentage of copy-number gains, while the majority of CDK12-mutant and MMRD tumors did not exhibit changes in ploidy (FIG. 3B).

Genomic signatures are a powerful approach to study the mutagenic imprints of environmental and genetic factors. To determine if loss of CDK12 activity is associated with a distinct signature, mutational burden as well as mutational signature was computed across various genetic drivers (FIG. 3C). MMRD cases had the highest mutational burden and a signature consistent with microsatellite instability (signature 6) (Alexandrov et al., 2013). HRD tumors had the next highest mutational burden, and BRCA-loss was associated with an evident signature 3 (Polak et al., 2017). The remaining PGDs, including CDK12, had a baseline level of SNVs and were dominated by age-related 5-methylcytosine deamination (signature 1). Combined, these data support that the CDK12-mutant subtype is distinct from either the HRD or MMRD type of prostate cancer. In particular, CDK/2-mutants are different from tumors with HRD, which was previously presumed to be the pathway through which CDK12 regulated genomic stability. Notably, the expression of BRCA1 or BRCA2 was not affected by CDK12 mutational status (FIG. 11J) and neither was the expression of other genes encoding long transcripts and cognate proteins (FIG. 11K), a class previously suggested to be regulated by CDK12 (Blazek et al., 2011).

Figure 12A:
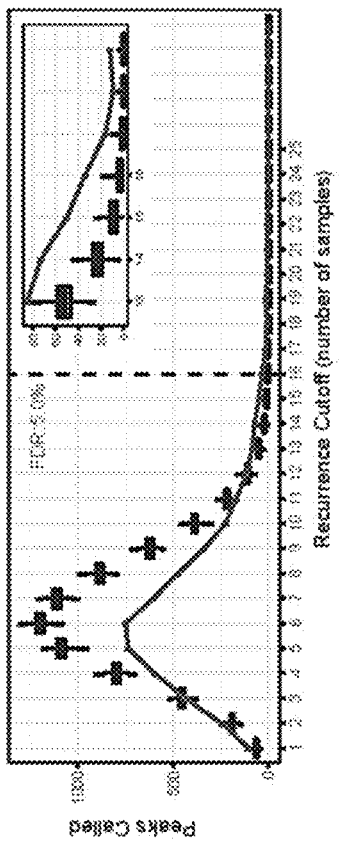
Figure 12B:
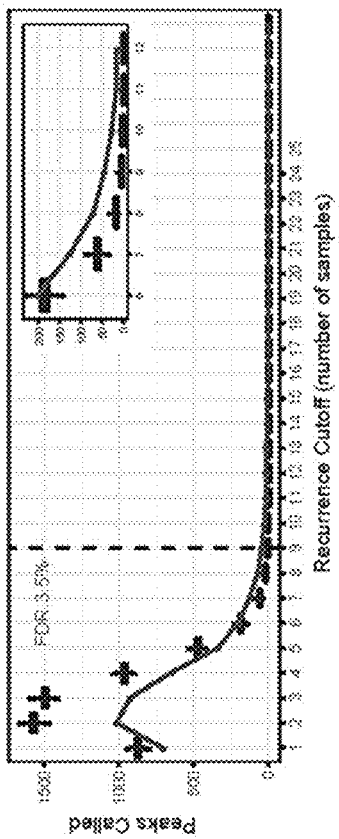
Figure 12C:
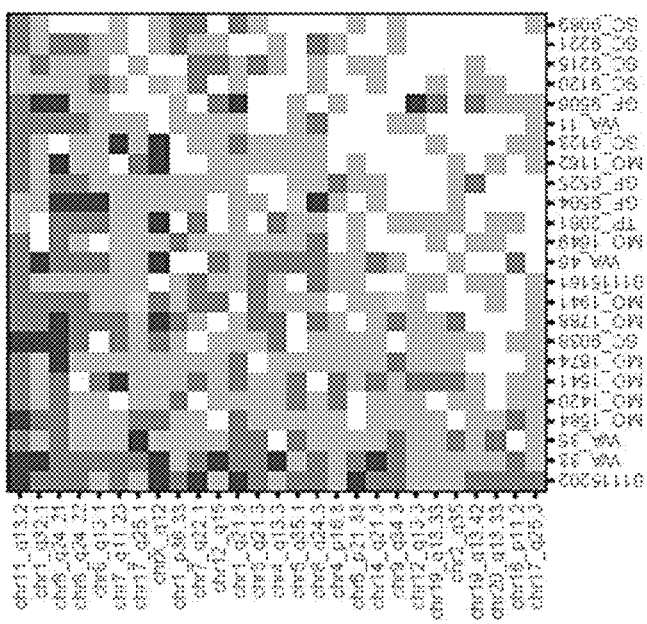

CDK12-FTDs Result in Highly Recurrent Gains of Genes Involved in the Cell Cycle and DNA Replication The large number of FTDs present in all CDK12-mutant tumors introduces the possibility of detecting synthetic genetic dependencies or epistasis (Ashworth et al., 2011; O'Neil et al., 2017). One approach is to look for loci with recurrent CDK12-FTDs at the cohort level. To identify such genomic regions, a Monte Carlo null model was developed to simulate the expected distribution of FTD recurrences, given their number and size. Because this distribution depends on the threshold below which a copy-number event is considered "focal", both stringent (2 Mb. "narrow") and relaxed (8 Mb, "wide") definitions were applied (FIGS. 12A-B). Using both models, a total of 27 loci with recurrent focal gains at false-discovery rates of 3.5% and 5%, respectively were detected (FIGS. 4A and 12C). Indicative of strong positive selection, several of these loci showed copy-number gains in almost all CDK12-mutant cases (FIG. 12C). Strikingly, their recurrence was significantly lower in CDK12 wild-type tumors, which indicates a synthetic dependency (FIG. 12D). As a prominent exception, the MYC and AR loci (FIG. 12E) were recurrently amplified, regardless of CDK12 status, which underscores their fundamental role in prostate cancer. Although most of the CDK12-FTDs result in the gain of one additional copy (FIG. 3B), it was observed that the most recurrent genes also had the highest copy-number gains (MTYC, AR, CCND1), indicative of gene dosage selective pressure (FIG. 4B).

The delineation of minimal common regions (MCR) is an established strategy to identify genetic targets that are subject to positive selection and, hence, responsible for the recurrent copy-number aberrations (Mermel et al., 2011). In order to nominate such candidate genes in CDK12-mutant mCRPC, FTDs were summarized into MCRs at the most recurrent loci (FIG. 4C). The AR locus, whose MCR was centered on the AR gene as expected, represents a positive control for this approach. Of the recurrent loci, two were consolidated into a narrow MCR harboring a single candidate gene (MCM7 and CDK18), while one required further prioritization. The chr11_q13.2 locus is characterized by high gene density and the presence of RAD9A and CCND1, all of which could contribute to the FTD recurrence of this region. CCND1 was also associated with the highest copy-number gains, comparable in magnitude with amplifications at the MYC and AR loci (FIG. 4B). Strikingly, candidate genes under positive selection, MCM7 (recurrence frequency in CDK12-mutants: 63%), RAD9A (88%), CDK18 (67%), and CCND1 (92%), have crucial roles in DNA replication and genome stability (Table 7). Amplifications of MYC (68%) and AR (75%) are among the most recurrent genetic events in mCRPC and not specific to CDK12-mutants. Correspondingly, their molecular functions are pleiotropic; both regulate the cell cycle (Bretones et al., 2015: Yuan et al., 2006), and contribute independently to proliferation of prostate cancer cells (Bernard et al., 2003).

CDK12-FTDs Induce Expression in a Dosage Dependent and Independent Manner

Large-scale copy-number aberrations and focal amplifications have been associated with differential and outlier gene expression (Tang and Amon, 2013). However, not all structural variants or copy-number gains and losses alter gene expression levels in a dosage dependent manner. For example, a small copy-gain may result in enhancer hijacking and outlier gene expression, as is the case in PRDM6 in medulloblastoma (Northcott et al., 2017). Alternatively, it can also separate a gene from its enhancer or lead to epigenetic silencing, resulting in paradoxical loss of expression (Platzer et al., 2002).

In order to better understand some of the functional consequences of CDK12-FTDs, both global and gene-specific associations between copy-number and expression levels were interrogated. To assess global effects of CDK12-FTDs, changes in average expression levels associated with the focal increases in copy-number were assessed (FIGS. 12F-G). A significant increase in the number of DEGs at each absolute copy-number level was observed (FIG. 12F). To demonstrate the feasibility of identifying gene-specific effects given the sample size, the expression of three genes associated with the highest average copy-number gains and high recurrence: CCND1, MC, and AR were interrogated (FIG. 4B). A significant dose dependent relationship for CCND1 and AR, but not MYC, was observed (FIG. 13A). This analysis was expanded to other cancer-related genes and similar trends for key oncogenes in the MAPK, AKT, and MTOR pathways were identified (FIG. 13B). Strikingly, dosage dependence was much less robust for receptor tyrosine kinases (RTK), which were dominated by singleton expression outliers (FIG. 13C). A global analysis was performed to determine the contribution of CDK12-FTDs to the prevalence of expression outliers. Overall, outliers were more frequent in CDK12-FTDs, and their frequency increased with copy-number gains (0.5% to 4%) (FIG. 12G).

Mutant CDK12 Prostate Cancers Exhibit a Unique Structural Signature Characterized by Increased Gene Fusions Transcriptome sequencing data were used to delineate signatures of structural genomic instability across the different classes of PGDs. As shown in FIG. SA, CDK12-mutant tumors had the highest fusion burden, consistent with the large number of focal copy-number events (FIG. 1D) and their enrichment in gene-rich regions (FIG. 10C). The prototypical CDK12-mutant case exhibited a large number of fusions (FIG. 5A) generated by tandem duplications and relatively fewer by translocations, inversions, or deletions (FIG. 5B). This contrasts with HRD and MMRD tumors, which have a significantly lower fusion burden dominated by translocations. Next, "fusion-grams" were designed to quantitatively compare signatures of structural variants between the varying prostate cancer classifications (FIG. 5C). In a fusion-gram, structural variants are classified according to the observed distance and topology of their breakpoints (e.g., deletion, duplication, inversion, translocation). For CDK12-mutant tumors, the majority of fusions (70%) were classified as duplications within a cytoband or chromosome arm. All other PGDs had signatures dominated by translocations (~49%) and fewer overall duplications (11%) than deletions (18%) or inversions (22%), further supporting the uniqueness of CDK12-mutant PCa.

Figure 13D:
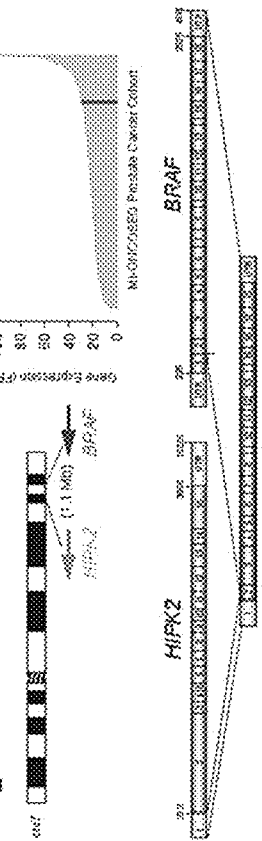
Figure 13F:
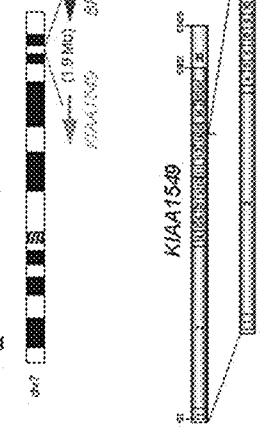
Figure 13E:
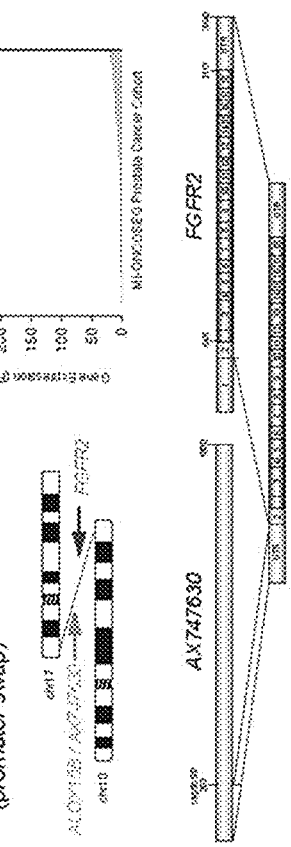
Figure 13G:
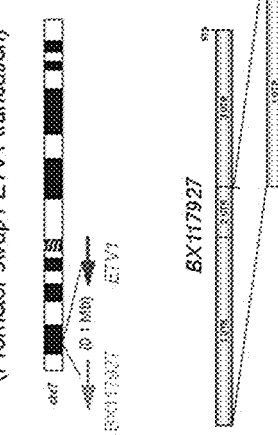

Since CDK12-FTDs are associated with expression outliers (FIG. 12G) and a large number of gene fusions (FIG. 5A), it was hypothesized that some of those events are potential secondary genetic cancer drivers. Similar associations between the presence of hotspot aberrations and the activity of mutational processes have been reported for MMRD (Temko et al., 2017). Candidate driver events where a chromosomal aberration resulted in either outlier expression of an oncogene or formation of a likely oncogenic gene fusion were identified. In addition to the singleton outlier RTKs (FIG. 13C), two cases of BRAF fusions (KIAA1549-BRAF and HIPK2-BRAF) generated as a result of a CDK2-FTD were identified (FIGS. 13D-E). BRAF fusions was been reported in prostate cancer (Palanisamy et al., 2010): however duplications involving the KIAA1549-HIPK2-BRAF locus have thus far been noted as hallmarks of pilocytic astroctoma (Yu et al., 2009). A promoter hijacking event leading to outlier expression of ETV1 was further identified (FIG. 13F). However, not all secondary events could be inferred as direct consequences of CDK12-FTDs. For example, a translocation leading to extremely high (250 FPKM) expression of full-length FGFR2 was identified (FIG. 13G). FGFR fusions can be found in many solid tumors and are compelling targets for precision therapy (Wu et al., 2013).

Figure 5D:
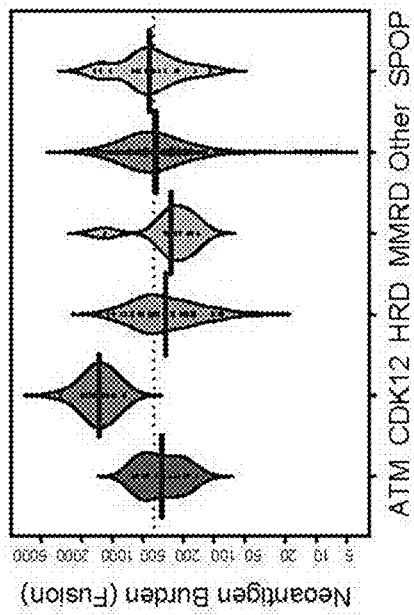
Figure 5E:
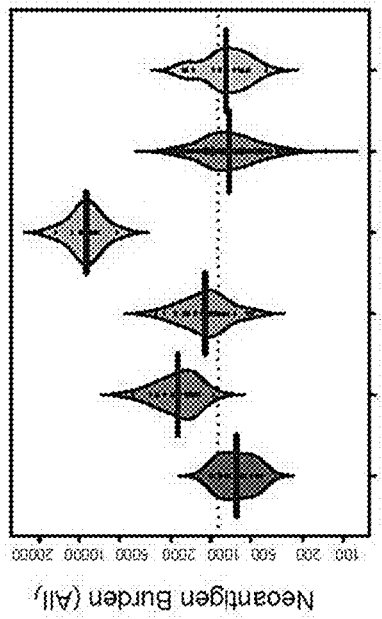
Figure 5F:
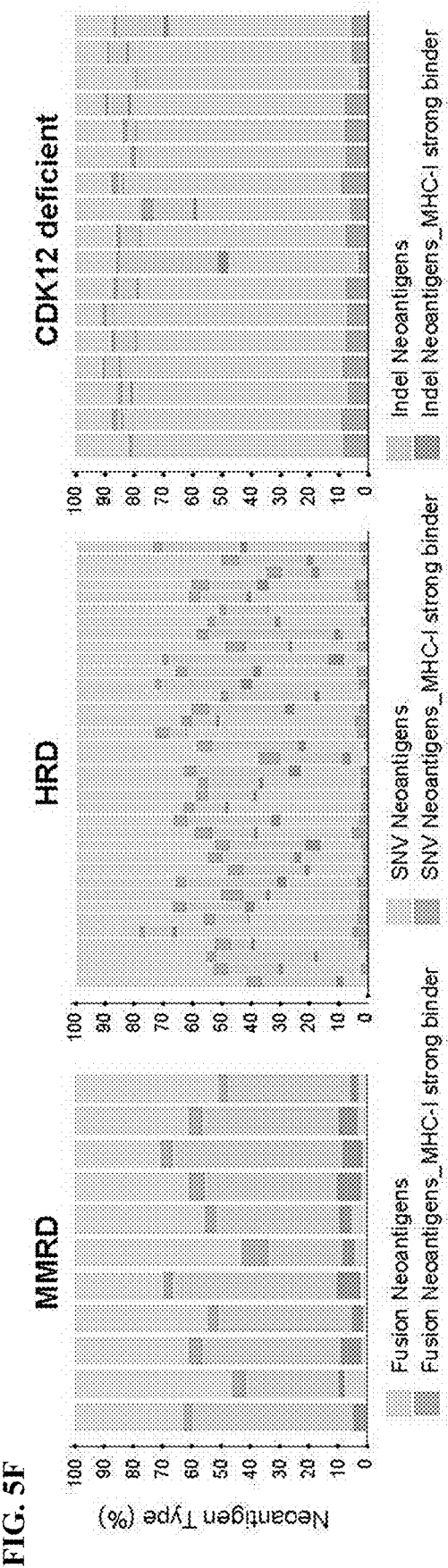

CDK12-Mutant Tumors are Characterized by Increased Gene Fusion-Induced Neoantigen Open Reading Frames Tumor immunogenicity is significantly associated with mutational burden and neoantigen load (Le t al., 2015). It was contemplated that gene fusions and their chimeric protein products yield significant numbers of neoantigens in CDK12-mutant tumors. Comprehensive prediction of novel peptides from mutation and fusion calls was conducted and it was found that MMRD, HRD, and CDK12-mutant tumors had a significantly higher neoantigen burden compared to other mCRPC molecular subtypes (FIG. 5D). Strikingly, the mutational mechanism by which the neoantigens were generated was specific to each subtype. While neoantigens in MMRD and HRD tumors were formed by indels and SNVs, fusions contributed most of the novel epitopes in CDK12-mutant mCRPC (FIGS. 5E-F). The calculated neoantigen burden from fusions was the highest in CDK/2-mutant tumors among the other PGDs (FIG. 5E). Importantly, these analyses also identified neoantigens with strong MHC class-I binding affinities that are predicted to be candidate epitopes for immunotherapy (FIG. 5F).

Figure 14A:
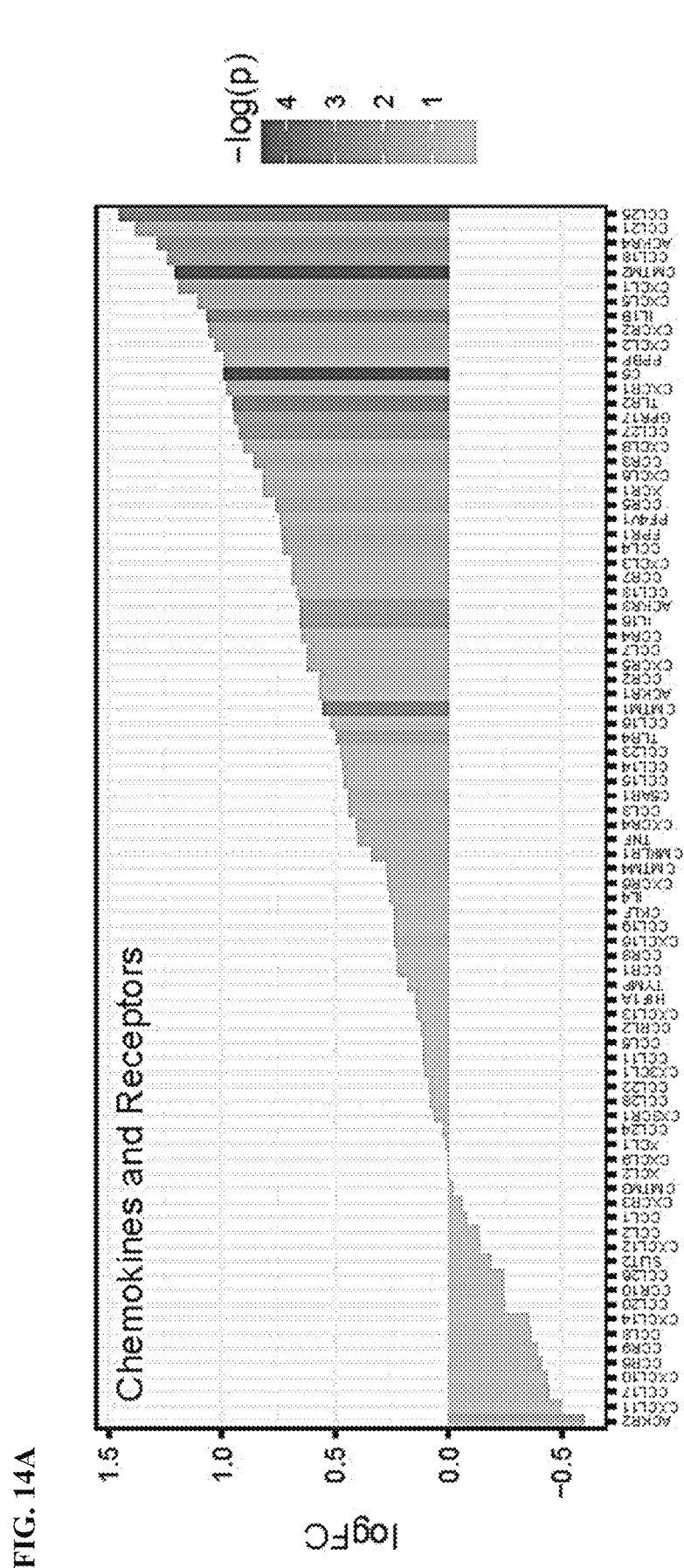
FIGS. 14A-F shows immunophenotypic characteristics of CDK12-mutant tumors.
Figure 14B:
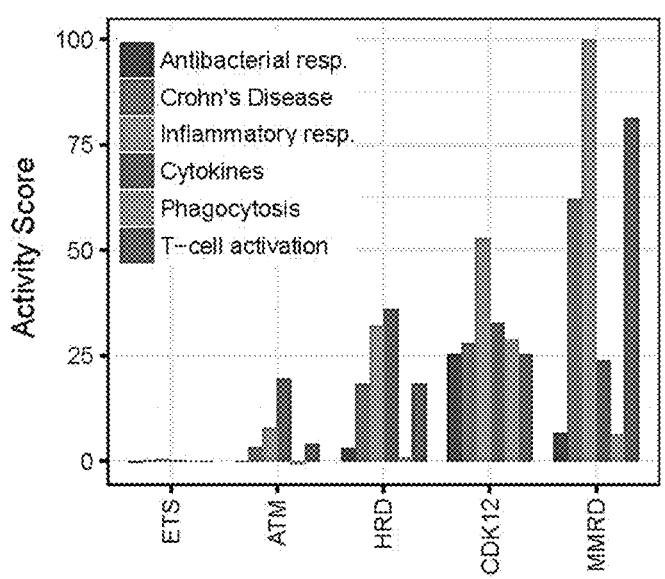

CDK12-Mutant Tumors Show High Immune Infiltration and Imprints of Immune Evasion Significant activation of the cancer inflammatory hallmark gene-set in CDK12-mutant tumors and LNCaP cells transfected with siRNA to CDK12 was observed (FIG. 6A). Compared to wild-type tumors (PGD-WT, see above), CDK12-mutant cases showed increased expression of chemokines and their receptors (FIG. 14A). Overall, reduced or low expression of chemokines that can recruit regulatory T cells (CCL17, CCL20, CCL22) (Curiel et al., 2004; Zou, 2006) and an increase in chemokines that support dendritic cell migration into the tumor microenvironment (CCL21, CCL25) was observed (Chan et al., 1999; Gosling et al., 2000; Vicari et al., 1997). Interestingly, certain direct pro-tumor chemokines, including CCL18 and CXCL8 (Nagarsheth et al., 2017), were enriched in patients with CDK12 mutations. To determine whether this immune phenotype was specific to CDK12-mutant tumors, the activation of the top signatures was contrasted across genetically unstable mCRPC subtypes. Strikingly, only MMRD and CDK12-mutant tumors showed robust activation of chemokine signaling/inflammatory response and high immune infiltration as estimated by the cohort MImmScore (Robinson et al., 2017) (FIGS. 6B and 14B). Taken together, these data indicate that CDK12-mutant tumors are immunogenic and infiltrated by leukocytes but evolve chemokine-mediated mechanisms of immune evasion.

Figure 14C:
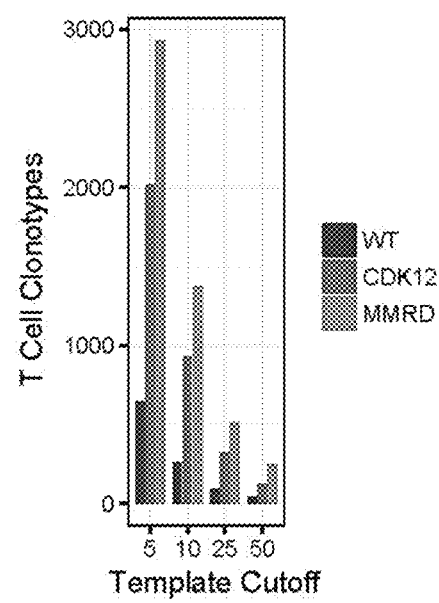
Figure 14D:
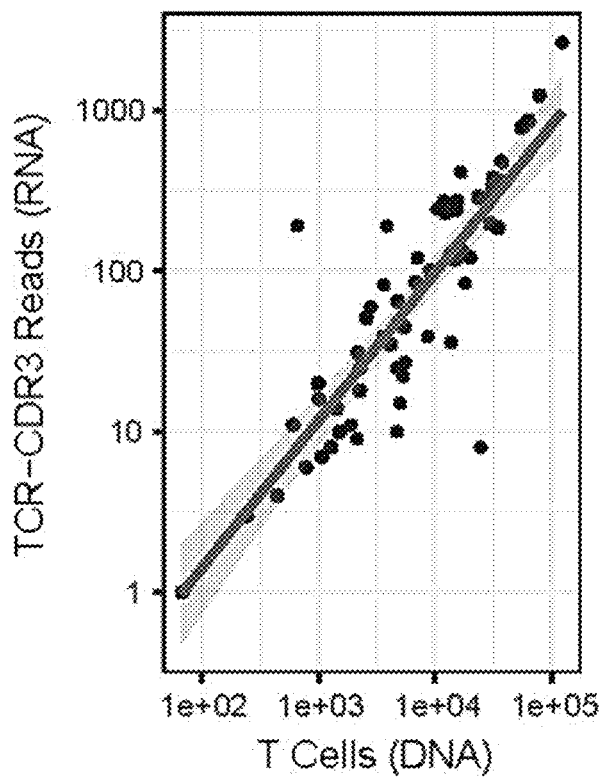
Figure 14F:
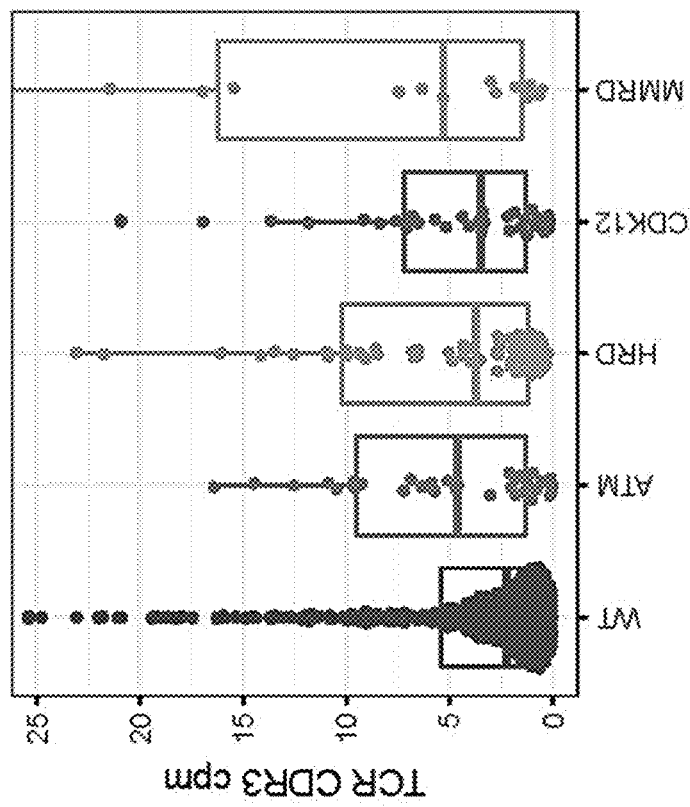
Figure 14E:
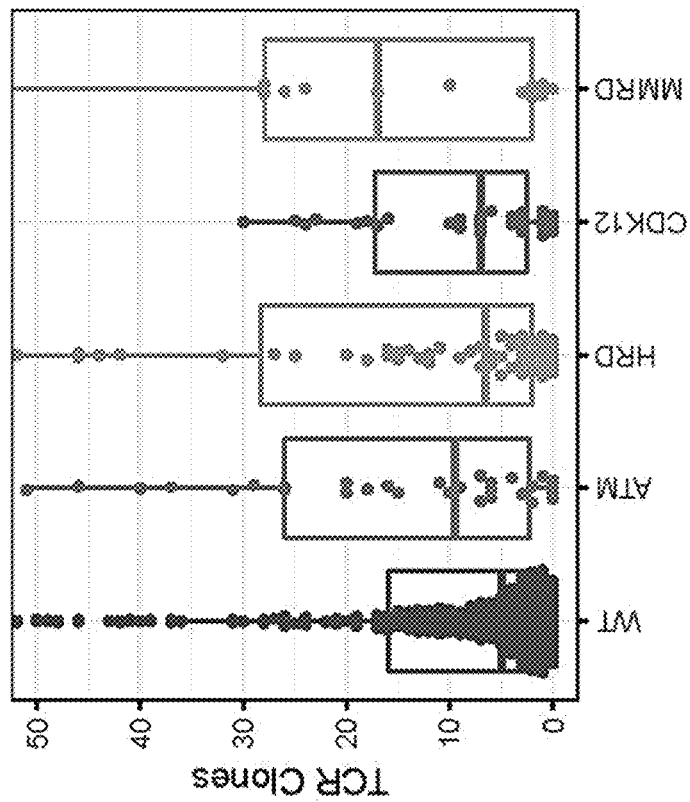

Antigen recognition by T cells leads to their clonal expansion. Within an expanded clonotype, all effector T cells share the same antigen specificity dictated by a unique CDR3 sequence of the T cell receptor. To detect whether increased neoantigen burden was mirrored by an increase in T cell clonality (McGranahan et al., 2016), T cell repertoire analysis was performed using TCRb sequencing on a set of 60 tumors across all molecular subtypes (n=10 per group). It was found that, compared to genomically stable tumors, CDK12-mutant tumors showed higher overall levels of T cell infiltration (FIG. 6C) and larger numbers of expanded T cell clones (FIG. 6D), regardless of the template cutoff used (FIG. 14C). To confirm these trends across the entire cohort, T cell repertoire profiling of RNA-seq data was performed (Bolotin et al., 2015). First, it was established that RNA and DNA-based estimates of T cell infiltration were in agreement (FIG. 14D). It was found that relative to wild-type cases (PGD-WT), MMRD, HRD, and CDK12-mutant tumors all had a significant increase in both the number of detected T cell clones (FIG. 14E) and the total number of CDR3 sequences (FIG. 14F). Importantly, positive immunohistochemical (IHC) staining of CD3 on representative index cases further confirmed the presence of tumor-infiltrating T cells in a subset of CDK12-mutant tumors (FIG. 6E).

Figure 7A:
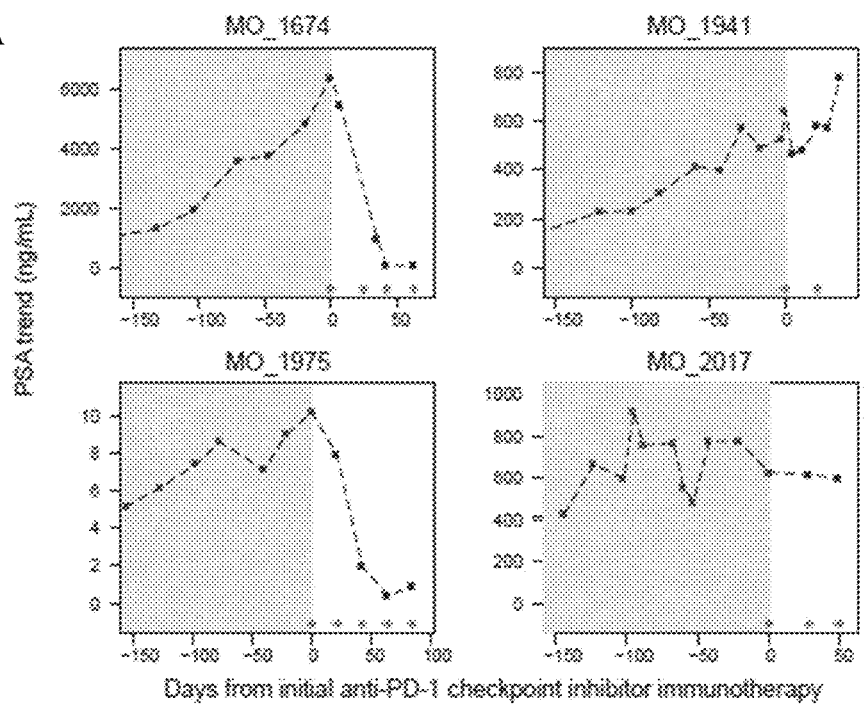
FIGS. 7A-C shows the response of CDK12-mutant patients to anti-PD-1 checkpoint inhibitor immunotherapy.

Clinical Study to Determine CDK12-Mutant Prostate Cancer Response to Checkpoint Inhibitor Immunotherapy Of eleven CDK12 mutant patients identified in the MI-Oncoseq Program at the University of Michigan (Robinson et al., 2017), a total of five late stage, pre-treated mCRPC patients to date have had some exposure to immunotherapy in the form of the immune checkpoint inhibitor anti-PD-1. One patient received one dose of anti-PD-1 as part of combination therapy on a clinical trial and was excluded, as he did not receive anti-PD-1 monotherapy and could, therefore, not be compared to the other treated patients. Detailed prostate-specific antigen (PSA) response data are presented on the four patients treated with anti-PD-1 monotherapy for whom associated clinical data and detailed sequencing information is available (FIG. 7A). Strikingly, two of the four patients had an exceptional response in terms of PSA decline. This was surprising as checkpoint inhibitor immunotherapy has typically not been efficacious in prostate cancer, with the exception of patients with mismatch repair defects (Le et al., 2015).

Figure 7B:
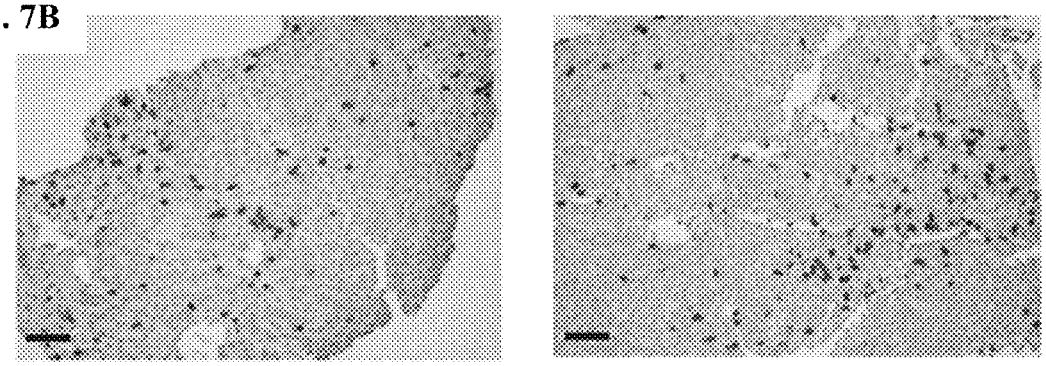
Figure 7C:
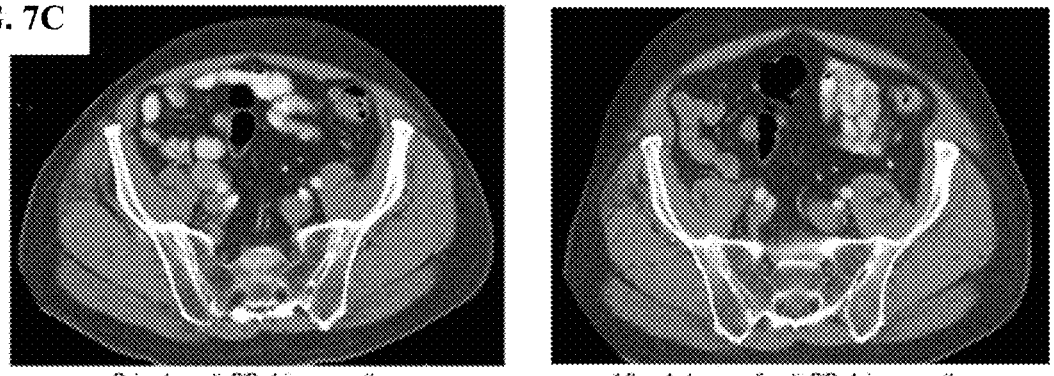

One patient (MO_1674) was treated with anti-PD-1 checkpoint inhibitor immunotherapy and displayed a marked PSA response after four doses of therapy, but eventually succumbed to multisystem organ failure, possibly due to anti-PD-I-induced pneumonitis (Nishino et al., 2015). Patient MO_1941 received only two doses of anti-PD-1 with a subsequently rising PSA and is deceased. Two patients are still alive on active therapy (MO_2017, MO_1975). Patient MO_2017 had heavily pre-treated disease, with prior disease progression on abiraterone, enzalutamide, docetaxel, and cabazitaxel. Pre-treatment PSA prior to initiation of immunotherapy was 628.8 ng/mL with a modest improvement in PSA after three doses of anti-PD-1, and subsequent PSA decline to 599.2 ng/mL. Patient MO_1975 had a Gleason 9 metastatic prostatic adenocarcinoma and prior lymph node progression on abiraterone and enzalutamide. Evaluation of a metastatic lymph node biopsy demonstrated robust CD3 staining by IHC (FIG. 7B). To date, the patient has received five doses of anti-PD-1 with a significant PSA decrement (FIG. 7A), as well as marked decline in pelvic lymph node disease burden (FIG. 7C). These early clinical results support the hypothesis that metastatic prostate cancer patients who harbor biallelic CDK12 loss have a higher likelihood of response to immunotherapy than an unselected metastatic prostate cancer population.

TABLE 1

| Case number | Biopsy site | Gleason Grade Primary | CDK12 status | CDK12 allele 1 | CDK12 allele 2 |
|---|---|---|---|---|---|
| 1 | Peritoneal nodule | 4 + 4 | mut | p.D52fs | p.S323* |
| 2 | Bone | 4 + 5 | mut | Copy loss | Copy loss |
| 3 | Liver | 4 + 4 | mut | p.P686fs | p.E189fs |
| 4 | Peritoneal mass | 4 + 3 | mut | p.Y279fs | Copy loss |
| 5 | Lymph node | 4 + 4 | mut | p.K757del | p.R902G |
| 6 | Lymph node | 4 + 5 | mut | ex5-12 internal rearrangement | Copy number breakpoint |
| 7 | Liver | NA | mut | p.R93fs | p.K186fs |
| 8 | Liver | 5 + 5 | mut | p.S625fs | Copy loss |
| 9 | Bone | 4 + 4 | mut | p.W960* | Copy loss |
| 10 | Lymph node | 4 + 4 | mut | p.R784* | C4B-CDK12 fusion |
| 11 | Lymph node | 4 + 3 | mut | p.P650fs | p.Y815fs |

TABLE 1-continued

| Case number | Biopsy site | Gleason Grade Primary | CDK12 status | CDK12 allele 1 | CDK12 allele 2 |
|---|---|---|---|---|---|
| 12 | Bone | NA | mut | CDK12-1p34.3 fusion | MACF1-CDK12 fusion |
| 13 | Lymph node | 4 + 5 | mut | p.Y319fs | LOH |
| 14 | Lymph node | 5 + 5 | mut | p.G923V | LOH |
| 15 | Lymph node | NA | mut | p.W1036* | Copy loss |
| 16 | Lymph node | 4 + 5 | mut | p.R858W | P.D918G |
| 17 | Soft tissue | 4 + 4 | mut | p.K493_D494fs | LOH |
| 18 | Lymph node | NA | mut | p.S377* | p.S318fs |
| 19 | Lymph node | NA | mut | p.R983* | LOH |
| 20 | Lymph node | NA | mut | p.V492fs, p.V492G | p.S476A, p.F426C |
| 21 | Lung | NA | mut | p.K232fs | Copy loss |
| 22 | Lymph node | NA | mut | RPAIN-CDK12 fusion | Copy loss |
| 23 | Mesentery | NA | mut | p.E405fs | LOH |
| 24 | Lymph node | NA | mut | p.P266fs | p.C952fs |
| 25 | Bone | 3 + 3 | mut | p.R99fs | Copy loss |

LOH: loss of heterozygosity
FH: frameshift
*truncation

TABLE 2

| Case | Metastatic/ Primary | Tandem Duplication Phenotype | CDK12 status | CDK12 allele 1 | CDK12 allele 2 |
|---|---|---|---|---|---|
| 1 | Metastatic | yes | mut | p.D52fs | p.S323* |
| 2 | Metastatic | yes | mut | Copy loss | Copy loss |
| 3 | Metastatic | yes | mut | p.P686fs | p.E189fs |
| 4 | Metastatic | yes | mut | p.Y279fs | Copy loss |
| 5 | Metastatic | yes | mut | p.K757del | Copy loss |
| 6 | Metastatic | yes | mut | ex5-12 splice | LOH/loss expression |
| 7 | Metastatic | yes | mut | p.R93fs | p.K186fs |
| 8 | Metastatic | yes | mut | p.S625* | Copy loss |
| 9 | Metastatic | yes | mut | p.W960* | Copy loss |
| 10 | Metastatic | yes | mut | p.R784* | C4B-CDK12 fusion |
| 11 | Metastatic | yes | mut | p.P650fs | p.Y815fs |
| 12 | Metastatic | yes | mut | CDK12-1p34.3 fusion | MACF1-CDK12 fusion |
| 13 | Metastatic | yes | mut | p.Y319fs | LOH |
| 14 | Metastatic | yes | mut | p.G923V | LOH |
| 15 | Metastatic | yes | mut | p.W1036* | Copy loss |
| 16 | Metastatic | yes | mut | p.R858W | p.D918G |
| 17 | Metastatic | yes | mut | p.K493_D494fs | LOH |
| 18 | Metastatic | yes | mut | p.S377X | p.S318fs |
| 19 | Metastatic | yes | mut | p.R983* | LOH |
| 20 | Metastatic | yes | mut | p.V492fs | p.S476A, p.F426C |
| 21 | Metastatic | yes | mut | p.K232fs | Copy loss |
| 22 | Metastatic | yes | mut | RPAIN-CDK12 fusion | Copy loss |
| 23 | Metastatic | yes | mut | p.E405fs | LOH |
| 24 | Metastatic | yes | mut | p.P266fs | p.C952fs |
| 25 | Metastatic | yes | mut | p.R99fs | Copy loss |
| TCGA-EJ-A46G | Primary | yes | mut | p.S343fs | p.R858W |
| TCGA-HC-8265 | Primary | yes | mut | p.Q598* | p.L55fs |
| TCGA-KK-A5A1 | Primary | yes | mut | p.T588fs | c.1046 + 1G > A Spl. don. |
| TCGA-KK-A8ID | Primary | yes | mut | p.L1003fs | p.E774K |
| TCGA-ZG-A9KY | Primary | yes | mut | p.T592fs | p.Q696* |
| TCGA-HC-A6HX | Primary | nd | subclonal | p.K217* | p.G909E |
| P-0004514 | Primary | nd | mut | p.E911Rfs | p.F83Sfs |
| P-0005445 | Primary | nd | mut | p.Q563* | p.I76Nfs*4 |
| P-0006574 | Primary | nd | mut | p.Y327* | p.Q740Kfs |

TABLE 3

| Study | Primary/ Metastatic | Sequencing Mode | Analysis Pipeline | # Cases | # Cases Biallelic CDK12 | % CDK12 Biallelic cases | Reference |
|---|---|---|---|---|---|---|---|
| MSKCC Impact | Primary | Targeted Panel | GATK/Mutect | 200 | 3 | 1.50% | Abida et al 2017 |
| PC Canada | Primary | Genomic | GATK/Somatic Sniper | 200 | 0 | 0% | Fraser et al 2017 |
| U Michigan | Primary | Exome | Mi-Oncoseq | 70 | 0 | 0% | unpublished |
| Primary Total | Primary | | | 470 | 3 | 0.6% | |

| Study | Primary/ Metastatic | Sequencing Mode | | # Cases | # Cases Biallelic CDK12 | % CDK12 Biallelic cases | Reference |
|---|---|---|---|---|---|---|---|
| Cornell | Metastatic | Exome | Firehose/Mutect | 77 | 4 | 5.2% | Beltran et al 2016 |
| U Washington Rapid Autopsy | Metastatic | Exome | GATK/Mutect | 54 | 3 | 5.6% | Kumar et al 2016 |
| MSKCC Impact | Metastatic | Targeted Panel | GATK/Mutect | 304 | 19 | 6.3% | Abida et al 2017 |
| Total | Metastatic | | | 435 | 26 | 6.0% | |

TABLE 4

| GENE | # Cases | Germline Alleles |
|---|---|---|
| CDK12 | 0 | |
| BRCA2 | 15 | p.L1491fs, p.S1882*, p.S1982fs, p.K1057fs, p.N1784fs, p.K1530*, p.T2891fs, p.I1516fs, p.E1493fs, p.T2968fs, p.S1955*, p.S1882*, p.L698fs, p.T1738fs, (p.R2784W, p.K2950N) |
| BRCA1 | 3 | Spl. acc. c.5075 − 1G > A, p.Q1756fs, p.Q1756fs |
| PALB2 | 2 | p.R34fs, p.S1169fs |
| ATM | 7 | p.V1268fs, p.W2638*, p.Q1970fs, p.W2769*, p.G1458fs, Spl. acc. c.7630 − 2A > C, p.K2756* |

TABLE 5

| gene_name | gene_id | siCDK12_logFC | siCDK12_fdr | mutCDK12_logFC | mutCDK12_fdr |
|---|---|---|---|---|---|
| AIFM2 | ENSG00000042286.14 | 1.879519081 | 2.03E−10 | 1.440739811 | 6.15E−14 |
| TSACC | ENSG00000163467.11 | −1.184855628 | 4.31E−07 | −2.453260429 | 4.06E−13 |
| ARID3C | ENSG00000205143.2 | 1.276621651 | 3.12E−07 | 2.490574012 | 5.47E−11 |
| ATP6V1E2 | ENSG00000250565.6 | −2.238301527 | 1.48E−13 | −1.570399307 | 1.03E−10 |
| MRPL24 | ENSG00000143314.12 | −0.678237446 | 6.20E−09 | −1.313778431 | 2.57E−10 |
| CDNF | ENSG00000185267.9 | −1.324039481 | 2.22E−06 | −1.994030672 | 3.36E−10 |
| PIGM | ENSG00000143315.6 | −0.624187187 | 3.16E−10 | −1.093993012 | 1.00E−09 |
| CCDC110 | ENSG00000168491.9 | −0.802784662 | 1.24E−07 | −1.830993216 | 1.00E−09 |
| MLN | ENSG00000096395.10 | 3.806662676 | 1.74E−06 | 2.634749456 | 1.75E−09 |
| FCRL6 | ENSG00000181036.13 | 2.662766844 | 0.003558595 | 2.242893704 | 4.70E−09 |
| EHHADH | ENSG00000113790.10 | −2.285739786 | 5.24E−10 | −1.776286008 | 1.33E−08 |
| CATSPERB | ENSG00000133962.7 | −1.863944426 | 1.15E−06 | −2.642883345 | 1.34E−08 |
| PLAC8L1 | ENSG00000173261.8 | −2.255970466 | 7.09E−05 | −2.27848062 | 1.53E−08 |
| ORMDL2 | ENSG00000123353.9 | −0.806251621 | 1.30E−08 | −1.43136845 | 1.96E−08 |
| CHMP2A | ENSG00000130724.8 | −0.638689057 | 2.50E−08 | −0.915876758 | 1.96E−08 |
| TEX22 | ENSG00000226174.6 | 0.729385646 | 0.000345213 | 1.485687772 | 6.41E−08 |
| RP4-816N1.8 | ENSG00000283297.1 | −2.623467868 | 4.94E−07 | −2.144730079 | 9.90E−08 |
| TCP10L | ENSG00000242220.6 | −2.72707259 | 0.000132401 | −1.888962137 | 1.03E−07 |
| ANKK1 | ENSG00000170209.4 | −3.747545624 | 2.17E−05 | −2.613458992 | 1.45E−07 |
| TMEM141 | ENSG00000244187.7 | −0.741911884 | 1,17E−07 | −1.532389349 | 1.96E−07 |
| PIP5KL1 | ENSG00000167103.11 | 0.761657631 | 0.000100474 | 1.548630418 | 2.87E−07 |
| SPA17 | ENSG00000064199.6 | −1.078413255 | 1.53E−07 | −1.543132077 | 8.29E−07 |
| KIAA1683 | ENSG00000130518.16 | 1.359154758 | 1.30E−09 | 1.730509005 | 8.29E−07 |
| IQCG | ENSG00000114473.13 | −1.053096322 | 1.36E−11 | −1.08021186 | 1.00E−06 |
| TAS2R5 | ENSG00000127366.5 | −3.9386994.35 | 1.06E−08 | −1.915846892 | 1.10E−06 |
| NPHP1 | ENSG00000144061.12 | −0.637202839 | 6.81E−07 | −1.139003082 | 1.63E−06 |
| YY2 | ENSG00000230797.2 | 0.856106692 | 3.20E−09 | 1.082975405 | 1.63E−06 |
| ORC3 | ENSG00000135336.14 | −1.41640793 | 2.76E−10 | −0.994212079 | 1.65E−06 |
| TLCD1 | ENSG00000160606.10 | −1.527912582 | 9.57E−11 | −1.538348803 | 1.68E−06 |
| TAS1R3 | ENSG00000169962.4 | 0.595950714 | 0.001139393 | 1.376068068 | 1.77E−06 |
| CHRND | ENSG00000135902.9 | 1.327325967 | 0.0093624 | 2.455212147 | 1.79E−06 |

TABLE 5-continued

| gene_name | gene_id | siCDK12_logFC | siCDK12_fdr | mutCDK12_logFC | mutCDK12_fdr |
|---|---|---|---|---|---|
| CCDC113 | ENSG00000103021.9 | −0.773044577 | 1.22E−09 | −1.544856217 | 1.82E−06 |
| KCNAB3 | ENSG00000170049.9 | 0.708896585 | 1.49E−05 | 1.354753233 | 1.86E−06 |
| HGFAC | ENSG00000109758.8 | 2.800353094 | 3.19E−07 | 2.18744972 | 3.78E−06 |
| CEACAM19 | ENSG00000186567.12 | −1.187399834 | 0.000246891 | −1.761616096 | 4.18E−06 |
| OMA1 | ENSG00000162600.11 | −0.589957163 | 3.82E−09 | −1.012328787 | 4.28E−06 |
| MSH5 | ENSG00000204410.14 | −0.980874764 | 1.92E−11 | −1.42030434 | 4.97E−06 |
| OR2A14 | ENSG00000221938.4 | 1.372446876 | 0.003153874 | 2.251077657 | 6.26E−06 |
| HOXA4 | ENSG00000197576.13 | 0.594970908 | 0.009721068 | 1.352167147 | 8.95E−06 |
| FSCN3 | ENSG00000106328.9 | 1.208458215 | 0.000308738 | 1.802174764 | 8.97E−06 |
| TAS2R4 | ENSG00000127364.3 | −3.229149017 | 5.76E−07 | −1.876528019 | 8.97E−06 |
| IL11 | ENSG00000095752.6 | 1.441557051 | 5.28E−08 | 1.733998613 | 1.07E−05 |
| SAPCD1 | ENSG00000228727.8 | −1.279389007 | 6.44E−08 | −1.645067942 | 1.15E−05 |
| DOK7 | ENSG00000175920.16 | 0.831164561 | 0.001069411 | 1.597830088 | 1.30E−05 |
| NOXRED1 | ENSG00000165555.9 | −1.218264032 | 6.37E−05 | −1.288673112 | 1.43E−05 |
| HERC6 | ENSG00000138642.16 | −0.598673585 | 9.41E−05 | −1.482964403 | 1.49E−05 |
| WNT3A | ENSG00000154342.5 | 2.444771485 | 2.29E−05 | 2.085857965 | 1.64E−05 |
| TMEM256 | ENSG00000205544.3 | −0.912248337 | 1.13E−08 | −1.541704301 | 1.72E−05 |
| SLC7A9 | ENSG00000021488.12 | −1.793496236 | 0.002327588 | −1.552313156 | 1.80E−05 |
| SLC13A3 | ENSG00000158296.13 | −0.6834540.31 | 3.31E−06 | −1.89786652 | 2.60E−05 |
| HSD17B8 | ENSG00000204228.3 | −0.712685357 | 2.86E−07 | −1.248053063 | 2.94E−05 |
| UCN | ENSG00000163794.6 | −0.66835161 | 0.001252042 | −1.519918336 | 3.04E−05 |
| WDR5B | ENSG00000196981.3 | −0.591719235 | 1.92E−10 | −0.850167199 | 3.14E−05 |
| ZNF165 | ENSG00000197279.3 | 0.756146442 | 1.70E−08 | 1.00960903 | 3.98E−05 |
| MEF2B | ENSG00000213999.15 | −1.323144969 | 1.68E−07 | −1.042176725 | 3.98E−05 |
| TM2D1 | ENSG00000162604.12 | −0.727515936 | 1.20E−09 | −0.81958186 | 4.05E−05 |
| CSTF3 | ENSG00000176102.11 | −0.796507986 | 3.83E−12 | −0.625502964 | 4.93E−05 |
| THADA | ENSG00000115970.18 | −0.747657697 | 3.00E−09 | −0.765418748 | 5.55E−05 |
| GPR143 | ENSG00000101850.12 | 1.922043391 | 5.52E−09 | 1.338608458 | 6.38E−05 |
| VEPH1 | ENSG00000197415.11 | −0.706683263 | 0.009107947 | 1.642649648 | 7.47E−05 |
| CDK12 | ENSG00000167258.13 | −2.235756028 | 2.67E−18 | −0.638381968 | 8.66E−05 |
| CFAP70 | ENSG00000156042.17 | −1.0817732 | 4.57E−08 | −1.429024384 | 0.000115516 |
| TMEM223 | ENSG00000168569.7 | −0.598092106 | 1.07E−09 | −0.849574222 | 0.000124819 |
| MAP2 | ENSG00000078018.19 | 1.077905425 | 2.74E−07 | 1.66555484 | 0.000131813 |
| PCDHB12 | ENSG00000120328.6 | 0.606990392 | 0.003444292 | 1.14244882 | 0.000139288 |
| RFPL1 | ENSG00000128250.3 | −2.297473363 | 0.004081803 | −2.456024609 | 0.000157468 |
| IGFL4 | ENSG00000204869.8 | −1.217119064 | 0.004412598 | −1.661637375 | 0.000157528 |
| TMEM5 | ENSG00000118600.11 | −1.072592345 | 1.26E−11 | −0.904443551 | 0.000171654 |
| UFSP1 | ENSG00000176125.4 | −0.90962217 | 4.15E−07 | −0.951900276 | 0.000172699 |
| DEGS2 | ENSG00000168350.7 | 0.80324377 | 0.001029264 | 1.473828538 | 0.000183242 |
| SPACA4 | ENSG00000177202.2 | 1.845474649 | 2.67E−06 | 2.103806635 | 0.000187498 |
| DQX1 | ENSG00000144045.13 | −0.622532604 | 6.98E−06 | 1.560630777 | 0.000206993 |
| CFAP54 | ENSG00000188596.10 | 1.675083788 | 5.37E−06 | −1.770197452 | 0.000206993 |
| KIAA1456 | ENSG00000250305.8 | 2.966391586 | 0.000959335 | 1.614005688 | 0.000214973 |
| ARHGEF33 | ENSG00000214694.10 | −1.753347182 | 0.005295814 | −1.32258665 | 0.000215557 |
| ZC3H10 | ENSG00000135482.6 | −0.806206034 | 1.39E−06 | −0.667839276 | 0.000230211 |
| ABHD11 | ENSG00000106077.18 | −0.680346156 | 1.13E−08 | −1.033036644 | 0.00023653 |
| SPRYD4 | ENSG00000176422.13 | −0.657222528 | 1.94E−08 | −0.652498162 | 0.000274154 |
| HNF4G | ENSG00000164749.11 | 1.334799915 | 0.006228263 | 2.020689785 | 0.000303252 |
| GPR152 | ENSG00000175514.2 | 2.215245283 | 9.29E−05 | 1.487158198 | 0.000303252 |
| ELOA3B | ENSG00000278674.1 | 1.786127464 | 0.002031936 | 1.526522985 | 0.000303252 |
| GDPGP1 | ENSG00000183208.12 | −0.795396854 | 7.75E−07 | −0.643451849 | 0.000312262 |
| PPEF1 | ENSG00000086717.18 | −1.08792917 | 0.000688199 | −1.952138216 | 0.000328993 |
| SERPINE3 | ENSG00000253309.6 | −2.112801276 | 2.07E−06 | −1.401494589 | 0.000336299 |
| MUC20 | ENSG00000176945.16 | −1.744514048 | 6.89E−07 | −2.01234768 | 0.000336927 |
| BMX | ENSG00000102010.14 | 1.145704211 | 5.49E−05 | 1.740669235 | 0.00035684 |
| SNAPIN | ENSG00000143553.10 | −0.92060831 | 1.05E−07 | −0.945758243 | 0.000363348 |
| CFAP206 | ENSG00000272514.5 | 1.050267897 | 2.54E−05 | −1.481500152 | 0.000379926 |
| ELOA2 | ENSG00000206181.5 | 1.948834685 | 0.000938576 | 1.401943376 | 0.000402171 |
| IZUMO1 | ENSG00000182264.8 | 1.014237575 | 0.000272375 | 1.395376953 | 0.000403666 |
| MRPL53 | ENSG00000204822.6 | −0.611262999 | 2.98E−08 | −0.881912529 | 0.000408563 |
| ZNF354C | ENSG00000177932.6 | 0.591340938 | 1.44E−08 | 0.891418657 | 0.000413773 |
| PMFBP1 | ENSG00000118557.15 | −3.071154747 | 4.22E−06 | −1.600501123 | 0.000415436 |
| TAF10 | ENSG00000166337.9 | −0.666382651 | 4.30E−09 | −0.702478094 | 0.000420277 |
| SPATA17 | ENSG00000162814.10 | −1.165296027 | 2.82E−07 | −1.255773817 | 0.000423311 |
| GUCA1B | ENSG00000112599.8 | −1.999273407 | 0.00213315 | −1.435776835 | 0.000434327 |
| ZNF425 | ENSG00000204947.8 | 1.098776545 | 1.36E−11 | 0.858464107 | 0.000434327 |
| DRICH1 | ENSG00000189269.12 | −2.566725651 | 1.34E−06 | −1.451867802 | 0.000474875 |
| CACNA1G | ENSG00000006283.17 | 0.760493742 | 0.00202759 | −2.720825985 | 0.000564985 |
| CBLN3 | ENSG00000139899.6 | 0.871572905 | 3.02E−05 | 0.971495382 | 0.000592374 |
| ARHGEF25 | ENSG00000240771.6 | 0.827415685 | 1.00E−07 | 0.898587013 | 0.000596262 |
| C19orf18 | ENSG00000177025.3 | −1.463901171 | 8.18E−06 | −1.293688741 | 0.000618627 |
| PEPD | ENSG00000124299.13 | −0.756031092 | 6.55E−07 | −0.642326089 | 0.000686614 |
| C17orf107 | ENSG00000205710.3 | −0.729794736 | 6.87E−05 | −1.327083178 | 0.000731865 |
| TMEM63C | ENSG00000165548.10 | −0.775022067 | 1.99E−10 | −2.684262181 | 0.000788484 |
| DFNB59 | ENSG00000204311.12 | 1.059184034 | 2.65E−05 | 0.983239158 | 0.000806357 |
| PKD1L3 | ENSG00000277481.1 | 0.715067715 | 0.008155191 | 1.139545032 | 0.000829061 |
| TAS2R3 | ENSG00000127362.2 | −3.159356625 | 1.27E−07 | −1.384139682 | 0.000834549 |
| COL28A1 | ENSG00000215018.9 | −1.291559514 | 0.002172678 | −1.801846237 | 0.000866231 |

TABLE 5-continued

| gene_name | gene_id | siCDK12_logFC | siCDK12_fdr | mutCDK12_logFC | mutCDK12_fdr |
|---|---|---|---|---|---|
| DNAH1 | ENSG00000114841.17 | −1.490060672 | 1.61E−12 | −1.066097695 | 0.0009027 |
| ATAD3C | ENSG00000215915.9 | 0.894310406 | 0.00193322 | 1.475441647 | 0.000913331 |
| ZSWIM5 | ENSG00000162415.6 | 0.82626835 | 1.15E−05 | 0.770971854 | 0.000997778 |
| ZFP2 | ENSG00000198939.7 | 1.551862219 | 1.45E−06 | 0.866789405 | 0.001001451 |
| SYT2 | ENSG00000143858.11 | −0.868274083 | 0.004347183 | −1.179996971 | 0.00103857 |
| TTC30A | ENSG00000197557.6 | −0.894476611 | 3.06E−12 | −0.870144163 | 0.001044458 |
| C5 | ENSG00000106804.7 | 1.01747408 | 6.25E−05 | 0.989706112 | 0.001080916 |
| ZNF362 | ENSG00000160094.14 | 0.744647878 | 2.47E−08 | 0.735955021 | 0.001087173 |
| C19or35 | ENSG00000188305.5 | 1.193961078 | 0.000395833 | 1.116615035 | 0.001092852 |
| ZNF546 | ENSG00000187187.13 | −0.76459412.3 | 6.10E−09 | −0.825904884 | 0.001134145 |
| ARL6IP5 | ENSG00000144746.6 | −0.636359636 | 2.44E−09 | −0.875846543 | 0.001144531 |
| HSF2BP | ENSG00000160207.8 | 0.839964831 | 2.82E−07 | 0.902768756 | 0.001172771 |
| PM20D1 | ENSG00000162877.12 | 2.88194169 | 3.19E−06 | 1.415538472 | 0.001311569 |
| AK7 | ENSG00000140057.8 | −0.754891429 | 4.09E−06 | −1.286523966 | 0.001490555 |
| CDHR3 | ENSG00000128536.15 | 1.066652966 | 0.000182933 | −1.753425178 | 0.00164901 |
| KCNV2 | ENSG00000168263.8 | −2.021132442 | 2.45E−05 | −1.413966206 | 0.001674429 |
| VMO1 | ENSG00000182853.11 | 0.790649134 | 0.000162945 | 0.944026457 | 0.001674429 |
| FAM71F1 | ENSG00000135248.15 | −3.18120648 | 0.000273478 | −1.728965223 | 0.001681611 |
| PKHD1 | ENSG00000170927.14 | −0.720208891 | 0.006481338 | 2.041087209 | 0.00171436 |
| ZRANB3 | ENSG00000121988.17 | −1.059493313 | 1.16E−08 | −0.745118223 | 0.001814199 |
| CD24 | ENSG00000272398.5 | 1.091019863 | 0.007428721 | −1.593462777 | 0.001876961 |
| PROX2 | ENSG00000119608.12 | −1.617298409 | 1.17E−07 | −1.098358665 | 0.001882347 |
| DNAH10OS | ENSG00000250091.2 | 1.78495914 | 1.43E−07 | 1.06752169 | 0.002004913 |
| CHST5 | ENSG00000135702.14 | −1.062133298 | 6.57E−05 | −1.128995633 | 0.002097932 |
| TMEM99 | ENSG00000167920.8 | −0.645671476 | 1.18E−06 | −0.838952205 | 0.002149237 |
| UPP1 | ENSG00000183696.13 | 0.606895026 | 0.00108119 | 0.829574979 | 0.002207276 |
| GOLT1A | ENSG00000174567.7 | 0.611780983 | 6.85E−06 | 1.339765058 | 0.002215009 |
| CD200R1 | ENSG00000163606.10 | 3.424464166 | 4.80E−07 | 1.11068945 | 0.002230544 |
| MSLNL | ENSG00000162006.9 | 1.18413124 | 0.003490302 | 1.586578852 | 0.002264283 |
| DRAM2 | ENSG00000156171.14 | −0.644491678 | 2.22E−06 | −0.660504818 | 0.002327039 |
| MLANA | ENSG00000120215.9 | −1.878426027 | 0.000146781 | −0.971148704 | 0.002416583 |
| ZYG11A | ENSG00000203995.9 | 0.886074086 | 3.81E−05 | −1.969000489 | 0.002435599 |
| PRELID2 | ENSG00000186314.11 | 0.783294771 | 0.005409106 | 1.071051681 | 0.002463021 |
| EPHX3 | ENSG00000105131.7 | 1.160953244 | 0.003450724 | 1.134785162 | 0.002529984 |
| MROH6 | ENSG00000204839.8 | 0.856710074 | 0.000849999 | 1.16005568 | 0.002549909 |
| ADCY7 | ENSG00000121281.12 | 0.646503452 | 3.97E−06 | 0.875529534 | 0.002594101 |
| ANKRD24 | ENSG00000089847.12 | −0.692448479 | 1.87E−05 | −1.328816761 | 0.002622581 |
| GPR45 | ENSG00000135973.2 | 1.153319345 | 0.004087188 | 1.157821503 | 0.002687235 |
| CD99L2 | ENSG00000102181.20 | 0.683775898 | 4.81E−07 | 0.619459707 | 0.00271164 |
| C2orf72 | ENSG00000204128.5 | 0.751175255 | 4.17E−06 | 1.738417811 | 0.002775021 |
| PEX6 | ENSG00000124587.13 | 0.632377582 | 6.71E−09 | 0.631231108 | 0.002868852 |
| OSBPL5 | ENSG00000021762.19 | −1.229818108 | 1.48E−13 | −0.733231138 | 0.002909334 |
| MFRP | ENSG00000235718.8 | 2.35067394 | 0.003907964 | 1.434351678 | 0.002925285 |
| IQCK | ENSG00000174628.16 | −0.750063467 | 7.51E−07 | −0.641248661 | 0.003017081 |
| MSLN | ENSG00000102854.15 | 1.832528102 | 1.41E−05 | 1.427729103 | 0.003149712 |
| SLC25A11 | ENSG00000108528.13 | −0.614164104 | 4.31E−08 | −0.632489424 | 0.003149712 |
| DHX58 | ENSG00000108771.12 | 0.651962457 | 6.28E−05 | −0.790594204 | 0.003195059 |
| SLC6A6 | ENSG00000131389.16 | −0.791368354 | 6.20E−09 | 1.012196337 | 0.003286972 |
| COX7B2 | ENSG00000170516.16 | 0.714932692 | 4.99E−05 | −2.313861649 | 0.003343096 |
| GPC5 | ENSG00000179399.14 | 0.593119652 | 0.004374358 | 1.528228002 | 0.003408768 |
| C6orf10 | ENSG00000204296.11 | 1.859162385 | 0.002541855 | −1.988389855 | 0.003519384 |
| NSF | ENSG00000073969.18 | −0.697408817 | 2.12E−08 | −0.64892243 | 0.003708003 |
| FUT7 | ENSG00000180549.7 | 1.000089992 | 0.000157679 | 1.168686665 | 0.003732722 |
| MAMDC4 | ENSG00000177943.13 | 0.9031771 | 0.000241363 | 0.992626405 | 0.003845038 |
| USP17L7 | ENSG00000226430.6 | 2.108025118 | 0.003548582 | 1.873664866 | 0.003920919 |
| F7 | ENSG00000057593.13 | 2.233617763 | 0.000320817 | 1.563292987 | 0.003991489 |
| ZCWPW1 | ENSG00000078487.17 | −0.74929388 | 0.000126683 | −0.841436044 | 0.004033683 |
| H2AFJ | ENSG00000246705.4 | −0.82953934 | 3.11E−08 | −0.946988081 | 0.004033683 |
| ZNF117 | ENSG00000152926.14 | 2.245983801 | 2.37E−07 | 0.999615422 | 0.004146604 |
| CCDC166 | ENSG00000255181.3 | 1.269841789 | 0.000948786 | 1.526892253 | 0.00427561 |
| FAM109B | ENSG00000177096.8 | 1.112414055 | 0.005091236 | −1.071459092 | 0.004577788 |
| LRRC17 | ENSG00000128606.12 | −1.939284573 | 0.001685033 | −1.075457932 | 0.004712221 |
| TTC29 | ENSG00000137473.17 | −1.581063508 | 0.000334949 | −1.883552714 | 0.004805117 |
| NBPF3 | ENSG00000142794.18 | 0.750443152 | 0.000469571 | 0.854368404 | 0.0048411 |
| ACTN3 | ENSG00000248746.5 | 0.988605499 | 0.000129117 | 1.446869263 | 0.004966393 |
| CDHR2 | ENSG00000074276.10 | 0.975258113 | 6.33E−05 | 1.228888765 | 0.005003667 |
| SBSN | ENSG00000189001.10 | 1.793611569 | 1.71E−05 | 1.683890512 | 0.005125242 |
| F10 | ENSG00000126218.11 | 1.284074748 | 2.16E−09 | 0.994000049 | 0.005470999 |
| BBS12 | ENSG00000181004.9 | 0.825335518 | 1.29E−06 | 0.681141934 | 0.005509791 |
| RPRD1A | ENSG00000141425.17 | −1.248937336 | 3.29E−14 | −0.611133719 | 0.005697626 |
| CDRT1 | ENSG00000241322.10 | −2.637089081 | 2.24E−06 | −1.365944479 | 0.005771102 |
| PTGS1 | ENSG00000095303.14 | −0.788887123 | 0.00348485 | 0.798970229 | 0.005813369 |
| LAG3 | ENSG00000089692.8 | 1.411015045 | 1.68E−07 | 0.902316846 | 0.006082485 |
| RNF212B | ENSG00000215277.8 | 2.11314631 | 1.79E−06 | 1.170505903 | 0.006200233 |
| SIX1 | ENSG00000126778.8 | 0.689214159 | 1.21E−05 | −1.038080475 | 0.006288684 |
| DOK3 | ENSG00000146094.13 | 0.813309806 | 0.000761998 | 0.820139436 | 0.006358413 |
| DOK4 | ENSG00000125170.10 | 0.83147481 | 1.68E−07 | 0.637735163 | 0.006520341 |
| CDRT4 | ENSG00000239704.10 | −2.093940448 | 2.30E−09 | −0.864905412 | 0.007380727 |

TABLE 5-continued

| gene_name | gene_id | siCDK12_logFC | siCDK12_fdr | mutCDK12_logFC | mutCDK12_fdr |
|---|---|---|---|---|---|
| CYP7A1 | ENSG00000167910.3 | 2.939054482 | 8.56E−05 | 1.680177687 | 0.007390031 |
| FBXL13 | ENSG00000161040.16 | −0.902216649 | 0.00043439 | −0.724405668 | 0.007443914 |
| NEK11 | ENSG00000114670.13 | −1.140132825 | 1.09E−07 | −0.746020333 | 0.007520846 |
| ERICH6 | ENSG00000163645.14 | 0.938800779 | 0.007530765 | −0.977913303 | 0.007588979 |
| DRD4 | ENSG00000069696.6 | −0.885802096 | 0.000240664 | −1.213877663 | 0.008116405 |
| RIN1 | ENSG00000174791.10 | 1.219521559 | 0.000491373 | 0.745225233 | 0.008116405 |
| POLN | ENSG00000130997.16 | −1.18042.1069 | 0.000138297 | −0.895499056 | 0.008663576 |
| CFAP44 | ENSG00000206530.10 | −0.746417053 | 1.76E−05 | −0.859400505 | 0.009099029 |
| LRRC23 | ENSG00000010626.14 | −0.646704045 | 1.22E−08 | −0.597718865 | 0.00914321 |
| GNG4 | ENSG00000168243.10 | 1.076245376 | 1.22E−05 | −2.158491667 | 0.00930353 |
| SDC4 | ENSG00000124145.6 | −0.713680533 | 1.25E−06 | −1.055866912 | 0.009407331 |
| ZNF404 | ENSG00000176222.8 | −0.890084838 | 0.000774957 | −0.926138306 | 0.00942192 |
| WNT3 | ENSG00000108379.9 | 0.963230485 | 1.36E−06 | 0.824242824 | 0.009854116 |

REFERENCES

Abida, W., Armenia. J., Gopalan, A., Brennan, R., Walsh, M., Barron, D., Danila, D., Rathkopf, D., Morris, M., Slovin, S., et al. (2017). Prospective genomic profiling of prostate cancer across disease states reveals germline and somatic alterations that may affect clinical decision making. JCO Precis Oncol 2017.

Alexandrov, L. B., Nik-Zainal, S., Wedge, D. C., Aparicio, S. A., Behjati, S., Biankin, A. V., Bignell, G. R., Bolli, N., Borg, A., Borresen-Dale, A L., et al. (2013). Signatures of mutational processes in human cancer. Nature 500, 415-421.

Ashworth, A., Lord, C. J., and Reis-Filho, J. S. (2011). Genetic interactions in cancer progression and treatment. Cell 145, 30-38.

Bajrami, I., Frankum, J. R., Konde, A., Miller, R. E., Rehman, F. L., Brough. R., Campbell, J., Sims, D., Rafiq, R., Hooper, S., et al. (2014). Genome-wide profiling of genetic synthetic lethality identifies CDK12 as a novel determinant of PARPl/2 inhibitor sensitivity. Cancer Res 74, 287-297.

Barbieri, C. E., Baca, S. C., Lawrence, M. S., Demichelis, F., Blattner, M., Theurillat, J.-P., White, T. A., Stojanov, P., Van Allen, E., Stransky, N., et al. (2012). Exome sequencing identifies recurrent SPOP, FOXA1 and MED12 mutations in prostate cancer. Nat Genet 44, 685-689.

Bartkowiak, B., Liu, P., Phatnani. H. P., Fuda, N. J., Cooper, J. J., Price, D. H., Adelman, K., Lis, J. T., and Greenleaf. A. L. (2010). CDK12 is a transcription elongation-associated CTD kinase, the metazoan ortholog of yeast Ctk1. Genes Dev 24, 2303-2316.

Beltran, H., Prandi, D., Mosquera. J. M., Benelli, M., Puca, L., Cyrta. J., Marotz. C., Giannopoulou, E., Chakravarthi, B. V. S. K., Varambally, S., et al. (2016). Divergent clonal evolution of castration-resistant neuroendocrine prostate cancer. Nat Med 22, 298-305.

Bernard, D., Pourtier-Manzanedo, A., Gil, J., and Beach, D. H. (2003). Myc confers androgen-independent prostate cancer cell growth. J Clin Invest 112, 1724-1731.

Blazek, D., Kohoutek, J., Bartholomeeusen, K., Johansen, E., Hulinkova, P., Luo, Z., Cimermancic, P., Ule, J., and Peterlin, B. M. (2011). The Cyclin K/Cdk12 complex maintains genomic stability via regulation of expression of DNA damage response genes. Genes Dev 25, 2158-2172.

Bolotin, D. A., Poslavsky, S., Mitrophanov, I., Shugay, M., Mamedov, I. Z., Putintseva. E. V., and Chudakov, D. M. (2015). MiXCR: software for comprehensive adaptive immunity profiling. Nat Meth 12, 380-381.

Bretones, G., Delgado, M. D., and Leon, J. (2015). Myc and cell cycle control. Biochim Biophys Acta 1849, 506-516.

Cabel, L., Loir, E., Gravis, G., Lavaud, P., Massard, C., Albiges, L., Baciarello, G., Loriot, Y., and Fizazi, K. (2017). Long-term complete remission with ipilimumab in metastatic castrate-resistant prostate cancer: case report of two patients. J Immunother Cancer 5, 31.

Chan, V. W. F., Kothakota, S., Rohan. M. C., Panganiban-Lustan, L., Gardner. J. P., Wachowicz, M. S., Winter, J. A., and Williams, L. T. (1999). Secondary lymphoid-tissue chemokine (SLC) is chemotactic for mature dendritic cells. Blood 93, 3610-3616.

Chen, Y., Wang, J., Fraig, M. M., Metcalf, J., Turner, W. R., Bissada, N. K., Watson, D. K., and Schweinfest. C. W. (2001). Defects of DNA mismatch repair in human prostate cancer. Cancer Res 61, 4112-4121.

Cheng, S. W., Kuzyk, M. A., Moradian, A., Ichu, T. A., Chang, V. C., Tien, J. F., Vollett. S. E., Griffith, M., Marra, M. A., and Morin, G. B. (2012). Interaction of cyclin-dependent kinase 12/CrkRS with cyclin K1 is required for the phosphorylation of the C-terminal domain of RNA polymerase II. Mol Cell Biol 32, 4691-4704.

Cieslik, M., Chugh, R., Wu, Y. M., Wu, M., Brennan, C., Lonigro, R., Su, F., Wang, R., Siddiqui, J., Mehra, R., et al. (2015). The use of exome capture RNA-seq for highly degraded RNA with application to clinical cancer sequencing. Genome Res 25, 1372-1381.

Curiel, T. J., Coukos, G., Zou, L., Alvarez, X., Cheng, P., Mottram, P., Evdemon-Hogan, M., Conejo-Garcia, J. R. Zhang, L., Burow, M., et al. (2004). Specific recruitment of regulatory T cells in ovarian carcinoma fosters immune privilege and predicts reduced survival. Nat Med 10, 942-949.

Cutruzzola, F., Giardina, G., Marani, M., Macone, A., Paiardini, A., Rinaldo, S., and Paone, A. (2017). Glucose metabolism in the progression of prostate cancer. Front Physiol 8, 97.

Durinck, S., Moreau, Y., Kasprzyk, A., Davis, S., De Moor, B., Brazma, A., and Huber, W. (2005). BioMart and Bioconductor: a powerful link between biological databases and microarray data analysis. Bioinformatics 21, 3439-3440.

Ekumi, K. M., Paculova, H., Lenasi, T., Pospichalova, V., Bösken, C. A., Rybarikova, J., Bryja, V., Geyer, M., Blazek, D., and Barboric, M. (2015). Ovarian carcinoma CDK12 mutations misregulate expression of DNA repair genes via deficient formation and function of the Cdkl2/CycK complex. Nucleic Acids Res 43, 2575-2589.

Fraser, M., Sabelnykova, V. Y., Yamaguchi, T. N., Heisler, L. E., Livingstone, J., Huang, V., Shiah, Y.-J., Yousif, F., Lin, X., Masella, A. P., et al. (2017). Genomic hallmarks of localized, non-indolent prostate cancer. Nature 541, 359-364.

Gehring, J. S., Fischer, B., Lawrence, M., and Huber, W. (2015). SomaticSignatures: inferring mutational signatures from single-nucleotide variants. Bioinformatics 31, 3673-3675.

Gosling, J., Dairaghi, D. J., Wang, Y., Hanley. M., Talbot, D., Miao, Z., and Schall. T. J. (2000). Cutting edge: identification of a novel chemokine receptor that binds dendritic cell- and T cell-active chemokines including ELC, SLC, and TECK. J Immunol 164, 2851-2856.

Graff J. N., Alumkal, J. J., Drake, C. G., Thomas. G. V., Redmond. W. L., Farhad, M., Cetnar, J. P., Ey, F. S., Bergan, R. C., Slottke, R, et al. (2016). Early evidence of anti-PD-1 activity in enzalutamide-resistant prostate cancer. Oncotarget 7, 52810-52817.

Grasso, C. S., Wu, Y.-M., Robinson, D. R., Cao, X., Dhanasekaran, S. M., Khan, A. P., Quist, M. J., Jing, X., Lonigro, R. J., Brenner, J. C., et 71. (2012). The mutational landscape of lethal castration-resistant prostate cancer. Nature 487, 239-243.

Hacohen, N., Fritsch, E. F., Carter, T. A., Lander, E. S., and Wu, C. R. (2013). Getting personal with neoantigen-based therapeutic cancer vaccines. Cancer Immunol Res 1, 11-15.

Herschkowitz, J. I., He, X., Fan, C., and Perou, C. M. (2008). The functional loss of the retinoblastoma tumour suppressor is a common event in basal-like and luminal B breast carcinomas. Breast Cancer Res 10, R75.

Hiratani, I., Ryba, T., Itoh, M., Yokochi, T., Schwaiger, M., Chang, C. W., Lyou, Y., Townes, T. M., Schubeler, D., and Gilbert, D. M. (2008). Global reorganization of replication domains during embryonic stem cell differentiation. PLoS Biol 6, e245.

Ito, K., and Suda. T. (2014). Metabolic requirements for the maintenance of self-renewing stem cells. Nat Rev Mol Cell Biol 15, 243-256.

Joshi, P. M., Sutor, S. L., Huntoon, C. J., and Kamitz, L. M. (2014). Ovarian cancer-associated mutations disable catalytic activity of CDK12, a kinase that promotes homologous recombination repair and resistance to cisplatin and poly(ADP-ribose) polymerase inhibitors. J Biol Chem 289.9247-9253.

Juan, H. C., Lin, Y., Chen, H. R., and Fann, M. J. (2016). Cdk12 is essential for embryonic development and the maintenance of genomic stability. Cell Death Differ 23, 1038-1048.

Ko, T. K., Kelly, E., and Pines, J. (2001). CrkRS: a novel conserved Cdc2-related protein kinase that colocalises with SC35 speckles. J Cell Sci 114, 2591-2603.

Kumar, A., Coleman, I., Morrissey, C., Zhang, X., True, L. D., Gulati, R., Etzioni, R., Bolouri, H., Montgomery, B., White. T., et al. (2016). Substantial interindividual and limited intraindividual genomic diversity among tumors from men with metastatic prostate cancer. Nat Med 22, 369-378.

Kwon, E. D., Drake, C. G., Scher, H. I., Fizazi, K., Bossi, A., van den Eertwegh, A. J., Krainer, M., Houede, N., Santos, R., Mahammedi, H., et al. (2014). Ipilimumab versus placebo after radiotherapy in patients with metastatic castration-resistant prostate cancer that had progressed after docetaxel chemotherapy (CA184-043): a multicentre, randomised, double-blind, phase 3 trial. Lancet Oncol 15, 700-712.

Law, C. W., Chen, Y., Shi, W., and Smyth, G. K. (2014). Voom: Precision weights unlock linear model analysis tools for RNA-seq read counts. Genome Biol 15, R29.

Lawrence, M., Huber, W., Pages, H., Aboyoun, P., Carlson, M., Gentleman, R., Morgan, M. T., and Carey, V. J. (2013). Software for computing and annotating genomic ranges. PLoS Comput Biol 9, e1003118.

Layer, R. M., Chiang, C., Quinlan, A. R., and Hall, I. M. (2014). LUMPY: a probabilistic framework for structural variant discovery. Genome Biol 15, R84.

Le, D. T., Uram, J. N., Wang, H., Bartlett, B. R., Kemberling, H., Eyring, A. D., Skora, A. D., Luber, B. S., Azad, N. S., Laheru, D., et al. (2015). PD-1 blockade in tumors with mismatch-repair deficiency. N Engl J Med 372, 2509-2520.

Liao, Y., Smyth, G. K., and Shi, W. (2014). FeatureCounts: an efficient general purpose program for assigning sequence reads to genomic features. Bioinformatics 30, 923-930.

Liberzon, A., Birger, C., Thorvaldsdottir, H., Ghandi, M., Mesirov, J. P., and Tamayo, P. (2015). The Molecular Signatures Database (MSigDB) hallmark gene set collection. Cell Syst 1, 417-425.

Mateo, J., Carreira, S., Sandhu, S., Miranda, S., Mossop, H., Perez-Lopez, R., Nava Rodrigues, D., Robinson, D., Omlin, A., Tunariu, N., et al. (2015). DNA-repair defects and olaparib in metastatic prostate cancer. N Engl J Med 373, 1697-1708.

McGranahan, N., Furness, A. J., Rosenthal, R., Ramskov, S., Lyngaa, R., Saini, S. K., Jamal-Hanjani, M., Wilson, G. A., Birkbak, N. J., Hiley, C. T., et al. (2016). Clonal neoantigens elicit T cell immunoreactivity and sensitivity to immune checkpoint blockade. Science 351, 1463-1469.

Mermel, C. H., Schumacher, S. E., Hill, B., Meyerson, M. L., Beroukhim, R., and Getz, G. (2011). GISTIC2.0 facilitates sensitive and confident localization of the targets of focal somatic copy-number alteration in human cancers. Genome Biol 12, R41.

Nagarsheth, N., Wicha, M. S., and Zou, W. (2017). Chemokines in the cancer microenvironment and their relevance in cancer immunotherapy. Nature reviews Immunology 17, 559-572.

Negrini, S., Gorgoulis, V. G., and Halazonetis, T. D. (2010). Genomic instability—an evolving hallmark of cancer. Nat Rev Mol Cell Biol 11, 220-228.

Newton, M. A., *Quintana*, F. A., Den Boon, J. A., Sengupta, S., and Ahlquist, P. (2007). Random-set methods identify distinct aspects of the enrichment signal in gene-set analysis. Ann Appl Stat, 85-106.

Nishino, M., Sholl, L. M., Hodi, F. S., Hatabu, H., and Ramaiya, N. H. (2015). Anti-PD-I-related pneumonitis during cancer immunotherapy. N Engl J Med 373, 288-290.

Northcott, P. A., Buchhalter, I., Morrissy, A. S., Hovestadt, V., Weischenfeldt, J., Ehrenberger, T., Grobner, S., Segura-Wang, M., Zichner, T., Rudneva, V. A., et al. (2017). The whole-genome landscape of medulloblastoma subtypes. Nature 547, 311-317.

O'Neil, N. J., Bailey, M. L., and Hieter, P. (2017). Synthetic lethality and cancer. Nat Rev Genet 18, 613-623.

Olshen, A. B., Venkatraman, E. S., Lucito, R., and Wigler, M. (2004). Circular binary segmentation for the analysis of array-based DNA copy number data. Biostatistics (Oxford, England) 5, 557-572.

Palanisamy, N., Ateeq, B., Kalyana-Sundaram, S., Pflueger, D., Ramnarayanan, K., Shankar, S., Han, B., Cao, Q., Cao, X., Suleman, K., et al. (2010). Rearrangements of the RAF kinase pathway in prostate cancer, gastric cancer and melanoma. Nat Med 16, 793-798.

Parikh, N., Hilsenbeck, S., Creighton, C. J., Dayaram, T., Shuck, R., Shinbrot, E., Xi, L., Gibbs, R. A., Wheeler, D. A., and Donehower, L. A. (2014). Effects of TP53 mutational status on gene expression patterns across 10 human cancer types. J Pathol 232, 522-533.

Platzer, P., Upender, M. B., Wilson, K., Willis, J., Lutterbaugh, J., Nosrati, A., Willson, J. K., Mack, D., Ried, T., and Markowitz, S. (2002). Silence of chromosomal amplifications in colon cancer. Cancer Res 62, 1134-1138.

Polak, P., Kim, J., Braunstein, L. Z., Karlic, R., Haradhavala, N. J., Tiao, G., Rosebrock, D., Livitz, D., Kubler, K., Mouw, K. W., et al. (2017). A mutational signature reveals alterations underlying deficient homologous recombination repair in breast cancer. Nat Genet 49, 1476-1486.

Popova, T., Manic, E., Boeva, V., Battistella, A., Goundiam, O., Smith, N. K., Mueller, C. R., Raynal, V., Mariani, O., Sastre-Garau, X., et al. (2016). Ovarian cancers harboring inactivating mutations in CDK12 display a distinct genomic instability pattern characterized by large tandem duplications. Cancer Res 76, 1882-1891.

Pritchard, C. C., Morrissey, C., Kumar, A., Zhang, X., Smith, C., Coleman, I., Salipante, S. J, Milbank, J., Yu, M., Grady, W. M., et aL. (2014). Complex MSH2 and MSH6 mutations in hypermutated microsatellite unstable advanced prostate cancer. Nat Commun 5, 4988.

Ritchie, M. E., Phipson, B., Wu, D., Hu, Y., Law, C. W., Shi, W., and Smyth, G. K. (2015). limma powers differential expression analyses for RNA-sequencing and microarray studies. Nucleic Acids Res 43, e47.

Robinson, D., Van Allen, E. M., Wu, Y. M., Schultz, N., Lonigro, R. J., Mosquera, J. M., Montgomery, B., Taplin, M. E., Pritchard, C. C., Attard, G., et al. (2015). Integrative clinical genomics of advanced prostate cancer. Cell 161, 1215-1228.

Robinson, D. R., Wu, Y. M., Lonigro, R. J., Vats, P., Cobain, E., Everett, J., Cao, X., Rabban, E., Kumar-Sinha, C., Raymond, V., et al. (2017). Integrative clinical genomics of metastatic cancer. Nature 548, 297-303.

Robinson, M. D., McCarthy, D. J., and Smyth, G. K. (2010). edgeR: a Bioconductor package for differential expression analysis of digital gene expression data. Bioinformatics 26, 139-140.

Saal, L. H., Johansson, P., Holm, K., Gruvberger-Saal, S. K., She, Q. B., Maurer, M., Koujak, S., Ferrando, A. A., Malmstrom, P., Memeo, L., et al. (2007). Poor prognosis in carcinoma is associated with a gene expression signature of aberrant PTEN tumor suppressor pathway activity. Proc Natl Acad Sci USA/04, 7564-7569.

SABiosciences—a QIAGEN company (Oct. 17 2017). The leader for pathway and disease biology research products.

Sergushichev, A. (2016). An algorithm for fast preranked gene set enrichment analysis using cumulative statistic calculation. BioRxiv.

Sharma. P., Hu-Lieskovan, S., Wargo. J. A., and Ribas, A. (2017). Primary, adaptive, and acquired resistance to cancer immunotherapy. Cell 168, 707-723.

Smyth, G. K. (2005). Limma: Linear models for microarray data. In Bioinformatics and computational biology solutions using R and Bioconductor, R. Gentleman, V. J. Carey, W. Huber, R. A. Irizarry, and S. Dudoit, eds. (New York, N. Y.: Springer New York), pp. 397-420.

Strasner, A., and Karin, M. (2015). Immune infiltration and prostate cancer. Front Oncol 5, 128.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Nal Acad Sci USA 102, 15545-15550.

Tang, Y. C., and Amon, A. (2013). Gene copy-number alterations: a cost-benefit analysis. Cell/52, 394-405.

Temko, D., Tomlinson, I., Severini. S., Schuster-Boeckler, B., and Graham, T. (2017). The effects of mutational process and selection on driver mutations across cancer types. BioRxiv.

The Cancer Genome Atlas Research Network (2015). The molecular taxonomy of primary prostate cancer. Cell 163, 1011-1025.

Tomlins, S. A., Rhodes, D. R., Perner, S., Dhanasekaran, S. M., Mehra, R., Sun, X. W., Varambally, S., Cao, X., Tchinda, J., Kuefer, R., et al. (2005). Recurrent fusion of TMPRSS2 and ETS transcription factor genes in prostate cancer. Science 310, 644-648.

Turlach, B., and Weingessel, A. (2013). Quadprog: Functions to solve quadratic programming problems.

Tutt, A., Bertwistle, D., Valentine, J., Gabriel, A., Swift, S., Ross, G., Griffin, C., Thacker, J., and Ashworth, A. (2001). Mutation in Brca2 stimulates error-prone homology-directed repair of DNA double-strand breaks occurring between repeated sequences. EMBO J 20, 4704-4716.

Vander Heiden, M. G., Cantley. L. C., and Thompson. C. B. (2009). Understanding the Warburg effect: the metabolic requirements of cell proliferation. Science 324, 1029-1033.

Vicari, A. P., Figueroa, D. J., Hedrick, J. A., Foster, J. S., Singh, K. P., Menon, S., Copeland. N. G., Gilbert. D. J., Jenkins. N. A., Bacon, K. B., et al. (1997). TECK: a novel CC chemokine specifically expressed by thymic dendritic cells and potentially involved in T cell development. Immunity 7.291-301.

Waldron, L., and Riester, M. (2017). Handy functions for working with HGNC gene symbols and Affymetrix probeset identifiers.

Wu, Y. M., Su, F., Kalyana-Sundaram, S., Khazanov, N., Ateeq, B., Cao, X., Lonigro, R. J., Vats, P., Wang, R., Lin, S. F., et al. (2013). Identification oftargetable FGFR gene fusions in diverse cancers. Cancer Discov 3, 636-647.

Yoshihara, K., Shahmoradgoli, M., Martinez, E., Vegesna, R., Kim, H., Torres-Garcia, W., Trevino, V., Shen, H., Laird, P. W., Levine, D. A., et al. (2013). Inferring tumour purity and stromal and immune cell admixture from expression data. Nat Commun 4, 2612.

Yu, J., Deshmukh, H., Gutmann, R. J., Emnett, R. J., Rodriguez, F. J., Watson, M. A., Nagarajan, R., and Gutmann, D. H. (2009). Alterations of BRAF and HIPK2 loci predominate in sporadic pilocytic astrocytoma. Neurology 73, 1526-1531.

Yuan, X., Li, T., Wang, H., Zhang, T., Barua, M., Borgesi, R. A., Bubley, G. J., Lu, M. L., and Balk, S. P. (2006). Androgen receptor remains critical for cell-cycle progression in androgen-independent CWR22 prostate cancer cells. Am J Pathol 169, 682-696.

Zou, W. (2006). Regulatory T cells, tumour immunity and immunotherapy. Nature reviews Immunology 6, 295-307.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of treating cancer, comprising:
   a) detecting the presence of one or more inactivating mutations of CDK12 in a sample from a subject diagnosed with prostate cancer; and
   b) administering checkpoint inhibitor immunotherapy to subjects with said one or more inactivating mutations of CDK12.

2. The method of claim 1, wherein said prostate cancer is castration-resistant prostate cancer.

3. The method of claim 1, wherein said prostate cancer is metastatic prostate cancer.

4. The method claim 1, wherein said checkpoint inhibitor immunotherapy comprises an anti-PD-1 agent.

5. The method of claim 4, wherein said anti-PD-1 agent is selected from the group consisting of pembrolizumab, nivolumab, REGN2810, MED10680, CT-001, pidilizumab, AMP-224, AMP-514, and PDR001.

6. The method of claim 1, wherein said inactivating mutations of CDK12 are truncating mutations.

7. The method of claim 1, wherein said inactivating mutations of CDK12 are biallelic.

8. The method of claim 1, wherein said inactivating mutations of CDK12 inactivate the kinase domain of CDK12.

9. The method of claim 1, wherein said detecting step comprises sending a sample to a lab to be tested and receiving results of said subject's CDK12 mutation status.

* * * * *

SEQUENCE LISTING

<160> NUMBER OF SEQ ID NOS: 34

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: Synthetic

<400> SEQUENCE: 1
agggagaacg acgaacgtcg                                               20

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: Synthetic

<400> SEQUENCE: 2
ggaatgacga ctgcgtgaac                                               20

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: Synthetic

<400> SEQUENCE: 3
aacacttaat atcccgatgc                                               20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: Synthetic

<400> SEQUENCE: 4
caaatcaaac tagcagattt                                               20

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: Synthetic

<400> SEQUENCE: 5
ggctctataa ctctgaagag                                               20

<210> SEQ ID NO 6
<211> LENGTH: 199
<212> TYPE: PRT
<213> ORGANISM: Homo sapiens

<400> SEQUENCE: 6

Lys Phe Asp Ile Ile Gly Ile Ile Gly Glu Gly Thr Tyr Gly Gln Val
1               5                   10                  15

Tyr Lys Ala Lys Asp Lys Asp Thr Gly Glu Leu Val Ala Leu Lys Lys
            20                  25                  30

Val Arg Leu Asp Asn Glu Lys Glu Gly Phe Pro Ile Thr Ala Ile Arg
        35                  40                  45

```
Glu Ile Lys Ile Leu Arg Gln Leu Ile His Arg Ser Val Val Asn Met
 50                  55                  60

Lys Glu Ile Val Thr Phe Lys Asp Lys Gly Ala Phe Tyr Leu Val
 65                  70                  75                  80

Phe Glu Tyr Met Asp His Asp Leu Met Gly Leu Leu Ser Gly Leu Val
                 85                  90                  95

His Phe Ser Glu Asp His Ile Lys Ser Phe Met Lys Gln Leu Met Glu
                100                 105                 110

Gly Leu Glu Tyr Cys His Lys Lys Asn Phe Leu His Arg Asp Ile Lys
                115                 120                 125

Cys Ser Asn Ile Leu Leu Asn Asn Ser Gly Gln Ile Lys Leu Ala Asp
            130                 135                 140

Phe Gly Leu Ala Arg Leu Tyr Asn Ser Glu Glu Ser Arg Pro Tyr Thr
145                 150                 155                 160

Asn Lys Val Ile Thr Leu Trp Tyr Arg Pro Pro Glu Leu Leu Gly
                165                 170                 175

Glu Glu Arg Tyr Thr Pro Ala Ile Asp Val Trp Ser Cys Gly Cys Ile
                180                 185                 190

Leu Gly Glu Leu Phe Thr Lys
                195

<210> SEQ ID NO 7
<211> LENGTH: 199
<212> TYPE: PRT
<213> ORGANISM: Homo sapiens

<400> SEQUENCE: 7

Lys Phe Asp Ile Ile Gly Ile Ile Gly Glu Gly Thr Tyr Gly Gln Val
1                5                  10                  15

Tyr Lys Ala Arg Asp Lys Asp Thr Gly Glu Met Val Ala Leu Lys Lys
                20                  25                  30

Val Arg Leu Asp Asn Glu Lys Glu Gly Phe Pro Ile Thr Ala Ile Arg
            35                  40                  45

Glu Ile Lys Ile Leu Arg Gln Leu Thr His Gln Ser Ile Ile Asn Met
 50                  55                  60

Lys Glu Ile Val Thr Phe Lys Asp Lys Gly Ala Phe Tyr Leu Val
 65                  70                  75                  80

Phe Glu Tyr Met Asp His Asp Leu Met Gly Leu Leu Ser Gly Leu Val
                 85                  90                  95

His Phe Asn Glu Asn His Ile Lys Ser Phe Met Arg Gln Leu Met Glu
                100                 105                 110

Gly Leu Asp Tyr Cys His Lys Lys Asn Phe Leu His Arg Asp Ile Lys
                115                 120                 125

Cys Ser Asn Ile Leu Leu Asn Asn Arg Gly Gln Ile Lys Leu Ala Asp
            130                 135                 140

Phe Gly Leu Ala Arg Leu Tyr Ser Ser Glu Glu Ser Arg Pro Tyr Thr
145                 150                 155                 160

Asn Lys Val Ile Thr Leu Trp Tyr Arg Pro Pro Glu Leu Leu Gly
                165                 170                 175

Glu Glu Arg Tyr Thr Pro Ala Ile Asp Val Trp Ser Cys Gly Cys Ile
                180                 185                 190

Leu Gly Glu Leu Phe Thr Lys
                195

<210> SEQ ID NO 8
```

```
<211> LENGTH: 198
<212> TYPE: PRT
<213> ORGANISM: Homo sapiens

<400> SEQUENCE: 8

Lys Tyr Glu Lys Leu Ala Lys Ile Gly Gln Gly Thr Phe Gly Glu Val
1               5                   10                  15

Phe Lys Ala Arg His Arg Lys Thr Gly Gln Lys Val Ala Leu Lys Lys
            20                  25                  30

Val Leu Met Glu Asn Glu Lys Glu Gly Phe Pro Ile Thr Ala Leu Arg
        35                  40                  45

Glu Ile Lys Ile Leu Gln Leu Leu Lys His Glu Asn Val Val Asn Leu
50                  55                  60

Ile Glu Ile Cys Arg Tyr Asn Arg Cys Lys Gly Ser Ile Tyr Leu Val
65                  70                  75                  80

Phe Asp Phe Cys Glu His Asp Leu Ala Gly Leu Leu Ser Asn Val Leu
                85                  90                  95

Val Lys Phe Thr Leu Ser Glu Ile Lys Arg Val Met Gln Met Leu Leu
            100                 105                 110

Asn Gly Leu Tyr Tyr Ile His Arg Asn Lys Ile Leu His Arg Asp Met
        115                 120                 125

Lys Ala Ala Asn Val Leu Ile Thr Arg Asp Gly Val Leu Lys Leu Ala
130                 135                 140

Asp Phe Gly Leu Ala Arg Ala Phe Ser Gln Pro Asn Arg Tyr Thr Asn
145                 150                 155                 160

Arg Val Val Thr Leu Trp Tyr Arg Pro Pro Glu Leu Leu Leu Gly Glu
                165                 170                 175

Arg Asp Tyr Gly Pro Pro Ile Asp Leu Trp Gly Ala Gly Cys Ile Met
            180                 185                 190

Ala Glu Met Trp Thr Arg
        195

<210> SEQ ID NO 9
<211> LENGTH: 197
<212> TYPE: PRT
<213> ORGANISM: Homo sapiens

<400> SEQUENCE: 9

Met Phe Gln Lys Val Glu Lys Ile Gly Glu Gly Thr Tyr Gly Val Val
1               5                   10                  15

Tyr Lys Ala Lys Asn Arg Glu Thr Gly Gln Leu Val Ala Leu Lys Lys
            20                  25                  30

Ile Arg Leu Asp Leu Glu Met Glu Gly Val Pro Ser Thr Ala Ile Arg
        35                  40                  45

Glu Ile Ser Leu Leu Lys Glu Leu Lys His Pro Asn Ile Val Arg Leu
50                  55                  60

Leu Asp Val Val His Asn Glu Arg Lys Leu Tyr Leu Val Phe Glu Phe
65                  70                  75                  80

Leu Ser Gln Asp Leu Lys Lys Tyr Met Asp Ser Thr Pro Gly Ser Glu
                85                  90                  95

Leu Pro Leu His Leu Ile Lys Ser Tyr Leu Phe Gln Leu Leu Gln Gly
            100                 105                 110

Val Ser Phe Cys His Ser His Arg Val Ile His Arg Asp Leu Lys Pro
        115                 120                 125

Gln Asn Leu Leu Ile Asn Glu Leu Gly Ala Ile Lys Leu Ala Asp Phe
130                 135                 140
```

```
Gly Leu Ala Arg Ala Phe Gly Val Pro Leu Arg Thr Tyr Thr His Glu
145                 150                 155                 160

Val Val Thr Leu Trp Tyr Arg Ala Pro Glu Ile Leu Leu Gly Ser Lys
                165                 170                 175

Phe Tyr Thr Thr Ala Val Asp Ile Trp Ser Ile Gly Cys Ile Phe Ala
            180                 185                 190

Glu Met Val Thr Arg
        195

<210> SEQ ID NO 10
<211> LENGTH: 197
<212> TYPE: PRT
<213> ORGANISM: Homo sapiens

<400> SEQUENCE: 10

Asn Phe Gln Lys Val Glu Lys Ile Gly Glu Gly Thr Tyr Gly Val Val
1               5                   10                  15

Tyr Lys Ala Arg Asn Lys Leu Thr Gly Glu Val Val Ala Leu Lys Lys
            20                  25                  30

Ile Arg Leu Asp Thr Glu Thr Glu Gly Val Pro Ser Thr Ala Ile Arg
        35                  40                  45

Glu Ile Ser Leu Leu Lys Glu Leu Asn His Pro Asn Ile Val Lys Leu
50                  55                  60

Leu Asp Val Ile His Thr Glu Asn Lys Leu Tyr Leu Val Phe Glu Phe
65                  70                  75                  80

Leu His Gln Asp Leu Lys Lys Phe Met Asp Ala Ser Ala Leu Thr Gly
                85                  90                  95

Ile Pro Leu Pro Leu Ile Lys Ser Tyr Leu Phe Gln Leu Leu Gln Gly
            100                 105                 110

Leu Ala Phe Cys His Ser His Arg Val Leu His Arg Asp Leu Lys Pro
        115                 120                 125

Gln Asn Leu Leu Ile Asn Thr Glu Gly Ala Ile Lys Leu Ala Asp Phe
130                 135                 140

Gly Leu Ala Arg Ala Phe Gly Val Pro Val Arg Thr Tyr Thr His Glu
145                 150                 155                 160

Val Val Thr Leu Trp Tyr Arg Ala Pro Glu Ile Leu Leu Gly Cys Lys
                165                 170                 175

Tyr Tyr Ser Thr Ala Val Asp Ile Trp Ser Leu Gly Cys Ile Phe Ala
            180                 185                 190

Glu Met Val Thr Arg
        195

<210> SEQ ID NO 11
<211> LENGTH: 198
<212> TYPE: PRT
<213> ORGANISM: Homo sapiens

<400> SEQUENCE: 11

Asp Tyr Thr Lys Ile Glu Lys Ile Gly Glu Gly Thr Tyr Gly Val Val
1               5                   10                  15

Tyr Lys Gly Arg His Lys Thr Thr Gly Gln Val Val Ala Met Lys Lys
            20                  25                  30

Ile Arg Leu Glu Ser Glu Glu Glu Gly Val Pro Ser Thr Ala Ile Arg
        35                  40                  45

Glu Ile Ser Leu Leu Lys Glu Leu Arg His Pro Asn Ile Val Ser Leu
50                  55                  60
```

-continued

```
Gln Asp Val Leu Met Gln Asp Ser Arg Leu Tyr Leu Ile Phe Glu Phe
 65                  70                  75                  80

Leu Ser Met Asp Leu Lys Lys Tyr Leu Asp Ser Ile Pro Pro Gly Gln
                 85                  90                  95

Tyr Met Asp Ser Ser Leu Val Lys Ser Tyr Leu Tyr Gln Ile Leu Gln
            100                 105                 110

Gly Ile Val Phe Cys His Ser Arg Arg Val Leu His Arg Asp Leu Lys
        115                 120                 125

Pro Gln Asn Leu Leu Ile Asp Asp Lys Gly Thr Ile Lys Leu Ala Asp
130                 135                 140

Phe Gly Leu Ala Arg Ala Phe Gly Ile Pro Ile Arg Val Tyr Thr His
145                 150                 155                 160

Glu Val Val Thr Leu Trp Tyr Arg Ser Pro Glu Val Leu Leu Gly Ser
                165                 170                 175

Ala Arg Tyr Ser Thr Pro Val Asp Ile Trp Ser Ile Gly Thr Ile Phe
            180                 185                 190

Ala Glu Leu Ala Thr Lys
            195
```

<210> SEQ ID NO 12
<211> LENGTH: 198
<212> TYPE: PRT
<213> ORGANISM: Homo sapiens

<400> SEQUENCE: 12

```
Gln Tyr Cys Ile Leu Gly Arg Ile Gly Glu Gly Ala His Gly Ile Val
  1               5                  10                  15

Phe Lys Ala Lys His Val Glu Thr Gly Glu Ile Val Ala Leu Lys Lys
                 20                  25                  30

Val Ala Leu Arg Arg Leu Glu Asp Gly Phe Pro Asn Gln Ala Leu Arg
             35                  40                  45

Glu Ile Lys Ala Leu Gln Glu Met Glu Asp Asn Gln Tyr Val Val Gln
 50                  55                  60

Leu Lys Ala Val Phe Pro His Gly Gly Gly Phe Val Leu Ala Phe Glu
 65                  70                  75                  80

Phe Met Leu Ser Asp Leu Ala Glu Val Val Arg His Ala Gln Arg Pro
                 85                  90                  95

Leu Ala Gln Ala Gln Val Lys Ser Tyr Leu Gln Met Leu Leu Lys Gly
            100                 105                 110

Val Ala Phe Cys His Ala Asn Asn Ile Val His Arg Asp Leu Lys Pro
        115                 120                 125

Ala Asn Leu Leu Ile Ser Ala Ser Gly Gln Leu Lys Ile Ala Asp Phe
130                 135                 140

Gly Leu Ala Arg Val Phe Ser Pro Asp Gly Ser Arg Leu Tyr Thr His
145                 150                 155                 160

Gln Val Ala Thr Arg Trp Tyr Arg Ala Pro Glu Leu Leu Tyr Gly Ala
                165                 170                 175

Arg Gln Tyr Asp Gln Gly Val Asp Leu Trp Ser Val Gly Cys Ile Met
            180                 185                 190

Gly Glu Leu Leu Asn Gly
            195
```

<210> SEQ ID NO 13
<211> LENGTH: 196
<212> TYPE: PRT

<213> ORGANISM: Homo sapiens

<400> SEQUENCE: 13

Lys Tyr Glu Lys Leu Glu Lys Ile Gly Glu Gly Thr Tyr Gly Thr Val
1               5                   10                  15

Phe Lys Ala Lys Asn Arg Glu Thr His Glu Ile Val Ala Leu Lys Arg
            20                  25                  30

Val Arg Leu Asp Asp Asp Glu Gly Val Pro Ser Ser Ala Leu Arg
        35                  40                  45

Glu Ile Cys Leu Leu Lys Glu Leu Lys His Lys Asn Ile Val Arg Leu
    50                  55                  60

His Asp Val Leu His Ser Asp Lys Lys Leu Thr Leu Val Phe Glu Phe
65                  70                  75                  80

Cys Asp Gln Asp Leu Lys Lys Tyr Phe Asp Ser Cys Asn Gly Asp Leu
                85                  90                  95

Asp Pro Glu Ile Val Lys Ser Phe Leu Phe Gln Leu Leu Lys Gly Leu
            100                 105                 110

Gly Phe Cys His Ser Arg Asn Val Leu His Arg Asp Leu Lys Pro Gln
        115                 120                 125

Asn Leu Leu Ile Asn Arg Asn Gly Glu Leu Lys Leu Ala Asp Phe Gly
130                 135                 140

Leu Ala Arg Ala Phe Gly Ile Pro Val Arg Cys Tyr Ser Ala Glu Val
145                 150                 155                 160

Val Thr Leu Trp Tyr Arg Pro Pro Asp Val Leu Phe Gly Ala Lys Leu
                165                 170                 175

Tyr Ser Thr Ser Ile Asp Met Trp Ser Ala Gly Cys Ile Phe Ala Glu
            180                 185                 190

Leu Ala Asn Ala
        195

<210> SEQ ID NO 14
<211> LENGTH: 197
<212> TYPE: PRT
<213> ORGANISM: Homo sapiens

<400> SEQUENCE: 14

Glu Phe Gln Cys Leu Asn Arg Ile Glu Glu Gly Thr Tyr Gly Val Val
1               5                   10                  15

Tyr Arg Ala Lys Asp Lys Lys Thr Asp Glu Ile Val Ala Leu Lys Arg
            20                  25                  30

Leu Lys Met Glu Lys Glu Lys Glu Gly Phe Pro Ile Thr Ser Leu Arg
        35                  40                  45

Glu Ile Asn Thr Ile Leu Lys Ala Gln His Pro Asn Ile Val Thr Val
    50                  55                  60

Arg Glu Ile Val Val Ser Asn Met Asp Lys Ile Tyr Ile Val Met Asn
65                  70                  75                  80

Tyr Val Glu His Asp Leu Lys Ser Leu Met Glu Thr Met Lys Gln Pro
                85                  90                  95

Phe Leu Pro Gly Glu Val Lys Thr Leu Met Ile Gln Leu Leu Arg Gly
            100                 105                 110

Val Lys His Leu His Asp Asn Trp Ile Leu His Arg Asp Leu Lys Thr
        115                 120                 125

Ser Asn Leu Leu Leu Ser His Ala Gly Ile Leu Lys Val Gly Asp Phe
130                 135                 140

Gly Leu Ala Arg Glu Tyr Gly Ser Pro Leu Lys Ala Tyr Thr Pro Val

```
                145                 150                 155                 160
Val Val Thr Leu Trp Tyr Arg Ala Pro Glu Leu Leu Gly Ala Lys
                165                 170                 175

Glu Tyr Ser Thr Ala Val Asp Met Trp Ser Val Gly Cys Ile Phe Gly
                180                 185                 190

Glu Leu Leu Thr Gln
                195
```

<210> SEQ ID NO 15
<211> LENGTH: 198
<212> TYPE: PRT
<213> ORGANISM: Homo sapiens

<400> SEQUENCE: 15

```
Glu Phe Glu Lys Leu Asn Arg Ile Gly Glu Gly Thr Tyr Gly Ile Val
1               5                   10                  15

Tyr Arg Ala Arg Asp Thr Gln Thr Asp Glu Ile Val Ala Leu Lys Lys
                20                  25                  30

Val Arg Met Asp Lys Glu Lys Asp Gly Ile Pro Ile Ser Ser Leu Arg
                35                  40                  45

Glu Ile Thr Leu Leu Arg Leu Arg His Pro Asn Ile Val Glu Leu
50                  55                  60

Lys Glu Val Val Gly Asn His Leu Glu Ser Ile Phe Leu Val Met
65                  70                  75                  80

Gly Tyr Cys Glu Gln Asp Leu Ala Ser Leu Leu Glu Asn Met Pro Thr
                85                  90                  95

Pro Phe Ser Glu Ala Gln Val Lys Cys Ile Val Leu Gln Val Leu Arg
                100                 105                 110

Gly Leu Gln Tyr Leu His Arg Asn Phe Ile Ile His Arg Asp Leu Lys
                115                 120                 125

Val Ser Asn Leu Leu Met Thr Asp Lys Gly Cys Val Lys Thr Ala Asp
                130                 135                 140

Phe Gly Leu Ala Arg Ala Tyr Gly Val Pro Val Lys Pro Met Thr Pro
145                 150                 155                 160

Lys Val Val Thr Leu Trp Tyr Arg Ala Pro Glu Leu Leu Leu Gly Thr
                165                 170                 175

Thr Thr Gln Thr Thr Ser Ile Asp Met Trp Ala Val Gly Cys Ile Leu
                180                 185                 190

Ala Glu Leu Leu Ala His
                195
```

<210> SEQ ID NO 16
<211> LENGTH: 195
<212> TYPE: PRT
<213> ORGANISM: Homo sapiens

<400> SEQUENCE: 16

```
Thr Tyr Val Lys Leu Asp Lys Leu Gly Glu Gly Thr Tyr Ala Thr Val
1               5                   10                  15

Phe Lys Gly Arg Ser Lys Leu Thr Glu Asn Leu Val Ala Leu Lys Glu
                20                  25                  30

Ile Arg Leu Glu His Glu Glu Gly Ala Pro Cys Thr Ala Ile Arg Glu
                35                  40                  45

Val Ser Leu Leu Lys Asn Leu Lys His Ala Asn Ile Val Thr Leu His
50                  55                  60

Asp Leu Ile His Thr Asp Arg Ser Leu Thr Leu Val Phe Glu Tyr Leu
```

```
                65                  70                  75                  80
Asp Ser Asp Leu Lys Gln Tyr Leu Asp His Cys Gly Asn Leu Met Ser
                    85                  90                  95

Met His Asn Val Lys Ile Phe Met Phe Gln Leu Leu Arg Gly Leu Ala
                    100                 105                 110

Tyr Cys His His Arg Lys Ile Leu His Arg Asp Leu Lys Pro Gln Asn
                    115                 120                 125

Leu Leu Ile Asn Glu Arg Gly Glu Leu Lys Leu Ala Asp Phe Gly Leu
            130                 135                 140

Ala Arg Ala Lys Ser Val Pro Thr Lys Thr Tyr Ser Asn Glu Val Val
145                 150                 155                 160

Thr Leu Trp Tyr Arg Pro Asp Val Leu Leu Gly Ser Thr Glu Tyr
                    165                 170                 175

Ser Thr Pro Ile Asp Met Trp Gly Val Gly Cys Ile His Tyr Glu Met
                    180                 185                 190

Ala Thr Gly
            195

<210> SEQ ID NO 17
<211> LENGTH: 195
<212> TYPE: PRT
<213> ORGANISM: Homo sapiens

<400> SEQUENCE: 17

Thr Tyr Ile Lys Leu Asp Lys Leu Gly Glu Gly Thr Tyr Ala Thr Val
1               5                   10                  15

Tyr Lys Gly Lys Ser Lys Leu Thr Asp Asn Leu Val Ala Leu Lys Glu
                20                  25                  30

Ile Arg Leu Glu His Glu Glu Gly Ala Pro Cys Thr Ala Ile Arg Glu
            35                  40                  45

Val Ser Leu Leu Lys Asp Leu Lys His Ala Asn Ile Val Thr Leu His
        50                  55                  60

Asp Ile Ile His Thr Glu Lys Ser Leu Thr Leu Val Phe Glu Tyr Leu
65                  70                  75                  80

Asp Lys Asp Leu Lys Gln Tyr Leu Asp Asp Cys Gly Asn Ile Ile Asn
                    85                  90                  95

Met His Asn Val Lys Leu Phe Leu Phe Gln Leu Leu Arg Gly Leu Ala
                    100                 105                 110

Tyr Cys His Arg Gln Lys Val Leu His Arg Asp Leu Lys Pro Gln Asn
                    115                 120                 125

Leu Leu Ile Asn Glu Arg Gly Glu Leu Lys Leu Ala Asp Phe Gly Leu
            130                 135                 140

Ala Arg Ala Lys Ser Ile Pro Thr Lys Thr Tyr Ser Asn Glu Val Val
145                 150                 155                 160

Thr Leu Trp Tyr Arg Pro Pro Asp Ile Leu Leu Gly Ser Thr Asp Tyr
                    165                 170                 175

Ser Thr Gln Ile Asp Met Trp Gly Val Gly Cys Ile Phe Tyr Glu Met
                    180                 185                 190

Ala Thr Gly
            195

<210> SEQ ID NO 18
<211> LENGTH: 195
<212> TYPE: PRT
<213> ORGANISM: Homo sapiens
```

```
<400> SEQUENCE: 18

Thr Tyr Ile Lys Leu Glu Lys Leu Gly Glu Gly Thr Tyr Ala Thr Val
1               5                   10                  15

Tyr Lys Gly Arg Ser Lys Leu Thr Glu Asn Leu Val Ala Leu Lys Glu
            20                  25                  30

Ile Arg Leu Glu His Glu Gly Ala Pro Cys Thr Ala Ile Arg Glu
        35                  40                  45

Val Ser Leu Leu Lys Asp Leu Lys His Ala Asn Ile Val Thr Leu His
    50                  55                  60

Asp Ile Val His Thr Asp Lys Ser Leu Thr Leu Val Phe Glu Tyr Leu
65                  70                  75                  80

Asp Lys Asp Leu Lys Gln Tyr Met Asp Asp Cys Gly Asn Ile Met Ser
                85                  90                  95

Met His Asn Val Lys Leu Phe Leu Tyr Gln Ile Leu Arg Gly Leu Ala
            100                 105                 110

Tyr Cys His Arg Arg Lys Val Leu His Arg Asp Leu Lys Pro Gln Asn
        115                 120                 125

Leu Leu Ile Asn Glu Lys Gly Glu Leu Lys Leu Ala Asp Phe Gly Leu
    130                 135                 140

Ala Arg Ala Lys Ser Val Pro Thr Lys Thr Tyr Ser Asn Glu Val Val
145                 150                 155                 160

Thr Leu Trp Tyr Arg Pro Pro Asp Val Leu Leu Gly Ser Ser Glu Tyr
                165                 170                 175

Ser Thr Gln Ile Asp Met Trp Gly Val Gly Cys Ile Phe Phe Glu Met
            180                 185                 190

Ala Ser Gly
        195

<210> SEQ ID NO 19
<211> LENGTH: 199
<212> TYPE: PRT
<213> ORGANISM: Homo sapiens

<400> SEQUENCE: 19

Arg Tyr Glu Lys Leu Asp Phe Leu Gly Glu Gly Gln Phe Ala Thr Val
1               5                   10                  15

Tyr Lys Ala Arg Asp Lys Asn Thr Asn Gln Ile Val Ala Ile Lys Lys
            20                  25                  30

Ile Lys Leu Gly His Arg Ser Glu Ala Lys Asp Gly Ile Asn Arg Thr
        35                  40                  45

Ala Leu Arg Glu Ile Lys Leu Leu Gln Glu Leu Ser His Pro Asn Ile
    50                  55                  60

Ile Gly Leu Leu Asp Ala Phe Gly His Lys Ser Asn Ile Ser Leu Val
65                  70                  75                  80

Phe Asp Phe Met Glu Thr Asp Leu Glu Val Ile Ile Lys Asp Asn Ser
                85                  90                  95

Leu Val Leu Thr Pro Ser His Ile Lys Ala Tyr Met Leu Met Thr Leu
            100                 105                 110

Gln Gly Leu Glu Tyr Leu His Gln His Trp Ile Leu His Arg Asp Leu
        115                 120                 125

Lys Pro Asn Asn Leu Leu Asp Glu Asn Gly Val Leu Lys Leu Ala
    130                 135                 140

Asp Phe Gly Leu Ala Lys Ser Phe Gly Ser Pro Asn Arg Ala Tyr Thr
145                 150                 155                 160
```

His Gln Val Val Thr Arg Trp Tyr Arg Ala Pro Glu Leu Leu Phe Gly
                165                 170                 175

Ala Arg Met Tyr Gly Val Gly Val Asp Met Trp Ala Val Gly Cys Ile
            180                 185                 190

Leu Ala Glu Leu Leu Arg
        195

<210> SEQ ID NO 20
<211> LENGTH: 200
<212> TYPE: PRT
<213> ORGANISM: Homo sapiens

<400> SEQUENCE: 20

Gln Tyr Glu Cys Val Ala Glu Ile Gly Glu Gly Ala Tyr Gly Lys Val
1               5                   10                  15

Phe Lys Ala Arg Asp Leu Lys Asn Gly Arg Phe Val Ala Leu Lys
            20                  25                  30

Arg Val Arg Val Gln Thr Gly Glu Glu Gly Met Pro Leu Ser Thr Ile
        35                  40                  45

Arg Glu Val Ala Val Leu Arg His Leu Glu Thr Phe Glu His Pro Asn
    50                  55                  60

Val Val Arg Leu Phe Asp Val Cys Thr Asp Arg Glu Thr Lys Leu Thr
65                  70                  75                  80

Leu Val Phe Glu His Val Asp Gln Asp Leu Thr Thr Tyr Leu Asp Lys
                85                  90                  95

Val Pro Glu Pro Gly Val Pro Thr Glu Thr Ile Lys Asp Met Met Phe
            100                 105                 110

Gln Leu Leu Arg Gly Leu Asp Phe Leu His Ser His Arg Val Val His
        115                 120                 125

Arg Asp Leu Lys Pro Gln Asn Ile Leu Val Thr Ser Ser Gly Gln Ile
    130                 135                 140

Lys Leu Ala Asp Phe Gly Leu Ala Arg Ile Tyr Ser Phe Gln Met Ala
145                 150                 155                 160

Leu Thr Ser Val Val Thr Leu Trp Tyr Arg Ala Pro Glu Val Leu
                165                 170                 175

Leu Gln Ser Ser Tyr Ala Thr Pro Val Asp Leu Trp Ser Val Gly Cys
            180                 185                 190

Ile Phe Ala Glu Met Phe Arg Arg
        195                 200

<210> SEQ ID NO 21
<211> LENGTH: 195
<212> TYPE: PRT
<213> ORGANISM: Homo sapiens

<400> SEQUENCE: 21

Ser Tyr Glu Lys Leu Glu Lys Leu Gly Glu Gly Ser Tyr Ala Thr Val
1               5                   10                  15

Tyr Lys Gly Lys Ser Lys Val Asn Gly Lys Leu Val Ala Leu Lys Val
            20                  25                  30

Ile Arg Leu Gln Glu Glu Glu Gly Thr Pro Phe Thr Ala Ile Arg Glu
        35                  40                  45

Ala Ser Leu Leu Lys Gly Leu Lys His Ala Asn Ile Val Leu Leu His
    50                  55                  60

Asp Ile Ile His Thr Lys Glu Thr Leu Thr Leu Val Phe Glu Tyr Val
65                  70                  75                  80

His Thr Asp Leu Cys Gln Tyr Met Asp Lys His Pro Gly Gly Leu His
                85                  90                  95

Pro Asp Asn Val Lys Leu Phe Leu Phe Gln Leu Leu Arg Gly Leu Ser
            100                 105                 110

Tyr Ile His Gln Arg Tyr Ile Leu His Arg Asp Leu Lys Pro Gln Asn
        115                 120                 125

Leu Leu Ile Ser Asp Thr Gly Glu Leu Lys Ala Asp Phe Gly Leu
    130                 135                 140

Ala Arg Ala Lys Ser Val Pro Ser His Thr Tyr Ser Asn Glu Val Val
145                 150                 155                 160

Thr Leu Trp Tyr Arg Pro Pro Asp Val Leu Leu Gly Ser Thr Glu Tyr
                165                 170                 175

Ser Thr Cys Leu Asp Met Trp Gly Val Gly Cys Ile Phe Val Glu Met
            180                 185                 190

Ile Gln Gly
        195

<210> SEQ ID NO 22
<211> LENGTH: 195
<212> TYPE: PRT
<213> ORGANISM: Homo sapiens

<400> SEQUENCE: 22

Ser Tyr Leu Asn Leu Glu Lys Leu Gly Glu Gly Ser Tyr Ala Thr Val
1               5                   10                  15

Tyr Lys Gly Ile Ser Arg Ile Asn Gly Gln Leu Val Ala Leu Lys Val
            20                  25                  30

Ile Ser Met Asn Ala Glu Glu Gly Val Pro Phe Thr Ala Ile Arg Glu
        35                  40                  45

Ala Ser Leu Leu Lys Gly Leu Lys His Ala Asn Ile Val Leu Leu His
    50                  55                  60

Asp Ile Ile His Thr Lys Glu Thr Leu Thr Phe Val Phe Glu Tyr Met
65                  70                  75                  80

His Thr Asp Leu Ala Gln Tyr Met Ser Gln His Pro Gly Gly Leu His
                85                  90                  95

Pro His Asn Val Arg Leu Phe Met Phe Gln Leu Leu Arg Gly Leu Ala
            100                 105                 110

Tyr Ile His His Gln His Val Leu His Arg Asp Leu Lys Pro Gln Asn
        115                 120                 125

Leu Leu Ile Ser His Leu Gly Glu Leu Lys Leu Ala Asp Phe Gly Leu
    130                 135                 140

Ala Arg Ala Lys Ser Ile Pro Ser Gln Thr Tyr Ser Ser Glu Val Val
145                 150                 155                 160

Thr Leu Trp Tyr Arg Pro Pro Asp Ala Leu Leu Gly Ala Thr Glu Tyr
                165                 170                 175

Ser Ser Glu Leu Asp Ile Trp Gly Ala Gly Cys Ile Phe Ile Glu Met
            180                 185                 190

Phe Gln Gly
        195

<210> SEQ ID NO 23
<211> LENGTH: 202
<212> TYPE: PRT
<213> ORGANISM: Homo sapiens

<400> SEQUENCE: 23

-continued

Arg Tyr Glu Pro Val Ala Glu Ile Gly Val Gly Ala Tyr Gly Thr Val
1               5                   10                  15

Tyr Lys Ala Arg Asp Pro His Ser Gly His Phe Val Ala Leu Lys Ser
            20                  25                  30

Val Arg Val Pro Asn Gly Gly Gly Gly Gly Gly Leu Pro Ile Ser
        35                  40                  45

Thr Val Arg Glu Val Ala Leu Leu Arg Arg Leu Glu Ala Phe Glu His
50                  55                  60

Pro Asn Val Val Arg Leu Met Asp Val Cys Ala Asp Arg Glu Ile Lys
65                  70                  75                  80

Val Thr Leu Val Phe Glu His Val Asp Gln Asp Leu Arg Thr Tyr Leu
            85                  90                  95

Asp Lys Ala Pro Pro Gly Leu Pro Ala Glu Thr Ile Lys Asp Leu
            100                 105                 110

Met Arg Gln Phe Leu Arg Gly Leu Asp Phe Leu His Ala Asn Cys Ile
            115                 120                 125

Val His Arg Asp Leu Lys Pro Glu Asn Ile Leu Val Thr Ser Gly Gly
            130                 135                 140

Thr Val Lys Leu Ala Asp Phe Gly Leu Ala Arg Ile Tyr Ser Tyr Gln
145                 150                 155                 160

Met Ala Leu Thr Pro Val Val Thr Leu Trp Tyr Arg Ala Pro Glu
            165                 170                 175

Val Leu Leu Gln Ser Thr Tyr Ala Thr Pro Val Asp Met Trp Ser Val
            180                 185                 190

Gly Cys Ile Phe Ala Glu Met Phe Arg Arg
            195                 200

<210> SEQ ID NO 24
<211> LENGTH: 196
<212> TYPE: PRT
<213> ORGANISM: Homo sapiens

<400> SEQUENCE: 24

Lys Tyr Glu Lys Ile Gly Lys Ile Gly Glu Gly Ser Tyr Gly Val Val
1               5                   10                  15

Phe Lys Cys Arg Asn Arg Asp Thr Gly Gln Ile Val Ala Ile Lys Lys
            20                  25                  30

Phe Leu Glu Ser Glu Asp Asp Pro Val Ile Lys Lys Ile Ala Leu Arg
            35                  40                  45

Glu Ile Arg Met Leu Lys Gln Leu Lys His Pro Asn Leu Val Asn Leu
50                  55                  60

Leu Glu Val Phe Arg Arg Lys Arg Arg Leu His Leu Val Phe Glu Tyr
65                  70                  75                  80

Cys Asp His Thr Val Leu His Glu Leu Asp Arg Tyr Gln Arg Gly Val
            85                  90                  95

Pro Glu His Leu Val Lys Ser Ile Thr Trp Gln Thr Leu Gln Ala Val
            100                 105                 110

Asn Phe Cys His Lys His Asn Cys Ile His Arg Asp Val Lys Pro Glu
            115                 120                 125

Asn Ile Leu Ile Thr Lys His Ser Val Ile Lys Leu Cys Asp Phe Gly
            130                 135                 140

Phe Ala Arg Leu Leu Thr Gly Pro Ser Asp Tyr Tyr Thr Asp Tyr Val
145                 150                 155                 160

Ala Thr Arg Trp Tyr Arg Ser Pro Glu Leu Leu Val Gly Asp Thr Gln
            165                 170                 175

```
Tyr Gly Pro Pro Val Asp Val Trp Ala Ile Gly Cys Val Phe Ala Glu
            180                 185                 190

Leu Leu Ser Gly
        195

<210> SEQ ID NO 25
<211> LENGTH: 196
<212> TYPE: PRT
<213> ORGANISM: Homo sapiens

<400> SEQUENCE: 25

Lys Tyr Glu Asn Leu Gly Leu Val Gly Glu Gly Ser Tyr Gly Met Val
1               5                   10                  15

Met Lys Cys Arg Asn Lys Asp Thr Gly Arg Ile Val Ala Ile Lys Lys
            20                  25                  30

Phe Leu Glu Ser Asp Asp Asp Lys Met Val Lys Lys Ile Ala Met Arg
        35                  40                  45

Glu Ile Lys Leu Leu Lys Gln Leu Arg His Glu Asn Leu Val Asn Leu
    50                  55                  60

Leu Glu Val Cys Lys Lys Lys Arg Trp Tyr Leu Val Phe Glu Phe
65                  70                  75                  80

Val Asp His Thr Ile Leu Asp Asp Leu Glu Leu Phe Pro Asn Gly Leu
                85                  90                  95

Asp Tyr Gln Val Val Gln Lys Tyr Leu Phe Gln Ile Ile Asn Gly Ile
            100                 105                 110

Gly Phe Cys His Ser His Asn Ile Ile His Arg Asp Ile Lys Pro Glu
        115                 120                 125

Asn Ile Leu Val Ser Gln Ser Gly Val Val Lys Leu Cys Asp Phe Gly
    130                 135                 140

Phe Ala Arg Thr Leu Ala Ala Pro Gly Glu Val Tyr Thr Asp Tyr Val
145                 150                 155                 160

Ala Thr Arg Trp Tyr Arg Ala Pro Glu Leu Leu Val Gly Asp Val Lys
                165                 170                 175

Tyr Gly Lys Ala Val Asp Val Trp Ala Ile Gly Cys Leu Val Thr Glu
            180                 185                 190

Met Phe Met Gly
        195

<210> SEQ ID NO 26
<211> LENGTH: 197
<212> TYPE: PRT
<213> ORGANISM: Homo sapiens

<400> SEQUENCE: 26

Arg Tyr Thr Asn Leu Ser Tyr Ile Gly Glu Gly Ala Tyr Gly Met Val
1               5                   10                  15

Cys Ser Ala Tyr Asp Asn Val Asn Lys Val Arg Val Ala Ile Lys Lys
            20                  25                  30

Ile Ser Pro Phe Glu His Gln Thr Tyr Cys Gln Arg Thr Leu Arg Glu
        35                  40                  45

Ile Lys Ile Leu Leu Arg Phe Arg His Glu Asn Ile Ile Gly Ile Asn
    50                  55                  60

Asp Ile Ile Arg Glu Gln Met Lys Asp Val Tyr Ile Val Gln Asp Leu
65                  70                  75                  80

Met Glu Thr Asp Leu Tyr Lys Leu Leu Lys Thr Gln His Leu Ser Asn
                85                  90                  95
```

```
Asp His Ile Cys Tyr Phe Leu Tyr Gln Ile Leu Arg Gly Leu Lys Tyr
                100                 105                 110

Ile His Ser Ala Asn Val Leu His Arg Asp Leu Lys Pro Ser Asn Leu
            115                 120                 125

Leu Leu Asn Thr Thr Cys Asp Leu Lys Ile Cys Asp Phe Gly Leu Ala
130                 135                 140

Arg Val Ala Asp Pro Asp His Asp His Thr Gly Phe Leu Thr Glu Tyr
145                 150                 155                 160

Val Ala Thr Arg Trp Tyr Arg Ala Pro Glu Ile Met Leu Asn Ser Lys
                165                 170                 175

Gly Tyr Thr Lys Ser Ile Asp Ile Trp Ser Val Gly Cys Ile Leu Ala
            180                 185                 190

Glu Met Leu Ser Asn
        195

<210> SEQ ID NO 27
<211> LENGTH: 197
<212> TYPE: PRT
<213> ORGANISM: Homo sapiens

<400> SEQUENCE: 27

Arg Tyr Thr Gln Leu Gln Tyr Ile Gly Glu Gly Ala Tyr Gly Met Val
1               5                   10                  15

Ser Ser Ala Tyr Asp His Val Arg Lys Thr Arg Val Ala Ile Lys Lys
                20                  25                  30

Ile Ser Pro Phe Glu His Gln Thr Tyr Cys Gln Arg Thr Leu Arg Glu
            35                  40                  45

Ile Gln Ile Leu Leu Arg Phe Arg His Glu Asn Val Ile Gly Ile Arg
        50                  55                  60

Asp Ile Leu Arg Glu Ala Met Arg Asp Val Tyr Ile Val Gln Asp Leu
65                  70                  75                  80

Met Glu Thr Asp Leu Tyr Lys Leu Leu Lys Ser Gln Gln Leu Ser Asn
                85                  90                  95

Asp His Ile Cys Tyr Phe Leu Tyr Gln Ile Leu Arg Gly Leu Lys Tyr
                100                 105                 110

Ile His Ser Ala Asn Val Leu His Arg Asp Leu Lys Pro Ser Asn Leu
            115                 120                 125

Leu Ile Asn Thr Thr Cys Asp Leu Lys Ile Cys Asp Phe Gly Leu Ala
130                 135                 140

Arg Ile Ala Asp Pro Glu His Asp His Thr Gly Phe Leu Thr Glu Tyr
145                 150                 155                 160

Val Ala Thr Arg Trp Tyr Arg Ala Pro Glu Ile Met Leu Asn Ser Lys
                165                 170                 175

Gly Tyr Thr Lys Ser Ile Asp Ile Trp Ser Val Gly Cys Ile Leu Ala
            180                 185                 190

Glu Met Leu Ser Asn
        195

<210> SEQ ID NO 28
<211> LENGTH: 198
<212> TYPE: PRT
<213> ORGANISM: Homo sapiens

<400> SEQUENCE: 28

Glu Tyr Glu Ile Ile Glu Thr Ile Gly Asn Gly Ala Tyr Gly Val Val
1               5                   10                  15
```

```
Ser Ser Ala Arg Arg Leu Thr Gly Gln Gln Val Ala Ile Lys Lys
            20                  25                  30

Ile Pro Asn Ala Phe Asp Val Val Thr Asn Ala Lys Arg Thr Leu Arg
 35                      40                  45

Glu Leu Lys Ile Leu Lys His Phe Lys His Asp Asn Ile Ile Ala Ile
 50                      55                  60

Lys Asp Ile Leu Arg Gly Glu Phe Lys Ser Val Tyr Val Val Leu Asp
65                   70                  75                  80

Leu Met Glu Ser Asp Leu His Gln Ile Ile Ser Ser Gln Pro Leu Thr
                 85                  90                  95

Leu Glu His Val Arg Tyr Phe Leu Tyr Gln Leu Leu Arg Gly Leu Lys
                100                 105                 110

Tyr Met His Ser Ala Gln Val Ile His Arg Asp Leu Lys Pro Ser Asn
            115                 120                 125

Leu Leu Val Asn Glu Asn Cys Glu Leu Lys Ile Gly Asp Phe Gly Met
130                 135                 140

Ala Arg Gly Leu Cys Ser Pro Ala Glu His Gln Tyr Phe Met Thr Glu
145                 150                 155                 160

Tyr Val Ala Thr Arg Trp Tyr Arg Ala Pro Glu Leu Met Leu Ser Leu
                165                 170                 175

His Glu Tyr Thr Gln Ala Ile Asp Leu Trp Ser Val Gly Cys Ile Phe
            180                 185                 190

Gly Glu Met Leu Ala Arg
            195

<210> SEQ ID NO 29
<211> LENGTH: 192
<212> TYPE: PRT
<213> ORGANISM: Homo sapiens

<400> SEQUENCE: 29

Val Tyr Arg Asp Leu Gln Pro Val Gly Ser Gly Ala Tyr Gly Ala Val
1               5                   10                  15

Cys Ser Ala Val Asp Gly Arg Thr Gly Ala Lys Val Ala Ile Lys Lys
            20                  25                  30

Leu Tyr Arg Pro Phe Gln Ser Glu Leu Phe Ala Lys Arg Ala Tyr Arg
 35                      40                  45

Glu Leu Arg Leu Leu Lys His Met Arg His Glu Asn Val Ile Gly Leu
 50                      55                  60

Leu Asp Val Phe Thr Asp Phe Thr Asp Phe Tyr Leu Val Met Pro
65                   70                  75                  80

Phe Met Gly Thr Asp Leu Gly Lys Leu Met Lys His Glu Lys Leu Gly
                 85                  90                  95

Glu Asp Arg Ile Gln Phe Leu Val Tyr Gln Met Leu Lys Gly Leu Arg
                100                 105                 110

Tyr Ile His Ala Ala Gly Ile Ile His Arg Asp Leu Lys Pro Gly Asn
            115                 120                 125

Leu Ala Val Asn Glu Asp Cys Glu Leu Lys Ile Leu Asp Phe Gly Leu
130                 135                 140

Ala Arg Gln Ala Asp Ser Glu Met Thr Gly Tyr Val Val Thr Arg Trp
145                 150                 155                 160

Tyr Arg Ala Pro Glu Val Ile Leu Asn Trp Met Arg Tyr Thr Gln Thr
                165                 170                 175

Val Asp Ile Trp Ser Val Gly Cys Ile Met Ala Glu Met Ile Thr Gly
```

```
                180              185              190

<210> SEQ ID NO 30
<211> LENGTH: 189
<212> TYPE: PRT
<213> ORGANISM: Homo sapiens

<400> SEQUENCE: 30

Arg Tyr Thr Thr Met Arg Gln Leu Gly Asp Gly Thr Tyr Gly Ser Val
1               5                   10                  15

Leu Met Gly Lys Ser Asn Glu Ser Gly Leu Val Ala Ile Lys Arg
            20                  25                  30

Met Lys Arg Lys Phe Tyr Ser Trp Asp Glu Cys Met Asn Leu Arg Glu
        35                  40                  45

Val Lys Ser Leu Lys Lys Leu Asn His Ala Asn Val Ile Lys Leu Lys
    50                  55                  60

Glu Val Ile Arg Glu Asn Asp His Leu Tyr Phe Ile Phe Glu Tyr Met
65                  70                  75                  80

Lys Glu Asn Leu Tyr Gln Leu Met Asp Arg Asn Lys Leu Phe Pro Glu
                85                  90                  95

Ser Val Ile Arg Asn Ile Met Tyr Gln Ile Leu Gln Gly Leu Ala Phe
            100                 105                 110

Ile His Lys His Gly Phe Phe His Arg Asp Met Lys Pro Glu Asn Leu
        115                 120                 125

Leu Cys Met Glu Leu Val Lys Ile Ala Asp Phe Gly Leu Ala Arg Glu
    130                 135                 140

Leu Arg Pro Pro Tyr Thr Asp Tyr Val Ser Thr Arg Trp Tyr Arg Ala
145                 150                 155                 160

Pro Glu Val Leu Leu Arg Ser Ser Val Tyr Ser Ser Pro Ile Asp Val
                165                 170                 175

Trp Ala Val Gly Ser Ile Met Ala Glu Leu Tyr Met Leu
            180                 185

<210> SEQ ID NO 31
<211> LENGTH: 199
<212> TYPE: PRT
<213> ORGANISM: Homo sapiens

<400> SEQUENCE: 31

Glu Tyr Glu Gly Cys Lys Val Gly Arg Gly Thr Tyr Gly His Val Tyr
1               5                   10                  15

Lys Ala Arg Arg Lys Asp Gly Lys Asp Glu Lys Glu Tyr Ala Leu Lys
            20                  25                  30

Gln Ile Glu Gly Thr Gly Ile Ser Met Ser Ala Cys Arg Glu Ile Ala
        35                  40                  45

Leu Leu Arg Glu Leu Lys His Pro Asn Val Ile Ala Leu Gln Lys Val
    50                  55                  60

Phe Leu His Ser Asp Arg Lys Val Trp Leu Leu Phe Asp Tyr Ala Glu
65                  70                  75                  80

His Asp Leu Trp His Ile Ile Lys Ala Asn Lys Lys Pro Met Gln Leu
                85                  90                  95

Pro Arg Ser Met Val Lys Ser Leu Leu Tyr Gln Ile Leu Asp Gly Ile
            100                 105                 110

His Tyr Leu His Ala Asn Trp Val Leu His Arg Asp Leu Lys Pro Ala
        115                 120                 125

Asn Ile Leu Val Met Glu Arg Gly Arg Val Lys Ile Ala Asp Met Gly
```

```
            130                 135                 140
Phe Ala Arg Leu Phe Asn Ser Pro Leu Lys Pro Leu Ala Asp Leu Asp
145                 150                 155                 160

Pro Val Val Thr Phe Trp Tyr Arg Ala Pro Glu Leu Leu Leu Gly
                165                 170                 175

Ala Arg His Tyr Thr Lys Ala Ile Asp Ile Trp Ala Ile Gly Cys Ile
                180                 185                 190

Phe Ala Glu Leu Leu Thr Ser
            195

<210> SEQ ID NO 32
<211> LENGTH: 197
<212> TYPE: PRT
<213> ORGANISM: Homo sapiens

<400> SEQUENCE: 32

Asp Ile Glu Pro Asp Arg Pro Ile Gly Tyr Gly Ala Phe Gly Val Val
1               5                   10                  15

Trp Ser Val Thr Asp Pro Arg Asp Gly Lys Arg Val Ala Leu Lys Lys
                20                  25                  30

Met Pro Asn Val Phe Gln Asn Leu Val Ser Cys Lys Arg Val Phe Arg
            35                  40                  45

Glu Leu Lys Met Leu Cys Phe Phe Lys His Asp Asn Val Leu Ser Ala
50                  55                  60

Leu Asp Ile Leu Gln Asp Tyr Phe Glu Glu Ile Tyr Val Val Thr Glu
65                  70                  75                  80

Leu Met Gln Ser Asp Leu His Lys Ile Ile Val Ser Pro Gln Pro Leu
                85                  90                  95

Ser Ser Asp His Val Lys Val Phe Leu Tyr Gln Ile Leu Arg Gly Leu
            100                 105                 110

Lys Tyr Leu His Ser Ala Gly Ile Leu His Arg Asp Ile Lys Pro Gly
        115                 120                 125

Asn Leu Leu Val Asn Ser Asn Cys Val Leu Lys Ile Cys Asp Phe Gly
    130                 135                 140

Leu Ala Arg Val Glu Glu Leu Asp Glu Ser Arg His Met Thr Gln Glu
145                 150                 155                 160

Val Val Thr Gln Tyr Tyr Arg Ala Pro Glu Ile Leu Met Gly Ser Arg
                165                 170                 175

His Tyr Ser Asn Ala Ile Asp Ile Trp Ser Val Gly Cys Ile Phe Ala
                180                 185                 190

Glu Leu Leu Gly Arg
            195

<210> SEQ ID NO 33
<211> LENGTH: 191
<212> TYPE: PRT
<213> ORGANISM: Homo sapiens

<400> SEQUENCE: 33

Thr Tyr Val Ser Pro Thr His Val Gly Ser Gly Ala Tyr Gly Ser Val
1               5                   10                  15

Cys Ser Ala Ile Asp Lys Arg Ser Gly Glu Lys Val Ala Ile Lys Lys
                20                  25                  30

Leu Ser Arg Pro Phe Gln Ser Glu Ile Phe Ala Lys Arg Ala Tyr Arg
            35                  40                  45

Glu Leu Leu Leu Leu Lys His Met Gln His Glu Asn Val Ile Gly Leu
```

```
            50                   55                  60
Leu Asp Val Phe Thr Arg Asn Phe Tyr Asp Phe Tyr Leu Val Met Pro
 65                   70                  75                  80

Phe Met Gln Thr Asp Leu Gln Lys Ile Met Gly Met Glu Phe Ser Glu
                 85                  90                  95

Glu Lys Ile Gln Tyr Leu Val Tyr Gln Met Leu Lys Gly Leu Lys Tyr
                100                 105                 110

Ile His Ser Ala Gly Val Val His Arg Asp Leu Lys Pro Gly Asn Leu
                115                 120                 125

Ala Val Asn Glu Asp Cys Glu Leu Lys Ile Leu Asp Phe Gly Leu Ala
            130                 135                 140

Arg His Ala Asp Ala Glu Met Thr Gly Tyr Val Val Thr Arg Trp Tyr
145                 150                 155                 160

Arg Ala Pro Glu Val Ile Leu Ser Trp Met His Tyr Asn Gln Thr Val
                165                 170                 175

Asp Ile Trp Ser Val Gly Cys Ile Met Ala Glu Met Leu Thr Gly
                180                 185                 190

<210> SEQ ID NO 34
<211> LENGTH: 198
<212> TYPE: PRT
<213> ORGANISM: Homo sapiens

<400> SEQUENCE: 34

Arg Tyr Leu Leu Arg Arg Gln Leu Gly Gln Gly Ala Tyr Gly Ile Val
  1               5                  10                  15

Trp Lys Ala Val Asp Arg Arg Thr Gly Glu Val Val Ala Ile Lys Lys
                 20                  25                  30

Ile Phe Asp Ala Phe Arg Asp Lys Thr Asp Ala Gln Arg Thr Phe Arg
             35                  40                  45

Glu Ile Thr Leu Leu Gln Glu Phe Gly Asp His Pro Asn Ile Ile Ser
         50                  55                  60

Leu Leu Asp Val Ile Arg Glu Asn Asp Arg Asp Ile Tyr Leu Val Phe
 65                  70                  75                  80

Glu Phe Met Asp Thr Asp Leu Asn Ala Val Ile Arg Lys Gly Gly Leu
                 85                  90                  95

Leu Gln Asp Val His Val Arg Ser Ile Phe Tyr Gln Leu Leu Arg Ala
                100                 105                 110

Thr Arg Phe Leu His Ser Gly His Val Val His Arg Asp Gln Lys Pro
             115                 120                 125

Ser Asn Val Leu Leu Asp Ala Asn Cys Thr Val Lys Leu Cys Asp Phe
        130                 135                 140

Gly Leu Ala Arg Ser Leu Gly Gly Pro Glu Asp Gln Ala Val Thr Glu
145                 150                 155                 160

Tyr Val Ala Thr Arg Trp Tyr Arg Ala Pro Glu Val Leu Leu Ser Ser
                165                 170                 175

His Arg Tyr Thr Leu Gly Val Asp Met Trp Ser Leu Gly Cys Ile Leu
                180                 185                 190

Gly Glu Met Leu Arg Gly
                195
```